(12) United States Patent
Falber

(10) Patent No.: US 8,551,769 B2
(45) Date of Patent: Oct. 8, 2013

(54) METHOD AND APPARATUS FOR CULTIVATION OF ALGAE AND CYANOBACTERIA

(75) Inventor: Alexander Falber, Bellevue Hill (AU)

(73) Assignee: Zero Discharge Pty Ltd., Prahran, Victoria (AU)

( * ) Notice: Subject to any disclaimer, the term of this patent is extended or adjusted under 35 U.S.C. 154(b) by 38 days.

(21) Appl. No.: 13/194,778

(22) Filed: Jul. 29, 2011

(65) Prior Publication Data

US 2012/0034679 A1 Feb. 9, 2012

(30) Foreign Application Priority Data

| Jan. 30, 2009 | (AU) | 2009900346 |
| Aug. 24, 2009 | (AU) | 2009904028 |
| Aug. 4, 2010 | (AU) | 2010903485 |
| Jun. 3, 2011 | (AU) | 2011902211 |

(51) Int. Cl.
C12M 1/00 (2006.01)
C12M 3/00 (2006.01)

(52) U.S. Cl.
USPC ............. 435/292.1; 435/294.1; 435/293.1; 435/968; 252/586; 252/587; 252/588

(58) Field of Classification Search
USPC ........ 435/292.1, 294.1, 293.1, 968; 252/586, 252/587, 588
See application file for complete search history.

(56) References Cited

U.S. PATENT DOCUMENTS

| 4,420,796 A | 12/1983 | Mori |
| 4,632,692 A * | 12/1986 | Lebesgue et al. ............... 71/10 |
| 4,927,231 A | 5/1990 | Levatter |
| 4,952,443 A | 8/1990 | Gravisse |
| 5,857,052 A | 1/1999 | Nath |
| 5,993,020 A | 11/1999 | Koike |
| 6,272,265 B1 | 8/2001 | Franklin |
| 6,287,852 B1 * | 9/2001 | Kondo et al. ............ 435/292.1 |
| 6,507,688 B1 | 1/2003 | Nath |
| 6,509,188 B1 | 1/2003 | Trösch et al. |
| 6,584,714 B1 | 7/2003 | Wehrmann et al. |
| 2007/0048859 A1 | 3/2007 | Sears |
| 2007/0189701 A1 | 8/2007 | Chakmakjian et al. |
| 2008/0160591 A1 * | 7/2008 | Willson et al. ............... 435/132 |

(Continued)

FOREIGN PATENT DOCUMENTS

| CN | 1982433 | 6/2007 |
| DE | 102005011839 | 9/2006 |

(Continued)

OTHER PUBLICATIONS

Australian International-Type Search Report dated Jul. 21, 2011, from Australian Application No. 2011902211, filed Jun. 3, 2011.

(Continued)

*Primary Examiner* — Nathan Bowers
(74) *Attorney, Agent, or Firm* — Klarquist Sparkman, LLP

(57) ABSTRACT

The invention relates to a method of cultivation of algae or cyanobacteria in the presence of a luminous material that converts light of a first wavelength to a second wavelength more suitable for use in photosynthesis by the algae or cyanobacteria, and apparatus for performing the method. In one embodiment the apparatus (50) is of flexible plastic with fluorescent light concentrator or light guide (76) and perforated pipe (56) for bubbling carbon dioxide through the culture. The algae or cyanobacteria may be used to produce biofuels.

19 Claims, 27 Drawing Sheets

(56) References Cited

U.S. PATENT DOCUMENTS

| | | | |
|---|---|---|---|
| 2009/0155864 A1* | 6/2009 | Bauer et al. | 435/134 |
| 2010/0053939 A1 | 3/2010 | Fan et al. | |
| 2010/0087006 A1 | 4/2010 | Gressel et al. | |
| 2011/0111490 A1* | 5/2011 | Lu et al. | 435/292.1 |
| 2011/0281295 A1* | 11/2011 | Sylvestre | 435/29 |

FOREIGN PATENT DOCUMENTS

| | | |
|---|---|---|
| JP | 04-091781 | 3/1992 |
| JP | 04-166017 | 6/1992 |
| JP | 04-287678 | 10/1992 |
| WO | WO 99/20736 | 4/1999 |
| WO | WO 03/009012 | 1/2003 |
| WO | WO 2008/079724 | 7/2008 |
| WO | WO 2010/085853 | 8/2010 |

OTHER PUBLICATIONS

International Search Report for International Application No. PCT/AU2010/000090 dated Jun. 4, 2010.

* cited by examiner

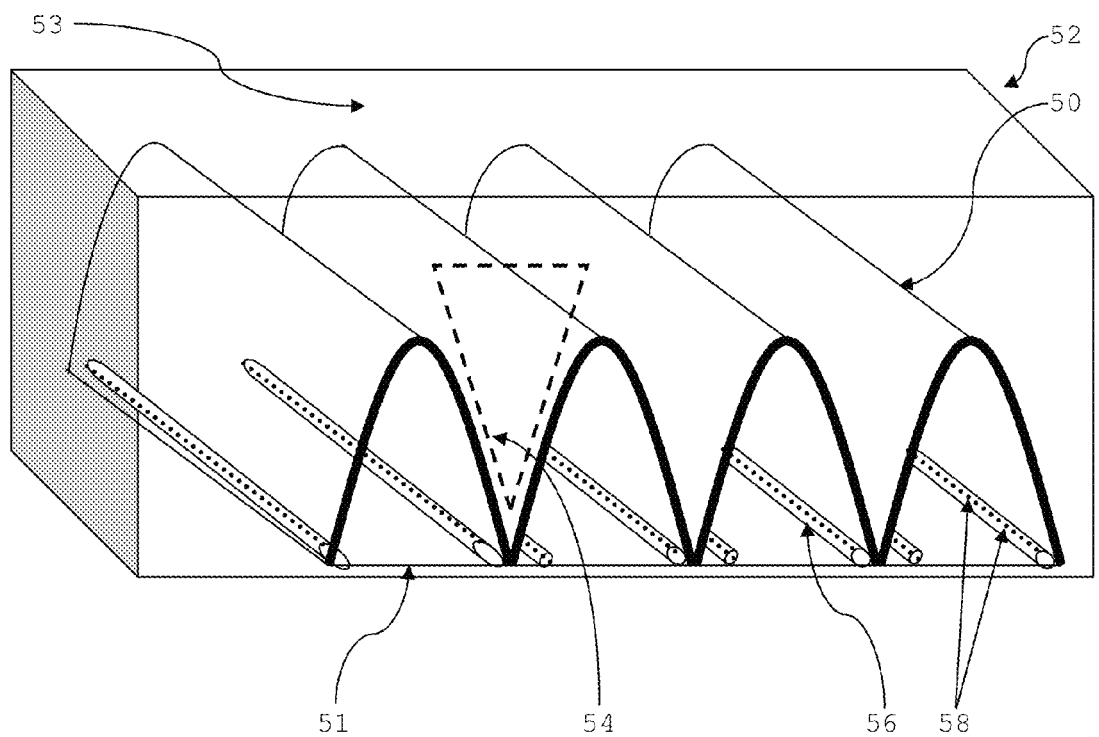
Figure 4a.
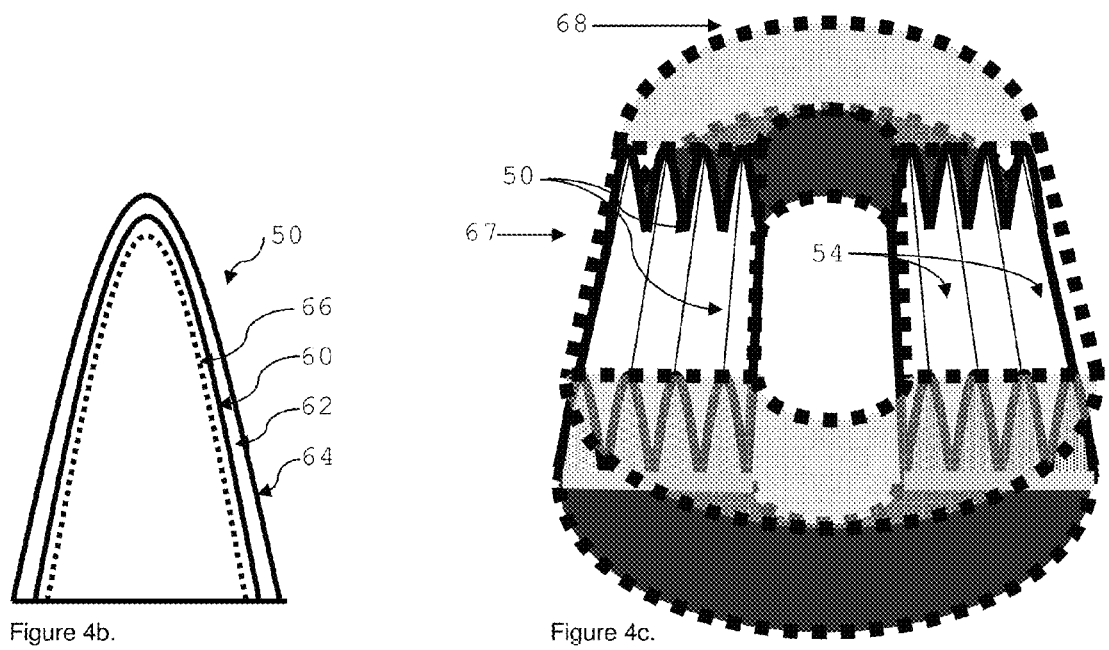
Figure 4b.
Figure 4c.

METHOD AND APPARATUS FOR CULTIVATION OF ALGAE AND CYANOBACTERIA

This application is a continuation-in-part of International patent application PCT/AU2010/000090 filed 29 Jan. 2010, which claims priority to Australian provisional patent application 2009900346 filed 30 Jan. 2009, and Australian provisional patent application 2009904028 filed 24 Aug. 2009, all of which are incorporated herein by reference. This application also claims priority to Australian provisional patent application 2010903485 filed 4 Aug. 2010, and Australian provisional patent application 2011902211 filed 3 Jun. 2011, both of which are incorporated herein by reference.

FIELD

The invention relates to an algae containment apparatus and a bioreactor, and to uses and methods for growing algae or cyanobacteria related thereto. The invention also relates to a light guide, and to uses and methods related thereto.

BACKGROUND

Production of biofuel from renewable processes is a key step towards securing a more responsible energy economy for the future. But beyond this, these fuels must be used in way that does not generate, or minimises, harmful emissions such as carbon dioxide.

Many important advances in biofuel production have been made. However, while advances in commercial production of algae has made great leaps regarding species selection, growth media, and even genetic manipulation, there remains a disproportionate lack of advance in the areas relating to working algal pond depth and harvesting. Algal pond depth is restricted by limited penetration of sunlight into the pond. Efficient harvesting of large quantities of algae requires large expenditures of energy and money.

Closed bioreactors are one means to overcome some of these disadvantages. However, such bioreactors are severely limited by cost and infrastructure requirements especially for biofuel applications. Open ponds are much more economic, particularly for cultivating algae, but are often is restricted by the availability of light to specific dimensions within the algal ponds. That is, light may only penetrate to a certain depth leaving many algae with sub-optimal illumination for growth, or even no light for growth.

In addition most algae growing systems, e.g. closed bioreactors or open ponds, experience photo-inhibition caused by over exposure to sunlight levels at the water surface. In an open pond this occurs a within the first few centimeters of water where little algae growth results. Only after the incoming sunlight intensity has been greatly reduced by the absorbance of photo-inhibited algae at the surface, do algae begin to grow at intermediate depths.

Furthermore, algae depend on photosynthetic pigments, such as chlorophyll, that selectively absorb certain wavelengths of light while other wavelengths are of lesser use, thus further reducing the overall utility of incoming solar radiation. As a result, algae systems exhibit low solar-photosynthetic efficiency. By most estimates, the photosynthetic efficiencies of current algae bioreactor systems average between 2% to 7% and have a maximum theoretical yield of 11% solar-photosynthetic efficiency.

Therefore, there is a need for an improved bioreactor that addresses the disadvantages of previous bioreactors with respect to bioreactor design, cost, and the inherent biological incompatibilities between the available light in such bioreactors and the algal photosynthetic system.

It is to be understood that any reference herein to prior art does not constitute an admission that such art forms a part of the common general knowledge in the art, in Australia or any other country.

SUMMARY

A first aspect provides an algae containment apparatus, for growing an aquatic plant, an alga or a cyanobacterium, the algae containment apparatus comprising a first luminescent material that emits visible light suitable for growing the aquatic plant, alga or cyanobacterium, wherein the algae containment apparatus is capable of forming a first light guide.

A second aspect provides a bioreactor comprising the algae containment apparatus of the first aspect.

A third aspect provides a method for growing an aquatic plant, an alga or a cyanobacterium comprising growing the aquatic plant, alga or cyanobacterium in the algae containment apparatus of the first aspect.

BRIEF DESCRIPTION OF THE DRAWINGS

FIG. 1$a$ depicts absorbance spectra for chlorophyll a and chlorophyll b and a schematic absorbance spectrum for a luminescent material that absorbs green light. Also depicted is the corresponding schematic emission spectrum for the luminescent material illustrating emission of red light that overlaps with chlorophyll absorbance.

FIG. 1$b$ depicts absorbance spectra corresponding to those illustrated in FIG. 1$a$, without the schematic absorbance and emission spectra of the luminescent material. Also illustrated are the absorbance spectra of β-carotene, phycoerythrin and phycocyanin. Phycoerythrin and phycocyanin are phycobilins that absorb light for photosynthesis in cyanobacteria.

FIG. 1$c$ depicts absorbance spectra of chlorophyll a, chlorophyll b, and carotenoids (top) and the related photosynthetic action spectrum (bottom).

FIG. 4$a$ is an orthogonal section of an open pond bioreactor comprising a plurality of the algae containment apparatus.

FIG. 4$b$ is a transverse cross section of an algae containment apparatus.

FIG. 4$c$ depicts an overhead perspective view of an alternative raceway bioreactor comprising a plurality of algae containment apparatus.

FIG. 4$d$ illustrates the shading and luminescent effects when algae are grown in algae containment apparatus in sunlight.

FIG. 4$e$ is an orthogonal view of an algae containment apparatus comprising a light guide positioned on top of the algae containment apparatus.

DETAILED DESCRIPTION

Figure 1A:
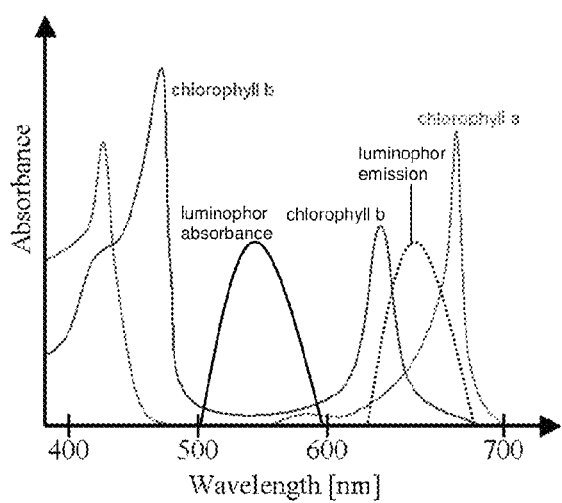
FIG. 1 provides absorbance spectra of chlorophylls and similar compounds.

The shallow depths at which traditional open pond algal systems operate to allow sufficient exposure to sunlight require large areas to obtain adequate algal growth. Bioreactors require smaller areas and allow larger volumes of algal growth, but suffer from the problem of restricted availability of light at depth.

The present apparatus and methods overcome this limitation by increasing the solar efficiency of algae grown in the bioreactor. Thus, more algae may be grown in a smaller volume of growth medium. Furthermore, the depth of the bioreactor may be up to 10 times greater than current designs and therefore would require 10 times less land area. Most importantly, due to the optimised light spectrum in the system, algae will be able to grow at higher concentrations within the bioreactor. Additionally, fewer materials and less transparent tubing should be required compared with current bioreactors.

Thus, the present disclosure provides the following advantages:
- increased photosynthetic efficiency by conversion of light absorbed at a low level into light absorbed at a higher level;
- sustained algal or cyanobacterial growth at depths beyond that penetrable by a light source;
- improved efficiency of open systems towards the efficiency of closed systems;
- improved efficiency of closed systems;
- sustained algal or cyanobacterial growth during the night;
- reduced land use by replacement of ponds with bioreactors;
- utilisation of carbon dioxide from industrial and agricultural sources for photosynthesis; and
- ease of harvesting.

Plants, algae or cyanobacteria grown according to the present disclosure can be used to produce biofuels, feeds, foods, food additives, bioactives such as pharmaceuticals and antibiotics, bioplastics, industrial chemicals or specialty chemicals.

In some embodiments, the luminescent material is disposed in or coated on a substrate. Thus, the substrate may emit light to the algae or cyanobacteria. In some embodiments, the substrate provides growing surfaces for the algae or cyanobacteria.

In one embodiment, the bioreactor comprises a substrate for providing growing surfaces for the algae or cyanobacteria. The substrate may comprise the luminescent material.

In some embodiments, the algae are grown in water or growth medium that is near, or in contact with, the luminescent material.

In one embodiment, the luminescent material may be part of a light guide that distributes light evenly down a water column in the shape of a sheet, tube, or other useful geometry where the algae are allowed to grow in a growth medium. The light guide functions according to methods and materials known in the art in a fashion optimised for the algae containment apparatus or bioreactor.

If used in a terrestrial environment for example, a liquid-filled light guide may comprise a single wall containing the liquid, where the change in refractive index is provided by the ambient atmosphere.

If used in an aquatic environment for example, a liquid-filled light guide may comprise a double wall comprising an inner wall containing the liquid and spaced apart from an outer wall, where the change in refractive index is provided by air, vacuum, or any number of transparent materials of a lower index of refraction than the inner liquid and filling the cavity formed by the spaced apart double walls. Alternatively, the cavity formed between the spaced-apart double walls may be filled with a gas, for example an inert gas such as nitrogen, carbon dioxide or argon as found in U.S. Pat. No. 4,420,796. In such a light conduit, the air or other gas provides an appropriate refractive index to guide light in the conduit.

In some embodiments, the first wavelength or wavelength range comprises ultraviolet or visible light and the second wavelength or wavelength range comprises visible light. In another embodiment, the first wavelength or wavelength range comprises green visible light and the second wavelength or wavelength range comprises red visible light. Typically, the first wavelength or wavelength range comprises about 500 nm to about 600 nm and the second wavelength or wavelength range comprises about 600 nm to about 700 nm.

Figure 1C:
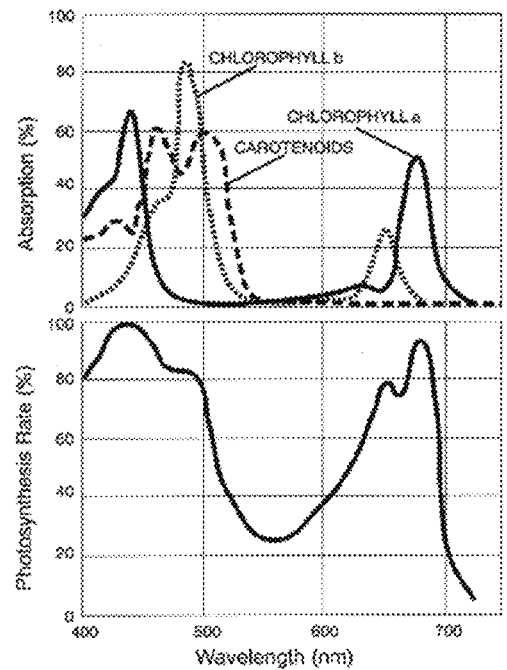
Figure 1B:
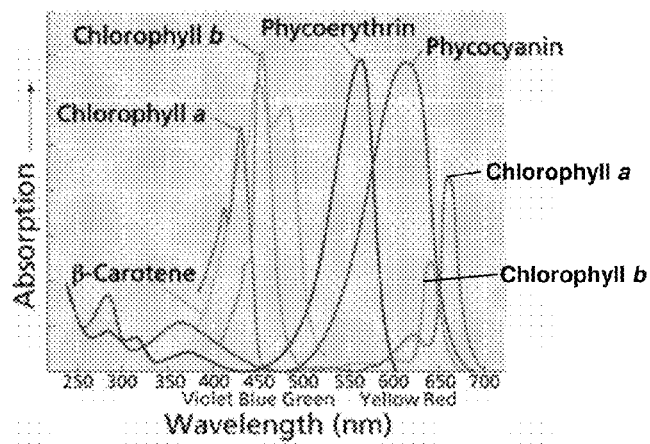

By most estimates, algae systems have a maximum theoretical yield of 11% solar-photosynthetic efficiency. Photosynthesis can provide up to 40% efficiency for conversion of solar energy to glucose at the wavelengths at which chlorophyll absorbs, i.e. 420 nm and 650 nm (FIG. 1). At other wavelengths of the spectrum, however, photosynthesis is less than 1% efficient so that the whole spectrum averages between 5% to 10% efficiency. Up to 90% of all inefficiencies related to bioreactors for mass scale algae growth are related to incompatibility between the received solar radiation and the biologically optimal conditions for algae growth in terms of intensity and wavelength. The present disclosure addresses this incompatibility by promoting selective light absorbance through luminescent conversion of unused light to absorbable light, and thus may improve the solar efficiency of photosynthesis in a bioreactor or open pond.

The luminescent conversion of unused light to absorbable light may allow growth of algae or cyanobacteria at night or at depths at which light does not naturally penetrate.

In other embodiments, the first wavelength or wavelength range comprises ultraviolet light and the second wavelength or wavelength range comprises violet or blue visible light. Generally, the first wavelength or wavelength range comprises about 250 nm to about 400 nm and the second wavelength or wavelength range comprises about 400 nm to about 500 nm.

In further embodiments, the first wavelength or wavelength range comprises ultraviolet or blue light and the second wavelength or wavelength range comprises green, yellow, orange or red visible light. The first wavelength or wavelength range may comprise about 250 nm to about 400 nm and the second wavelength or wavelength range comprises about 450 nm to about 650 nm.

In further embodiments, the luminescent material comprises:

a calcium sulfate phosphor; a zinc sulfate phosphor; a strontium aluminate phosphor; a calcium aluminate phosphor; a CaSrS phosphor; a CaS phosphor; or yttrium aluminium garnet (YAG, $Y_3Al_5O_{12}$), terbium aluminium garnet (TAG, $Tb_3Al_5O_{12}$), or Zex.

Alternatively, the luminescent material may comprise:

a halogen-substituted, alkaline earth metal aluminate doped with at least one rare earth element activator, or a composition of: aL.bM.cAl.dSi.pP.O.:fR, wherein L is selected from Na and/or K; M is a divalent metal selected from one or more of the group consisting of Sr, Ca, Mg and Ba; Al, Si, P and O represent their respective elements; R is selected from one or more rare earth element activators; and wherein the variables a, b, c, d, p and f are: $0.0<a<0.1$; $0.0<b<0.3$; $0.0<c<0.4$; $0.0<d<0.3$; $0.0<p<0.5$; and $0.0<f\leq0.25$, with the proviso that at least one of the variables d and p is >0, and at least one of the variables a and b is >0.

Otherwise, the luminescent material may comprise:

antimony-activated calcium fluorophosphate, lead-activated calcium tungstate, tin-activated strontium magnesium orthophosphate or manganese-activated magnesium fluorogermanate;

yttrium and/or gadolinium oxides activated by trivalent europium and having the formula $(Y_aGd_{1-a})_2O_3{:}Eu^{3+}$, preferably a=1;

calcium- and terbium-activated aluminates, silicates, phosphates and borates selected from compounds of the formulae $CeMgAl_{11}O_{19}{:}Tb$ $Y_2SiO_5{:}Ce,Tb$ $LaPO_4{:}Ce,Tb$ $LaMgB_5O_{10}{:}Ce,Tb$; or alkaline earth hexagonal aluminates of the B-alumina structure, or alkaline earth chlorophosphates, each activated by divalent europium and having the formula $BaMgAl_{10}O_{17}{:}Eu^{2+}$ $BaMg_{1.7}Al_{20}O_{32.7}{:}Eu_{2+}$ $BaMg_2Al_{24}O_{39}{:}Eu_{2+}$ $(Sr,Ca,Ba)_{10}Cl_2(PO_4)_6{:}Eu^{2+}$.

According to some embodiments, the luminescent material is disposed in or coated on a substrate. The substrate provides growing surfaces for the algae or cyanobacteria. The luminescent material may be disposed in or coated on one or more surfaces of the substrate. In certain embodiments, the substrate may comprise more than one luminescent material. If more than one substrate is present, the individual substrates may comprise different luminescent materials or the individual substrates may comprise more than one luminescent material. If more than one luminescent material is present, the luminescent materials may be separated or mixed.

In some embodiments, the substrate comprises a dielectric material. The dielectric material may comprise a polymer, glass, or quartz. The polymer may comprise acrylate or polycarbonate. In one embodiment, the polymer is polymethyl methacrylate. Quartz and certain polymers may be of benefit because they transmit UV light.

In one embodiment, the substrate is the luminescent material.

In one embodiment, the bioreactor includes a bank or storage cell comprising a further luminescent material for use in the bioreactor during the night or at depths not exposed to light. In one embodiment, such luminescent materials will have long glow times and provide low light levels necessary for heterotrophic, nocturnal growth of algae using any number of organic carbon sources as is known in the art.

In some embodiments, the luminescent material absorbs the first wavelength or wavelength range from sunlight. Alternatively, the luminescent material may absorb the first wavelength or wavelength range from an artificial light source, such as a fluorescent light.

In particular embodiments, the bioreactor utilises an industrial source of carbon dioxide. The industrial source of carbon dioxide may be post-combustion carbon dioxide, pre-combustion carbon dioxide, or flue gas, either treated or untreated. Post-combustion carbon dioxide may be isolated using a solvent, a membrane, a zeolite, or a cryogen. In some embodiments, the solvent is an amine. Typically, the solvent is monoethanolamine (MEA) or triethanolamine (TEA). In alternative embodiments, pre-combustion carbon dioxide may be isolated using integrated gasification combined cycle (IGCC). In some embodiments, IGCC produces hydrogen or syngas.

In another embodiment, the carbon dioxide is received as untreated flue gases and is absorbed by the algae growth medium kept at a basic pH where the algae take up inorganic carbon as anionic carbonates where algae species, such as *Coccolithophores*, known for their ability to take up calcium carbonates, are grown in the bioreactor or pond.

In another embodiment, the carbon dioxide is received from untreated flue gases from a power station utilising oxygen fired combustion where flue gases can be up to 95% carbon dioxide. Such systems may or may not use recycled flue gases to dilute the pure oxygen.

In other embodiments, the bioreactor utilises an agricultural source of carbon dioxide. For example, dairy effluent wastewater may be treated in a bio-digester to generate biogas, typically a mixture of methane and carbon dioxide. Emissions from combustion of the biogas may be used as a source of carbon dioxide for photosynthesis as well as the carbon dioxide component of the biogas itself. Alternatively, human wastewater or sewage, either treated or untreated, may be utilised.

In one embodiment, the bioreactor comprises, or is co-operative with, a bio-digester.

Persons skilled in the art will appreciate that suitable bioreactors, or bioreactors that may be suitably adapted, are known.

In some embodiments, the substrate may be filtered. Filtering enables isolation of the substrate for simple harvesting of the algae. In one embodiment, the algae or cyanobacteria may be harvested from the substrate. Harvesting may comprise wiping, scraping, washing, rinsing, drying or partially drying the algae or cyanobacteria, or altering the pH of the growth medium to disrupt binding of the algae.

In one embodiment, where algae are grown in water and are not bound to, a surface, harvesting is accomplished by preliminary concentration of the algae followed by aggregation and filtration or centrifugation. Preliminary concentration can be accomplished using sonic standing waves in a controlled containment that causes algae to concentrate at the nodes of the standing waves. The columns of concentrated algae can be diverted or separated from water with a lower concentration of algae. This concentrate can then be aggregated, filtrated, or centrifuged as is known in the art.

As used in the subject specification, the singular forms "a", "an" and "the" include plural aspects unless the context clearly dictates otherwise. Thus, for example, reference to "a luminescent material" includes a single luminescent material, as well as two or more luminescent materials and so forth.

As used herein, "acrylate" refers to a polymer, homopolymer or copolymer, derived from the monomer acrylic acid or its derivatives possessing one or more functional groups. Derivatives include, for example, methyl acrylate, ethyl acrylate, methacrylate and methyl methacrylate.

As used herein, "plant" and "plants" refer to the singular and plural forms of the word, respectively. "Plants" include any photosynthetic organism comprising chlorophyll, particularly chlorophyll a and chlorophyll b, that is not an alga or a cyanobacterium as herein defined. Generally, plants possess cellulose in their cell walls. Plants include trees, herbs, bushes, grasses, vines, ferns and mosses.

Plants may be ornamental, utilitarian or crop plants, including agriculture, horticulture, aquaculture and hydroponic crop plants, such as vegetables, forestry plants or fruit trees.

The plant may be terrestrial or aquatic.

The plant part may be a bud, a fruit, a seed, a flower, a leaf, a branch or a stem, or any other part that will benefit from light of the second wavelength or wavelength range emitted by the luminescent material.

As used herein, "alga" and "algae" refer to the singular and plural forms of the word, respectively. "Algae" lack the many distinct organs found in plants, but comprise a nucleus enclosed within a membrane and chloroplasts bound in one or more membranes. "Algae" are eukaryotic organisms that comprise chlorophyll that harvests sunlight for autotrophism via photosynthesis. Chlorophyll includes chlorophyll a, chlorophyll b, and chlorophyll c. Each of chlorophyll a, b, and c possess two major absorbance peaks in the electromagnetic spectrum: one near 420 nm and one near 650 nm (blue light and red light, respectively; FIG. 1). Chlorophyll has a lesser degree of absorbance of ultraviolet (UV), green, yellow, orange, or infrared light. "Algae" include Axodines, Bolidomonas, Brown algae, Charophyta, Cryptomonads, Diatoms, Dinoflagellates, Euglenids, Eustigmatophytes, Glaucophytes, Golden algae, Green algae, Heterokonts, Pelagophyceae, Phaetothamniophyceae, Pinguiophyceae, Prymnesiophyta, Raphidophytes, Red algae, Synurids, and Yellow-green algae. Microscopic algae and phytoplankton are particularly contemplated.

Photosynthetic algae are relatively simple and cost-effective to grow and maintain. Algae can grow photosynthetically using carbon dioxide and sunlight, plus a minimum amount of trace nutrients. They also can alternatively or additionally grow heterotrophically on another carbon source, such as glucose or sucrose, or waste water. They are generally regarded as environmentally friendly and safe for human operators.

Chlorophyll includes chlorophyll a, chlorophyll b, and chlorophyll c. Each of chlorophyll a, b, and c possess two major absorbance peaks in the electromagnetic spectrum: one near 420 nm and one near 650 nm (blue light and red light, respectively; FIG. 1). Chlorophyll has a lesser degree of absorbance of ultraviolet (UV), green, yellow, orange, or infrared light. Photosynthetic pigments in algae include chlorophyll a and chlorophyll b.

The luminescent material can be a useful tool for light-dependent growth process and can enhance the growth of any green plants as long as all physical nutrients are supplied.

Flowering plants, fruits, and vegetables can exhibit improved growth and quality by enhancement of other regions of the light spectrum.

For example, flowers are encouraged by larger amounts of far red light in the 650 nm to 750 nm region. This can be achieved using a far red-emitting luminescent material.

Fruits and vegetables contain carotenoids that give them distinctive colours such as the red compound, lycopene, found in tomatoes. Other carotenoids have yellow, orange and many other colours that can be seen in the range of colours of produce.

It is known that increases in particular wavelengths of light can encourage increased production of the compounds in plants that absorb those wavelengths. Red fruits can be made to be more red or even increase their size.

The greatest advantage of this technology is that it uses the sun as its only energy source.

Further advantages of the present disclosure include:
conversion of light to usable wavelengths, rather than simple filtering of lesser used wavelengths;
increased photosynthetic efficiency by conversion of light absorbed at a low level into light absorbed at a higher level;
better use of available light;
optimisation of light spectrum to better suit growth;
ability to use a single light source with a single wavelength output at an energy equal to or higher than 400 nm in conjunction with luminescent material(s) that absorb and convert this high energy monochromatic light to create the entire range of wavelengths required for growth;
light extractors for distribution of light;
improved efficiency of open systems towards the efficiency of closed systems;
utilisation of carbon dioxide from industrial and agricultural sources for photosynthesis.

Figure 6:
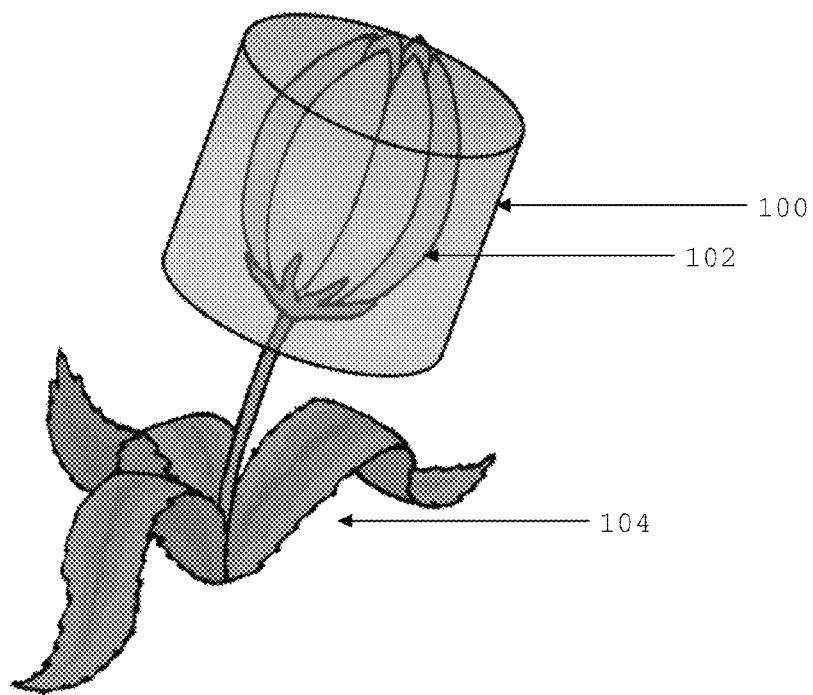
FIG. 6 is a cartoon representation of one embodiment of a surround comprising the luminescent light guide of the disclosure.

The light extractor of the disclosure or the luminescent light guide of the disclosure may be incorporated into a surround for surrounding the plant or a part thereof, the alga or the cyanobacterium. The surround acts to emit light of the second wavelength or wavelength range to an individual plant or to a part thereof, for example, a flower as shown in FIG. 6, a bud or a blossom to encourage and improve the development of fruits, vegetables, or flowers.

In one embodiment of the surround, the technology can be used for growing wine grapes, in which lighting conditions are known to be particularly important. The lighting can be customised such that the grape colour and flavour may be fine-tuned by the increase or decrease of particular flavanoids, carotenoids, polyphenols etc.

Similarly, a surround may be applied to a seaweed or to algae or cyanobacteria grown in liquid medium.

Figure 7:
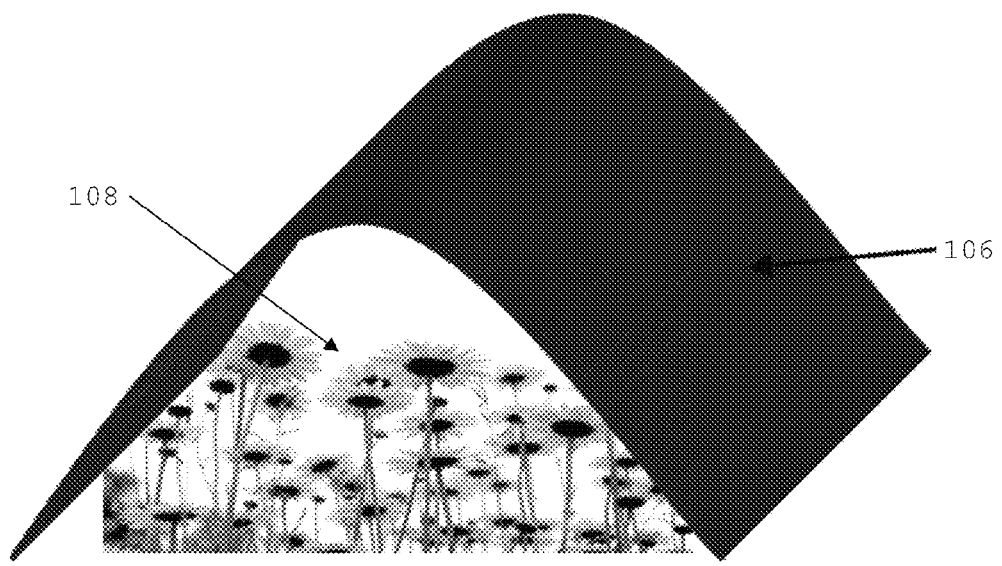
FIG. 7 is a cartoon representation of one embodiment of a cover comprising the luminescent light guide of the disclosure.

If it is desired to direct the light of the second wavelength or wavelength range to one or a plurality of plants or seaweeds, or to algae or cyanobacteria, light extractor of the disclosure or the luminescent light guide of the disclosure may be incorporated into a cover for covering the plant or a part thereof, the alga or the cyanobacterium. For example, the cover may be draped above flowers, as shown in FIG. 7, or the cover may comprise a cover for an orchard, the cover being suspended over the fruit trees.

Similarly, light extractor of the disclosure or the luminescent light guide of the disclosure, the surround, or the cover may be incorporated into a greenhouse, a terrarium, a conservatory, herbarium, arboretum, nursery, or bioreactor. A plurality of light extractors of the disclosure or luminescent light guides of the disclosure, surrounds or covers may be used. For example, in one embodiment, a bioreactor may comprise a plurality of luminescent light guides. In another embodiment of a bioreactor, a plurality of covers may be used to cover an open pond-type bioreactor. Alternatively, a plurality of covers may be used in an orchard or to cover a greenhouse.

As used herein, "algae containment apparatus" refers to any container or vessel that supports a biologically active environment in which algae or cyanobacteria grow. An "algae containment apparatus" may also be suitable to grow aquatic plants.

An "algae containment apparatus" has no predetermined length other than that dictated by factors of practical engineering and includes tubes or tubular triangular shaped bags. An "algae containment apparatus" may be rigid or flexible. In one embodiment, an "algae containment apparatus" is a substrate.

The algae containment apparatus may be flexible. The algae containment apparatus may be tubular. The cross-section of the apparatus may be any useful geometry including circular, ellipsoid, square, rectangular, parabolic, triangular or any combination thereof. The algae containment apparatus may be tubular and triangular, e.g. parabolic in cross-section, with a base positioned away from the light and a vertex positioned towards the light. The algae containment apparatus may comprise piping with intermittent holes for delivery of gases comprising carbon dioxide. The algae containment apparatus may comprise a first light guide. The luminescent material of the algae containment apparatus may emit a second wavelength in the range of about 600 nm to about 700 nm, or may emit a second wavelength range of about 600 nm to about 700 nm. The algae containment apparatus may comprise diffusion particles.

As used herein, "bioreactor" refers to any device or system larger than and/or comprising an "algae containment apparatus" that supports a biologically active environment in which plants or part thereof, algae or cyanobacteria grow. A "bioreactor" may be an open system or a closed system. Thus, a "bioreactor" may include a pond, lake or raceway. Alternatively, a "bioreactor" may be a vessel. These vessel "bioreactors" are commonly cylindrical, ranging in size from liters to cubic meters, and are often made of stainless steel. Alternatively, a "bioreactor" may be made of concrete or a polymer. To be used as a bioreactor, a carbon source, an energy source and trace nutrients are required. For plants and photosynthetic algae or cyanobacteria, a carbon source is carbon dioxide, and an energy source is light, typically sunlight.

Persons skilled in the art will appreciate that suitable bioreactors, or bioreactors that may be suitably adapted, are known.

The bioreactor may comprise a plurality of algae containment apparatuses that may be positioned side by side. The bioreactor may further comprise a second light guide positioned on the containment. The second light guide of the bioreactor may comprise a luminescent material. The luminescent material may emit light comprising the range of about 540 nm and about 600 nm. The second light guide may comprise diffusion particles. The bioreactor may be an open pond or raceway.

As used herein, the term "greenhouse" refers to a structure used to grow plants including vegetables, herbs, flowers, legumes, fruits, vines and trees. In a typical greenhouse, enclosures are constructed to contain plant growth in ideal conditions usually free of pests, viruses and fungi. These enclosures also allow for control of lighting, moisture and humidity for any given plant. Accordingly, greenhouses allow controlled and dense growth. The term "greenhouse" includes a terrarium, a conservatory, herbarium, arboretum, or nursery.

The shape of a structure disclosed herein, including but not limited to an algae containment apparatus, a bioreactor or a greenhouse, for example, may be any shape or size, provided that it serves its purpose. A bioreactor may comprise a receptacle, a container, a vessel, a tank, a bag, a sac, a chamber, a reservoir, or a pond, for example. A greenhouse may comprise any useful cross-section such as a square, a rectangle, a circle, an ellipse, a triangle, a pentagon and so on.

Also disclosed herein is a method for improving a greenhouse or a bioreactor for growing a plant or part thereof, an alga or a cyanobacterium, comprising providing the greenhouse or bioreactor with light extractor of the disclosure or the luminescent light guide of the disclosure, the surround, or the cover.

The shallow depths at which traditional open pond algal systems operate to allow sufficient exposure to sunlight require large areas to obtain adequate algal growth. Bioreactors require smaller areas and allow larger volumes of algal growth, but suffer from the problem of restricted availability of light at depth.

The present apparatus and methods overcome this limitation by increasing the solar efficiency of algae grown in the bioreactor. Thus, more algae may be grown in a smaller volume of growth medium. Furthermore, the depth of the bioreactor may be up to 10 times greater than current designs and therefore would require 10 times less land area. Most importantly, due to the optimised light spectrum in the system, algae will be able to grow at higher concentrations within the bioreactor. Additionally, fewer materials and less transparent tubing should be required compared with current bioreactors.

In the claims that follow and in the description of the invention, except where the context requires otherwise due to express language or necessary implication, the word "comprise" or variations such as "comprises" or "comprising" is used in an inclusive sense, i.e. to specify the presence of the stated features, but not to preclude the presence or addition of further features in various embodiments of the invention.

As used herein, "cyanobacterium" and "cyanobacteria" refer to the singular and plural forms of the word, respectively. "Cyanobacteria" are prokaryotic, photosynthetic organisms that are also know as blue-green algae, but are not true algae. In contrast to algae that employ chlorophyll for photosynthesis, "cyanobacteria" generally employ phycobilins to absorb light for photosynthesis. Phycobilins in "cyanobacteria" include phycoerythrin, phycocyanin and allophycocyanin. Phycobilins predominantly absorb light in the green/yellow/orange (and near red) region of the electromagnetic spectrum from about 500 nm to about 650 nm, a region that chlorophyll absorbs very poorly.

The term "dielectric" refers to a non-conducting substance.

As used herein, the term "conduit" or "light conduit" is used interchangeably with the term "light guide" and refers to any material or construct of multiple materials, solids or liquids, designed to transport light using internal reflection or total internal reflection. This internal reflection is dependant upon the indices of refraction of the materials involved where the materials are transparent or translucent. Fibre optics are the most common example of conduits, but larger systems such as sheets and columns of any unspecified width or length are also included.

As used herein, "doped" or "doping" refers to the process of intentionally introducing impurities ("dopants") into a pure material to change its optical properties, i.e. with respect to luminescence, i.e. fluorescence or phosphorescence. "Dopants" include rare-earth elements.

As used herein, "emit" or "emission" refer to discharging or issuing light energy from a luminescent material.

As used herein, the term "excite" or "excitation" refers to causing change to, or exerting influence on, the luminescent material, particularly to the absorption of light energy by the luminescent material. "Exciting" refers to charging the luminescent material by absorption of light energy in readiness for its later emission as visible light of longer wavelength.

The term "fluorescent" or "fluorescence" and the term "phosphorescent" or "phosphorescence" each refers to a class of luminescence in which energy, usually light energy, is absorbed by a material at one wavelength or within a window of wavelengths and is subsequently emitted by the material as energy of a longer wavelength, or lower energy. "Fluorescence" can be distinguished generally from "phosphorescence" based on the time scale of light emission from the material, with phosphorescence emission being longer than fluorescence, but more accurately defined by the distinct pathways in the photophysics of relaxation from light induced excited states. These photophysical differences are clearly defined and known.

As used herein, "luminescence" refers to fluorescence and/or phosphorescent.

As used herein, "emit" or "emission" refers to discharge or issuance of light energy from a luminescent material.

As used herein, the terms "absorb", "absorption", "excite" or "excitation" refers to causing change to, or exerting influence on, the luminescent material, particularly to the absorption of light energy by the luminescent material. "Absorbing" or "exciting" refers to charging the luminescent material by absorption of light energy in readiness for its later emission as visible light of longer wavelength. The term "absorption" refers to the physical process of absorbing light.

In contrast, and as used herein, "absorbance" refers to the mathematical quantity, as defined by Equation 1, of absorbed light.

As used herein, "growth medium" refers to any mixture of trace nutrients capable of sustaining growth of algae or cyanobacteria. An example of a growth medium is a solution including the following constituents (the concentration for each constituent is mg/L): $NaNO_3$, 250; $CaCl_2.2H_2O$,25; $MgSO_4.7H_2O$,75; $K_2HPO_4$, 75; $KH_2PO_4$, 175; NaCl, 25; KOH, 31; $FeSO_4.7H_2O$,5.0; $H_3BO_3$, 11.4; $ZnSO_4.7H_2O$, 8.8; $MnCl_2.4H_2O$, 1.44; $MoO_3$, 0.7; $CuSO_4.5H_2O$, 1.57; $Co[NO_3]_2.6H_2O$, 0.50 and EDTA, 50. Alternatively, a growth medium may comprise wastewater or seawater, either treated or untreated.

The term "polymer" refers to a large molecule built up by repetitive bonding of many smaller units called monomers. The term "polymer" includes both homo-polymers comprising one species of constituent monomer and co-polymers comprising more than one species of constituent monomer.

As used herein, "substrate" refers to any entity that provides a vehicle for the luminescent material and/or a growing surface for algae or cyanobacteria. Thus, in a vessel bioreactor for example, the substrate may include the walls and base of the bioreactor. In some embodiments, "substrate" refers to an entity distinct from the walls or base of the bioreactor that provides a vehicle for the luminescent material and/or growing surface for algae or cyanobacteria. In some embodiments, the algae containment apparatus or bioreactor is configured to prevent fouling of the substrate by direct contact with the algae. More than one "substrate" may be present in a bioreactor. In a particular embodiment, the "substrate" is the luminescent material.

The term "ultraviolet" or "UV" light refers to that portion of the solar electromagnetic spectrum subdivided as UVA, UVB, and UVC ranging from 400 to 100 nm.

The term "visible light" refers to that portion of the electromagnetic spectrum or photons visible to the naked eye, and is distinct from "ultraviolet" or "UV" light. This portion of the electromagnetic spectrum is typically regarded as falling between wavelengths of about 400 nm and about 750 nm.

Any luminescent material, which is capable of excitation by, or absorption of, light of a first wavelength or wavelength range and emission of visible light of a second wavelength or wavelength range longer than that of the first wavelength or wavelength range, can be used according to the present disclosure, provided that the emitted light is suitable for growing algae or cyanobacteria. In particular, light of the second wavelength or wavelength range should be absorbable by algae or cyanobacteria photosynthetic proteins or pigments, including chlorophyll a, chlorophyll b, chlorophyll c, and phycobilins such as phycoerythrin, phycocyanin and allophycocyanin.

The main characteristic driving selection of a luminescent material to be used is the emission wavelength of the material.

The luminescent material should be selected on the basis of the desire type of luminescence, i.e., fluorescence or phosphorescence.

Quantum efficiency may also be a characteristic driving selection of a luminescent material. Quantum efficiency should be of a magnitude sufficient to produce visible light suitable for photosynthesis.

The luminescent material should absorb light in the green region of the electromagnetic spectrum (about 500 nm to about 600 nm), a part of the spectrum largely unused by the chlorophyll pigments in algae. The luminescent material will absorb and use this energy to luminesce, or emit, red light between about 600 nm and about 700 nm, in one embodiment near 650 nm, which the algae can use extremely well for photosynthesis, and therefore growth.

The luminescent material may also exploit chlorophyll's absorbance peak in the electromagnetic spectrum near 420 nm. In this instance, the luminescent material should absorb UV radiation in the range of about 250 nm to about 400 nm and emit visible light in the region of about 400 nm to about 500 nm, in one embodiment near 420 nm, where such light is also used for photosynthesis.

In some embodiments, the luminescent material will absorb light from the UV and/or blue region, generally from about 250 nm to about 500 nm, and emit light in the green, yellow, orange or red region, generally from about 500 nm to about 650 nm, which may be then be absorbed by phycobilins of cyanobacteria and used for photosynthesis.

In one embodiment, more than one luminescent material may be present. For example, use of two luminescent materials, one that absorbs UV light and luminesces blue light and the other that absorbs green light and luminesces red light enables much more of the total solar spectrum to be used for photosynthesis in algae. Thus, the disclosure allows use of nearly all of the solar spectrum for photosynthesis, except for the infrared (IR) portion, although the IR portion may be used in cold climes for maintaining algal growth.

A luminescent material includes quite generally all inorganic, organic and organometallic materials capable of converting an input of absorbed photons into an output of photons of different energy, and the output comprises a visible light with a brightness and intensity sufficient for photosynthesis. The luminescent material may be coated on the substrate and/or may be disposed in or contained in the substrate.

In one embodiment, the luminescent material may be any inorganic luminescent compound. In one embodiment, the inorganic luminescent compound may comprise a rare-earth doped inorganic crystal or a doped zinc sulphide. In another embodiment, the luminescent material may be any organic luminescent compound. In yet another embodiment, the luminescent material may comprise a quantum dot. In one embodiment, the luminescent material may be any organometallic luminescent compound.

The luminescent material may be, for example, a commercially available luminescent pigment or luminescent dye.

Examples of the luminescent (phosphorescent) material used include, but are not limited to, calcium sulfate phosphors (host crystal: CaS; activator: Bi); zinc sulfate phosphors (host crystal: ZnS; activator: Cu, e.g. "GSS" manufactured by Nemoto & Co., Ltd.); strontium aluminate or calcium aluminate phosphors (host crystal: strontium aluminate or calcium aluminate; activator: Eu, Dy, Nd, or the like; e.g. VGS-FAP or VGS3-FAP series manufactured by Visionglow International Pty Ltd; LumiNova® G-300 series, BG-300 series, and V-300 series, manufactured by Nemoto & Co., Ltd.; "ULTRA GLOW series" NP-2810, NP-2820, and NP-2830, manufactured by Nichia Corporation; "R-bright" B and YG, manufactured by Lead Co., Ltd.; "Chemibright Powder" G-40-C, G-100-B, G-100-C, GB-80-B, and B-50-B, manufactured by Lumica Corporation); phosphors containing CaSrS, as a host crystal, and Bi, as an activator; and phosphors containing CaS, as a host crystal, and Eu or Tm, as an activator. Examples of suitable phosphorescent materials also include yttrium aluminium garnet (YAG, $Y_3Al_5O_{12}$), terbium aluminium garnet (TAG, $Tb_3Al_5O_{12}$), and Zex, which can emit a yellow light having a wavelength in the range of 530 to 590 nm.

Examples of the luminescent (phosphorescent) material used include, but are not limited to, calcium sulfate phosphors (host crystal: CaS; activator: Bi); zinc sulfate phosphors (host crystal: ZnS; activator: Cu, e.g. "GSS" manufactured by Nemoto & Co., Ltd.); strontium aluminate or calcium aluminate phosphors (host crystal: strontium aluminate or calcium aluminate; activator: Eu, Dy, Nd, or the like; e.g. VGS-FAP or VGS3-FAP series manufactured by Visionglow International Pty Ltd; LUMINOVA® G-300 series, BG-300 series, and V-300 series, manufactured by Nemoto & Co., Ltd.; "ULTRA GLOW series" NP-2810, NP-2820, and NP-2830, manufactured by Nichia Corporation; "R-bright" B and YG, manufactured by Lead Co., Ltd.; "Chemibright Powder" G-40-C, G-100-B, G-100-C, GB-80-B, and B-50-B, manufactured by Lumica Corporation); phosphors containing CaSrS, as a host crystal, and Bi, as an activator; and phosphors containing CaS, as a host crystal, and Eu or Tm, as an activator. Examples of suitable phosphorescent materials also include yttrium aluminium garnet (YAG, $Y_3Al_5O_{12}$), terbium aluminium garnet (TAG, $Tb_3Al_5O_{12}$), and Zex, which can emit a yellow light having a wavelength in the range of 530 to 590 nm.

If the structure of the fluorescent material has the stilbene moiety, or the distyrylbiphenyl moiety, any chromophore groups, such as methoxyphenyl group, anthracene group, pyrene group, or 9,10-anthraquinone group, can be symmetrically bonded to such a stilbene moiety or distyrylbiphenyl moiety for enhancing brightness. Examples of such fluorescent materials include, but are not limited to, 4,4'-bis(2-methoxystyryl)biphenyl, 4,4'-bis{2-(9-anthracenyl) ethylenyl}biphenyl, 4,4'-bis(2-(1-yrenyl) ethylenyl) biphenyl, and 4,4'-bis(2-(1-anthraquinonyl)ethylenyl) biphenyl. When 4,4'-bis(2-methoxystyryl)biphenyl is used as the fluorescent material, it can be excited by UV light and subsequently emits a blue light having a wavelength between 450 nm and 490 nm. When 4,4'-bis{2-(9-anthracenyl) ethylenyl}biphenyl is used as the fluorescent material, it can be excited by UV light and subsequently emits a yellowish-green light having a wavelength between 520 nm and 550 nm. When 4,4'-bis{2-(1-pyrenyl)ethylenyl}biphenyl is used as the fluorescent material, it can be excited by UV light and subsequently emits a blue light having a wavelength between 450 nm and 490 nm. When 4,4'-bis{2-(1-anthraquinonyl) ethylenyl}biphenyl is used as the fluorescent material, it can be excited by UV light and subsequently emits a red light having a wavelength between 580 nm and 660 nm. In order to increase the brightness, a blue phosphor may be used with 4,4'-bis(2-methoxystyryl)biphenyl, or 4,4'-bis{2-(1-pyrenyl) ethylenyl}biphenyl to convert the emission to a blue light; a yellowish green phosphor may be used with 4,4'-bis{2-(9-anthracenyl)ethylenyl}biphenyl to convert the emission to a yellowish green light; and a red phosphor may be used with 4,4'-bis{2-(1-anthraquinonyl)ethylenyl}biphenyl to convert the emission to a red light.

The particle size of the luminescent material embedded in the substrate is not particularly limited, though it may comprise particles with an average diameter of 10 nm to 10 μm. If the luminescent material has an average particle diameter below 10 nm, it exhibits poor durability and significantly decreased brightness. If the luminescent material has an average particle diameter above 10 μm, greater visible light scattering arises. In the case of non-mineral luminescent materials that do not depend on a crystal lattice for their luminescent processes, as in most fluorescent dyes, the material can be fully dispersed or dissolved into the substrate as individual molecules absorbing light and subsequently luminescing.

Any lighting source that emits light of a wavelength that is suitable for energising the luminescent material may be used as an energy source. The source may be the sun, an incandescent device, a halogen device, or a fluorescent device. The device may be fluorescent such as bulb, globe or tube. In some embodiments, light is derived from sunlight.

The luminescent material may absorb light prior to algal absorption of light, since algal growth may impede absorbance of light by the luminescent material. The luminescent material may possess an emission period of sufficient duration to enable optimal algal absorption prior to abatement of the luminescence.

Any lighting source that emits light of a wavelength that is suitable for energising the luminescent material may be used as an energy source. The energy source may be solar or artificial. The artificial light source may be an incandescent device, a halogen device, or a fluorescent device. The device may be fluorescent such as bulb, globe or tube.

In one embodiment, the artificial energy source may be a low energy UV fluorescent bulb, often known as a "black light" that has a single emission peak near 370 nm. The luminescent growing apparatus may comprise one layer with a mixture of luminescent materials or individual layers with each luminescent material separately disposed. The luminescent materials absorb well the 370 nm light from the black light and may provide emission peaks in the blue, red and/or any other desired wavelength ranges for optimal plant growth. The luminescent growing apparatus may contain multiple light extractors that allow the emitted light to be dispersed.

In some embodiments, the luminescent material is disposed in or coated on a substrate. Thus, the substrate may emit light to the algae or cyanobacteria.

Algae or cyanobacteria may grow on a surface. The surface may be provided by the luminescent material. Alternatively, the surface may be provided by a substrate.

The substrate may be any shape that is amenable to exposure to light and provides a surface for growth of algae. Thus, shape selection will largely be driven by these considerations.

The substrate may be regular or irregular in shape. The dimensions may be equal or unequal and may or may not be in proportion. The substrate may be solid, hollow, porous, or laminar, for example. The substrate may comprise more than one material.

If more than one substrate is present, the substrates need not be homogenous; the substrates may include any combination of shapes or sizes or compositions of individual substrates.

The main characteristics driving selection of a substrate to be used according to the disclosure include high surface area, transmission of UV light, stable to sunlight or UV light, approximate neutral buoyancy in water, and durability.

The substrates may be arranged in close proximity to enable high concentrations of algae to be grown in relatively small volumes. The substrates may be arranged as closely packed layers or in an array. Alternatively, the substrates may not be in any fixed orientation and may circulate through the bioreactor randomly. The substrate may be a whole continuous surface or freely moving pieces of any range of sizes, shapes or composition. The substrates may be circulated by any appropriate mechanism that allows exposure to a fixed light source, such as sunlight or conduits, for example. Circulation may be achieved by bubbler, injector, pump, blade, impeller, jet, nozzle, stirrer, or shaker, for example.

The substrate may comprise a dielectric material. The dielectric material may comprise a polymer, glass, or quartz. In one embodiment, the polymer comprises acrylate or polycarbonate. In one embodiment, the polymer is polymethyl methacrylate or polycarbonate. In one embodiment, the polymer is polymethyl methacrylate.

In one embodiment, the luminescent material is disposed in a polymer. In another embodiment, the luminescent material is coated on a polymer substrate. The polymer may comprise: an acrylic, a urethane; an ester; a methacrylate; a thiophene; a co-polymer of any bond conjugated polymer; a light transparent polymer; a low ultra violet absorbent polymer; a heat conducting polymer; or an electrically conducting polymer. In another embodiment, the polymer may be: aniline based; pyrrole based; acetylene based; or furan based.

In another embodiment, the polymer may comprise polyurethane, polyester, polyamide, polyurea, polycarbonate and polymethyl methacrylate. The constituent monomers in the polymers of the present disclosure may be methacrylate-based, carbonate-based, acrylamide-based, methacrylamide-based, or styrene-based monomers.

Constituent monomers of the vinyl polymers that may be used include acrylic esters, specifically, e.g., methyl acrylate, ethyl acrylate, n-propyl acrylate, isopropyl acrylate, n-butyl acrylate, isobutyl acrylate, sec-butyl acrylate, tert-butyl acrylate, amyl acrylate, hexyl acrylate, 2-ethylhexyl acrylate, octyl acrylate, tert-octyl acrylate, 2-chloroethyl acrylate, 2-bromoethyl acrylate, 4-chlorobutyl acrylate, cyanoethyl acrylate, 2-acetoxyethyl acrylate, dimethylaminoethyl acrylate, benzyl acrylate, methoxybenzyl acrylate, 2-chlorocyclohexyl acrylate, cyclohexyl acrylate, furfuryl acrylate, tetrahydrofurfuryl acrylate, phenyl acrylate, 5-hydroxypentyl acrylate, 2-methoxyethyl acrylate, 3-methoxybutyl acrylate, 2-ethoxybutyl acrylate, 2-ethoxyethyl acrylate, 2-isopropoxy acrylate, 2-butoxyethyl acrylate, 2-(2-methoxyethoxy)ethyl acrylate, 2-(2-methoxyethoxy)ethyl acrylate, 2-(2-butoxyethoxy) ethyl acrylate, ω-methoxypolyethylene glycol acrylate (addition mol number: 9), 1-bromo-2-methoxyethyl acrylate, and 1,1-dichloro-2-ethoxyethyl acrylate.

In addition, the following monomers can be used. Methacrylic esters, specifically, e.g., methyl methacrylate, ethyl methacrylate, n-propyl methacrylate, isopropyl methacrylate, n-butyl methacrylate, isobutyl methacrylate, sec-butyl-methacrylate, tert-butylmethacrylate, amylmethacrylate, hexylmethacrylate, cyclohexylmethacrylate, benzyl methacrylate, chlorobenzyl methacrylate, octyl methacrylate, stearylmethacrylate, sulfopropylmethacrylate, N-ethyl-N-phenylaminoethyl methacrylate, 2-(3-phenylpropyloxy) ethyl methacrylate, dimethylaminophenoxyethyl methacrylate, furfuryl methacrylate, tetrahydrofurfuryl methacrylate, phenyl methacrylate, cresyl methacrylate, naphthyl methacrylate, 2-hydroxyethyl methacrylate, 4-hydroxybutyl methacrylate, triethylene glycol monomethacrylate, dipropylene glycol monomethacrylate, 2-methoxyethyl methacrylate, 3-methoxybutyl methacrylate, 2-acetoxyethyl methacrylate, 2-acetoacetoxyethyl methacrylate, 2-ethoxyethyl methacrylate, 2-isopropoxyethyl methacrylate, 2-butoxyethyl methacrylate, 2-(2-methoxyethoxy)ethyl methacrylate, 2-(2-ethoxyethoxy)ethyl methacrylate, 2-(2-butoxyethoxy) ethyl methacrylate, ω-methoxypolyethylene glycol methacrylate (addition mol number: 6), acryl methacrylate, and methacrylic acid dimethylaminoethylmethyl chloride salt can be exemplified.

Vinylesters, specifically, e.g., vinylacetate, vinyl propionate, vinyl butyrate, vinyl isobutyrate, vinyl caproate, vinyl chloroacetate, vinylmethoxy acetate, vinylphenyl acetate, vinyl benzoate and vinyl salicylate can be exemplified.

Acrylamides, e.g., acrylamide, methylacrylamide, ethylacrylamide, propylacrylamide, isopropylacrylamide, n-butylacrylamide, sec-butylacrylamide, tert-butylacrylamide, cyclohexylacrylamide, benzylacrylamide, hydroxymethylacrylamide, methoxyethylacrylamide, dimethylaminoethylacrylamide, phenylacrylamide, dimethylacrylamide, diethylacrylamide, β-cyanoethylacrylamide, N-(2-acetoacetoxyethyl)acrylamide, and diacetoneacrylamide can be exemplified.

Methacrylamides, e.g., methacrylamide, methylmethacrylamide, ethylmethacrylamide, propylmethacrylamide, isopropylmethacrylamide, n-butylmethacrylamide, sec-butylmethacrylamide, tert-butylmethacrylamide, cyclohexylmethacrylamide, benzylmethacrylamide, hydroxymethacrylamide, chlorobenzylmethacrylamide, octylmethacrylamide, stearylmethacrylamide, sulfopropylmethacrylamide, N-ethyl-N-phenylaminoethylmethacrylamide, 2-(3-phenylpropyloxy)ethylmethacrylamide, dimethylaminophenoxyethylmethacrylamide, furfurylmethacrylamide, tetrahydrofurfurylmethacrylamide, phenylmethacrylamide, cresylmethacrylamide, naphthylmethacrylamide, 2-hydroxyethylmethacrylamide. 4-hydroxybutylmethacrylamide, triethylene glycol monomethacrylamide, dipropylene glycol monomethacrylamide, 2-methoxyethylmethacrylamide, 3-methoxybutylmethacrylamide, 2-acetoxyethylmethacrylamide, 2-acetoacetoxyethylmethacrylamide, 2-ethoxyethylmethacrylamide, 2-isopropoxyethylmethacrylamide, 2-butoxyethylmethacrylamide, 2-(2-methoxyethoxy) ethylmethacrylamide, 2-(2-ethoxyethoxy) ethylmethacrylamide, 2-(2-butoxyethoxy) ethylmethacrylamide, ω-methoxypolyethylene glycol methacrylamide (addition mol number: 6), acrylmethacrylamide, dimethylaminomethacrylamide, diethylaminomethacrylamide, B-cyanoethylmethacrylamide, and N-(2-acetoacetoxyethyl)methacrylamide can be exemplified.

Olefins, e.g., dicyclopentadiene, ethylene, propylene, 1-butene, 1-pentene, vinyl chloride, vinylidene chloride, isoprene, chloroprene, butadiene, and 2,3-dimethylbutadiene can be exemplified.

Styrenes, e.g., styrene, methylstyrene, dimethylstyrene, trimethylstyrene, ethylstyrene, isopropylstyrene, chloromethylstyrene, methoxystyrene, acetoxystyrene, chlorostyrene, dichlorostyrene, bromostyrene, and vinylbenzoic acid methyl ester can be exemplified.

Vinyl ethers, e.g., methylvinyl ether, butylvinyl ether, hexylvinyl ether, methoxyethylvinyl ether and dimethylaminoethylvinyl ether can be exemplified.

As other examples, e.g., butyl crotonate, hexyl crotonate, dibutyl itaconate, dimethyl maleate, dibutyl maleate, dimethyl fumarate, dibutyl fumarate, methyl vinyl ketone, phenyl vinyl ketone, methoxyethyl vinyl ketone, glycidyl acrylate, glycidyl methacrylate, N-vinyloxazolidone, N-vinylpyrrolidone, acrylonitrile, methacrylonitrile, methylene moronnitrile, and vinylidene can be exemplified.

Two or more monomers may be used as co-monomers with each other according to purposes (e.g., improvement of hardness, flexibility, tensile strength and light fastness), thereby producing co-polymers.

The methods of adding and mixing the components with a polymer are not restricted. For example, methods of thoroughly mixing the powders, flakes or pellets of translucent polymers with the above components and then melt-mixing by an extruder may be used. In translucent thermoplastic polymers, methods of adding the above components to unhardened liquid state starting materials and thoroughly mixing and dispersing may be used. At this time, generally used additives, e.g., a thermal stabiliser, an antioxidant, a mould releasing agent, an antistatic agent, and a flame retarder may be added. Moulding may be performed according to ordinary methods. That is, in the case of thermoplastic polymers, covered pipes can be produced by a melt-extrusion method, shrink tubes can be produced by stretching and quenching of the pipes obtained by melt-extrusion, and covers can be produced by injection moulding, extrusion moulding and, if necessary, vacuum moulding. In the case of thermo-setting polymers, cast moulding is advantageous.

In one embodiment, sunlight can be introduced into the bioreactor by collection, diversion of IR light, and distribution using a parabolic dish, a prism, and light conduits, respectively. Parabolic dishes ensure efficient collection of solar energy without loss by reflection that occurs commonly off the surface of water in open pond systems. This arrangement should ensure the most efficient collection of solar energy without loss by reflection that occurs commonly off the surface of water in open pond systems. Once diverted, the IR portion of the collected energy can be used as a source of solar thermal energy.

In one embodiment, the solar collecting dish can be fitted with UV and IR filters to exclude damaging UV and heating radiation. However, if it is desired to raise the temperature of the medium in which the algae are growing, the IR filter may be removed to harness the IR radiation until the water is at the optimal temperature for growth of the algae.

Alternatively, a Fresnel lens, a mirror or a combination of mirrors can be used to collect light. Fresnel lenses are, at their simplest, glass or plastic sheets with finely scored lines or ridges formed in the sheets. They can be flat or formed with a curvature to provide greater focus into the bioreactor. Also contemplated is a bank or storage cell comprising a further source of luminescent material that can be charged during daylight hours and used during the night to sustain a low level of algae growth.

After collection and diversion of IR energy, light may be distributed using conduits known in the art. Such conduits allow deeper penetration of light into the bioreactor and increase the surface area from which light is emitted for photosynthesis.

A light conduit or light guide may be solid or hollow. A solid light conduit may include an optical fibre. A hollow light conduit may be filled with a liquid. Liquid-filled light conduits are known in the art, for example as disclosed in U.S. Pat. No. 4,927,231, U.S. Pat. No. 5,857,052, and U.S. Pat. No. 6,507,688.

A light conduit known in the art may be scaled up for use in the bioreactor.

A light conduit known in the art may be modified, for example, to distribute light along its length in addition to transporting light from one end of the conduit to the other. For example, a translucent light guide may be etched to aid diffusion of light from the light conduit. In addition, the light guide may comprise a diffusing device, for example as disclosed in U.S. Pat. No. 4,420,796.

A light conduit, for example a liquid-filled light guide may comprise a double wall. A liquid-filled light-guide may comprise a plastic outer wall and a plastic inner wall, the walls being spaced apart and filled with air, vacuum, or any number of transparent materials of a lower index of refraction than the inner liquid. Alternatively, the cavity formed between the spaced-apart walls may be filled with a gas, for example an inert gas such as nitrogen, carbon dioxide or argon as found in U.S. Pat. No. 4,420,796. In such a light conduit, the air or other gas provides an appropriate refractive index to guide light in the conduit.

A liquid used in the light conduit may comprise any liquid suitable for conducting light, such as water, dimethylsulfoxide or ethylene glycol. The liquid may comprise a salt solution.

The light guide or light conduit may be angled to make best use of seasonal solar incident light. For example, the light conduit may be angled at about 70° relative to the ground to ensure internal reflection during winter at latitudes near 37° North or South where the indices of refraction of water, $n=1.33$, and air, $n=\sim1$, define the system's ability to transport sunlight in the conduit and the lowest solar angle is approximately 30° relative to the horizon.

In one embodiment, the surface area of the light collecting dish is compared to the surface area of the light conduit. For example, if the area of sunlight captured by a solar collector is 7 $m^2$, the internal surface area of the light conduit may be measured as the internal circumference of the conduit multiplied by its length; for example, a light conduit 0.25 m in diameter and 9 m long will have a surface area of approximately 7 $m^2$, similar to the collecting dish above. Thus, a light conduit of these measurements may emit light along its length at an equal light intensity as the sunlight incident on the dish neglecting losses in the process of reflection. In another example, a light conduit 0.25 m in diameter and 18 m in length will emit light along its length at about half the light intensity of the sunlight incident on the collecting dish neglecting losses in the process of reflection.

Optimal growth rates for algae occur between 200 to 600 ft-c or 2,000 to 6,000 lux (1 ft-c=~10 lux) and growth decreases with higher or lower light intensities. Strong midday sunlight is around 100,000 lux with a lower end of 32,000 lux. The light intensities of the sun are about 5 to 17 times greater than necessary for maximal algae growth. This means that the surface area of the light conduit in one embodiment may be much greater than the area of the light collecting dish. However, in practice, the intensity of light in the conduit may fall off sharply moving from the surface of the light conduit towards the inner wall of the bioreactor. In practice, a light conduit that has at least 3 to 4 times the surface area of the collecting dish should emit sufficient light for optimal algae growth. Thus, relative to the embodiment above, the light conduit may be 0.35 m in diameter and 30 m in length.

In another embodiment, the light guide is a large sheet. For example a 7 m² collector dish can connected to a light guide sheet that is 4 m by 3.5 m and emit light evenly on both sides for a total surface area of 28 m² and would thus be four times the surface area of the collector dish.

In another embodiment, the light guide is of the design developed by 3M™ and others known as a "prismatic light guide". This type of light guide has the advantage of being made within a large range of widths where the internal space of the light guide is filled with air, gas, or vacuum. The external walls are comprised of a material with a high index of refraction such as any plastic, polymer, or liquid as those described herein for general light guides. The external walls are comprised of a ridged linear pattern that creates a 90° prismatic shape that is sometimes altered to smaller angles for different light transport effects. This type of light guide offers a wide path-length for light to be guided that is comprised of mostly air that is between the prismatic layers. As with other transparent light guides, the source light must be provided to the edge or end of the prismatic light guide at a narrow range of angles.

Disclosed herein is a prismatic light guide where the prismatic layers are disposed with a luminescent material, thus combining the function of a luminescent light guide with that of a prismatic light guide. Light may enter the prismatic luminescent light guide along its length and at any angle. The luminescence generated by the luminescent material in the polymer layer is then guided by total internal reflection in the manner which the prismatic edges are designed as described in the art.

"Luminescent light guides" are light guides that function by disposing a luminescent material in a material of high refractive index such that the luminesced light becomes trapped within the material and is guided by total internal reflection.

The advantage that luminescent light guides provide over (transparent) light guides is the ability to use a light source from any given angle or entry point into the luminescent light guide, because luminescent light guides absorb light across the face or edge of the light guide, at any incident angle, at particular wavelengths of light depending on the absorption spectrum of the luminescent material.

Transparent light guides require that the light to be guided must be introduced into the light guide at the edge, for a sheet geometry, or end of the light guide. Only those photons of light that travel into the light guide at or below the critical angle for total internal reflection will be guided rather than simply pass through. Light guides are effective for conduction of light only from concentrated sources and with small ranges of angles, i.e. fibre optic cables. The broad and constantly shifting angles of natural sunlight make solar light guides difficult to design without very wide entry points and tracking systems.

Sunlight may be concentrated into sharper rays by the use of Fresnel lenses, mirrors or other optical techniques which all add to the cost of such designs. These concentrator techniques often fail to reduce the range of angles in the concentrated light so much of the light will still escape the light guide despite these efforts.

Though luminescent light guides circumvent some of the optical limitations of simple transparent light guides, they still exhibit inherent energy losses due to the down conversion of the absorbed light to the lower energy emission and losses to angles beyond the critical angle, known as the "escape cone". It is therefore expected that a square shaped a luminescent light guide manufactured from polymethyl methacrylate, for example, will emit approximately 13% of the luminesced light from each of the four edges as a best case scenario. However, this is not the case when the area covered by the luminescent light guide becomes large in comparison to its thickness.

There are significant losses due to re-absorption of the luminesced light by the luminescent material where there is an overlap between the absorbance bands of the luminescent material and the emission bands.

The absorbance (A) is dependent on the inherent absorbance of the luminescent material at each wavelength, or extinction coefficient ($\in$), its concentration in the polymer matrix (c) and the path length of incident light(b) as the Beer-Lambert law dictates:

$$A = \in (b)(c) \qquad \text{Eq. 1}$$

When the luminesced light travels through the luminescent light guide to its edges, the luminesced light experiences the same luminescent material concentration (c) and values of $\in$, but over a much longer path length than the incident light experiences. This leads to a large degree of re-absorbance of luminescence by the luminescent material.

This also selectively downshifts the emission to the lower end of the emission spectrum that is free from absorption overlap. The result is greatly reduced emission intensities with a colour that is largely red-shifted.

For many luminescent light guides there is a critical size from which any further increase to the surface area does not increase the light emitted from its edges due to these re-absorption affects which increase greatly with increasing path-lengths.

Therefore, there is a need for an improved luminescent light guide.

Disclosed herein is a light extractor comprising a luminescent material or substrate comprising a luminescent material.

The light extractor may alter the light spectrum, from any given source, by luminescence to simultaneously filter wavelengths absorbed by the luminescent material and enhance wavelengths emitted by the luminescent material.

The light extractor may alter the light spectrum, from any given source, by luminescence to simultaneously filter wavelengths absorbed by the luminescent material and enhance wavelengths emitted by the luminescent material.

The light extractor may comprise a prismatic geometry. The light extractor may selectively extract light out of one side or more than one side of the luminescent material or substrate comprising a luminescent material. The light extractors may be engineered to control the angle and direction in which the light is extracted.

The light extractor may alter the light spectrum, from any given source, by luminescence to simultaneously filter wavelengths absorbed by the luminescent material and enhance wavelengths emitted by the luminescent material.

Also disclosed is a luminescent light guide comprising a first substrate comprising a luminescent material and a light extractor.

In one embodiment, the luminescent light guide further comprises a second substrate lacking a luminescent material and of sufficient refractive index that luminescence emitted from the first substrate is guided by the first and second substrates.

In another embodiment, the first substrate comprises a light extractor of the disclosure. The light extractor may comprise a prismatic geometry, in which case the luminescent light guide comprises a prismatic luminescent light guide.

In another embodiment, the second substrate is air, gas or vacuum.

In one embodiment, the luminescent light guide comprises a photovoltaic material, wherein luminescence is guided to the photovoltaic material.

Also disclosed is a bioreactor for growing a plant or part thereof, an alga or a cyanobacterium, the bioreactor comprising a light extractor or a luminescent light guide of the disclosure.

Also disclosed is a method for guiding light, comprising illuminating the luminescent light guide of the disclosure.

Also disclosed is a method for growing a plant or part thereof, an alga or a cyanobacterium, the method comprising growing the plant or part thereof, alga or cyanobacterium in light comprising luminescence emitted by the light extractor of the disclosure, or the luminescent light guide of the disclosure, or growing the plant or part thereof, alga or cyanobacterium in the bioreactor of the disclosure.

Also disclosed is a method for generating electricity, the method comprising guiding light comprising luminescence emitted by the luminescent light guide of the disclosure to a photovoltaic material.

Also disclosed is an optical device for photography comprising the light extractor of the disclosure.

Also disclosed is a method for reducing an intensity of a wavelength absorbed by a luminescent material and simultaneously emitting luminescence, comprising illuminating with the wavelength absorbed by the luminescent material the light extractor of the disclosure.

Disclosed herein is a luminescent light guide for improving the growth of plants, algae or cyanobacteria, by improving the distribution of available light and altering the spectrum of available light to be more optimal for growth of the desired organism. The light guide may also be used for photovoltaics, providing indoor illumination and altering the spectrum of available light for lighting in any number of applications such as photography. Also disclosed are methods for manufacturing the luminescent light guide, and for growing plants, algae or cyanobacteria using the luminescent light guide. The luminescent light guide comprises a design that overcomes some of the efficiency losses and limitations when applied to larger scale designs.

Also disclosed is a method of manufacturing a light extractor comprising forming in a first substrate comprising a luminescent material a three dimensional shape that extracts light from the first substrate.

Also disclosed is a light extractor manufactured by the above method.

Also disclosed is a method of manufacturing a luminescent light guide comprising: combining a first substrate comprising a luminescent material with a second substrate lacking a luminescent material and of sufficient refractive index that luminescence emitted from the first substrate is guided by the first and second substrates; or forming a light extractor in a first substrate comprising a luminescent material.

Also disclosed is a luminescent light guide manufactured by the above method.

Also disclosed is use of a first substrate comprising a luminescent material and: —a second substrate lacking a luminescent material, and of sufficient refractive index that luminescence emitted from the first substrate is guided by the first and second substrates; or—a light extractor comprised in the first substrate, as a luminescent light guide.

Also disclosed is use of the disclosed light extractor, or the disclosed luminescent light guide for growing a plant or part thereof, an alga or a cyanobacterium.

Also disclosed is use of the disclosed luminescent light guide for generating electricity.

Also disclosed is use of the disclosed luminescent light guide for guiding sunlight. In one embodiment, the guided sunlight may be used to illuminate a room in a building.

Figure 20:
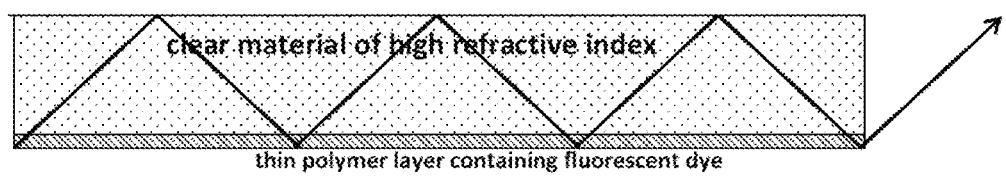
FIG. 20 is a representation of a luminescent light guide of the disclosure with a single layer of polymer comprising a luminescent material and a much thicker solution of liquid or other transparent material of high refractive index. The black line represents the path of light guided by total internal reflection. The light would travel almost entirely through clear material and spend very little of its journey passing through the polymer where re-absorption can occur.
Figure 21:
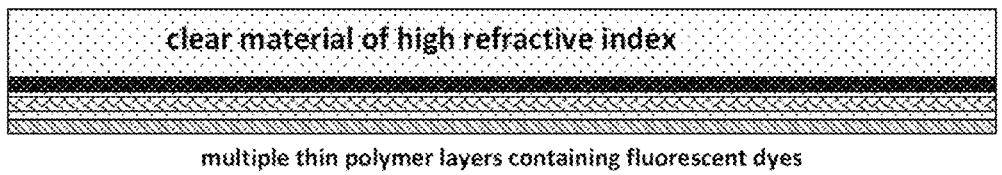
FIG. 21 is a representation of a luminescent light guide of the disclosure with multiple polymer layers each comprising a luminescent material within a thicker clear layer of high refractive index.
Figure 22:
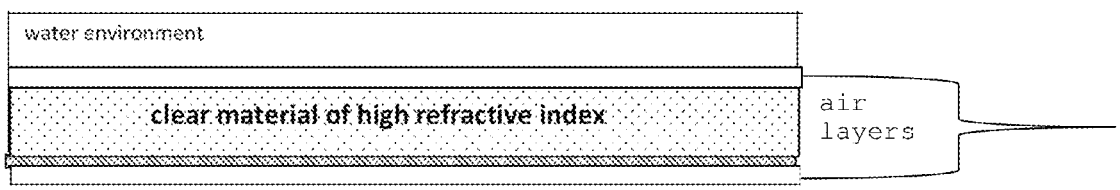
FIG. 22 is a representation of a luminescent light guide of the disclosure placed in water and the air to luminescent light guide interface is created by air layers above and below the luminescent light guide.

The thickness of the luminescent light guide can be increased by using less expensive materials or liquids of high refractive index (FIGS. 20 to 22). Ideally, the additional material should have an equally high refractive index as the thin polymer layer containing the luminescent material. Less expensive materials with lower refractive indices can also be used but with less improvement. In such a design, the luminesced light would travel to the edges of the luminescent light guide through a mostly clear medium.

As a typical example of such a technique, a 5 mm luminescent light guide, in which a luminescent material is disposed, is encased within a layer of a clear medium with an equally high refractive index that is 100 mm thick. In such a design the luminesced light escapes into the clear medium, but is guided by total internal reflection at the air interface. The luminesced light can be guided to the edges without large re-absorption losses.

Figure 9:
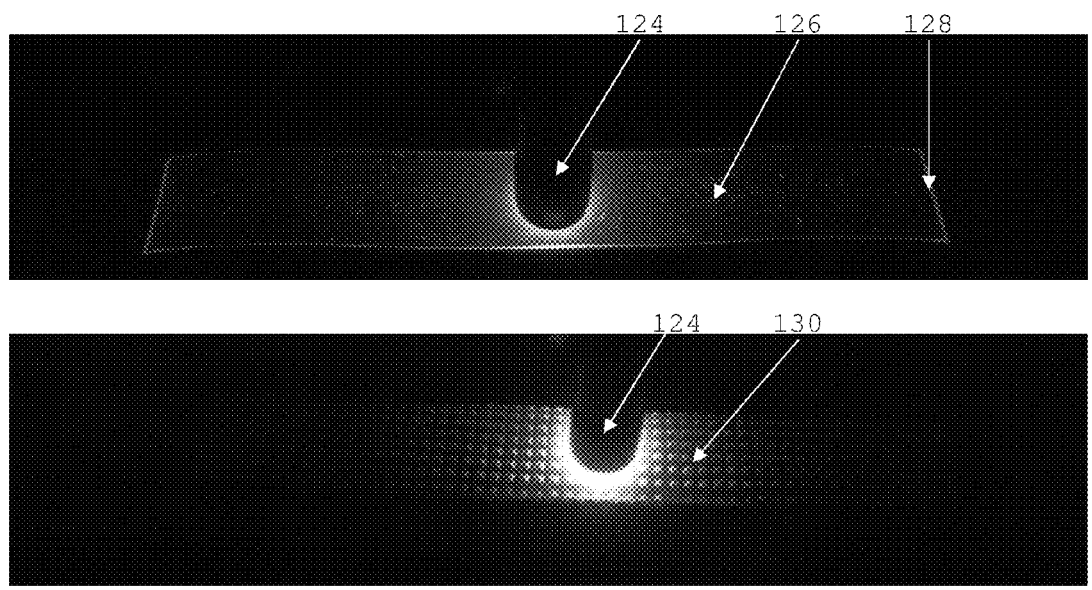
FIG. 9 are photographs illustrating light guidance in a luminescent material lacking light extractors (upper) and comprising light extractors (lower).
Figure 10:
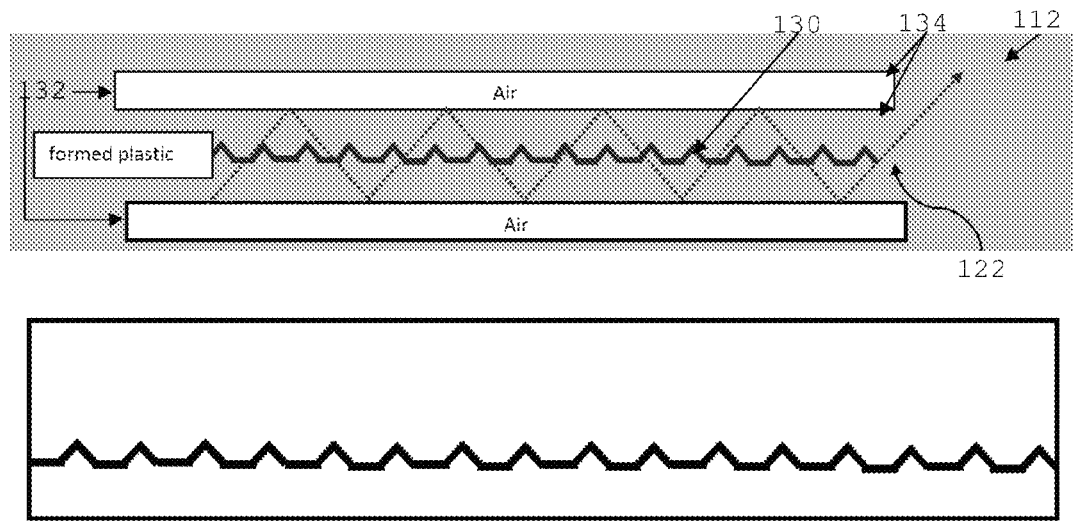
FIG. 10 is a cross-sectional representation of a luminescent light guide of the disclosure comprising light extractors (a formed plastic) positioned between layers of air (upper) and a thin polymer layer in a water filled luminescent light guide with light extractors that extract light that does not escape into the water (lower).

As can be seen in FIG. 20, light travels almost entirely through clear material and spends very little of its journey passing through the polymer where re-absorption can occur.

Where the second material has a lower index of refraction than the first material, only a fraction of the light is guided by both materials while some light remains trapped in the first material and may still experience losses to re-absorption. In order to minimise this long range trapping and loss, the luminescent material or the substrate in which the luminescent material is disposed in or coated on may comprise a light extractor, wherein the light extractor provides an escape route for light of the second wavelength or wavelength range from the luminescent material and inhibits guidance of light of the second wavelength or wavelength range by the luminescent material over distances long enough to cause re-absorption losses (FIGS. 9 and 10). The light extractor may comprise an indentation, a projection, a protrusion, a fissure, a crack, a protuberance, a boss, a knob, a lump, a hump, a lug, a peg, a prong, a rib, a ridge, a groove, a trough, a channel, a corrugation, a lip, a sawtooth, a ramp, a wedge, a texture, or may be a three dimensional prism such as pyramidal, cuboid, or any other three-dimensional prism derived from a sphere, a hemisphere, a segment, a circle, an ellipse, a triangle, a square, a parallelogram, a pentagon, a hexagon, a heptagon, an octagon and so on. The light extractor may be formed by a point indentation, or a cross-shaped indentation.

The light extractors function by creating sharp angles in the luminescent material or substrate that is beyond the tolerance of the light guide to guide light, i.e. the curvature exceeds the maximum curvature described by Equation 4, where $n_1=1$ for air, $n_2=1.5$ for most plastics, x is the thickness of the light guide, and r is the inner radius of curvature:

$$x/x+r=n_1/n_2 \qquad \text{Eq. 4}$$

Figure 24:
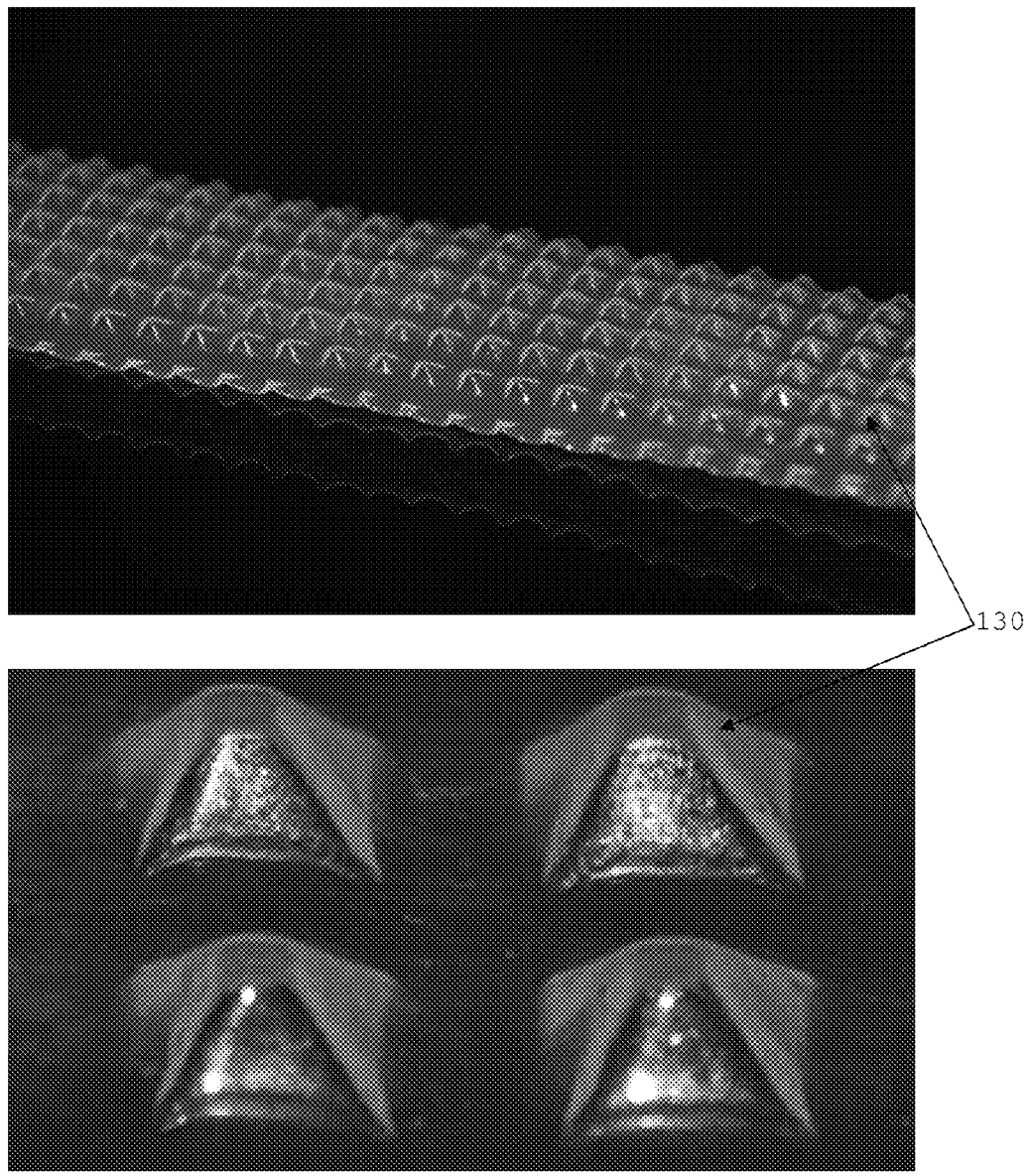
FIG. 24 shows photographs of a symmetrical pyramid shaped light extractors of the disclosure with nearly equilateral triangles with all angles near 60 degrees.
Figure 25:
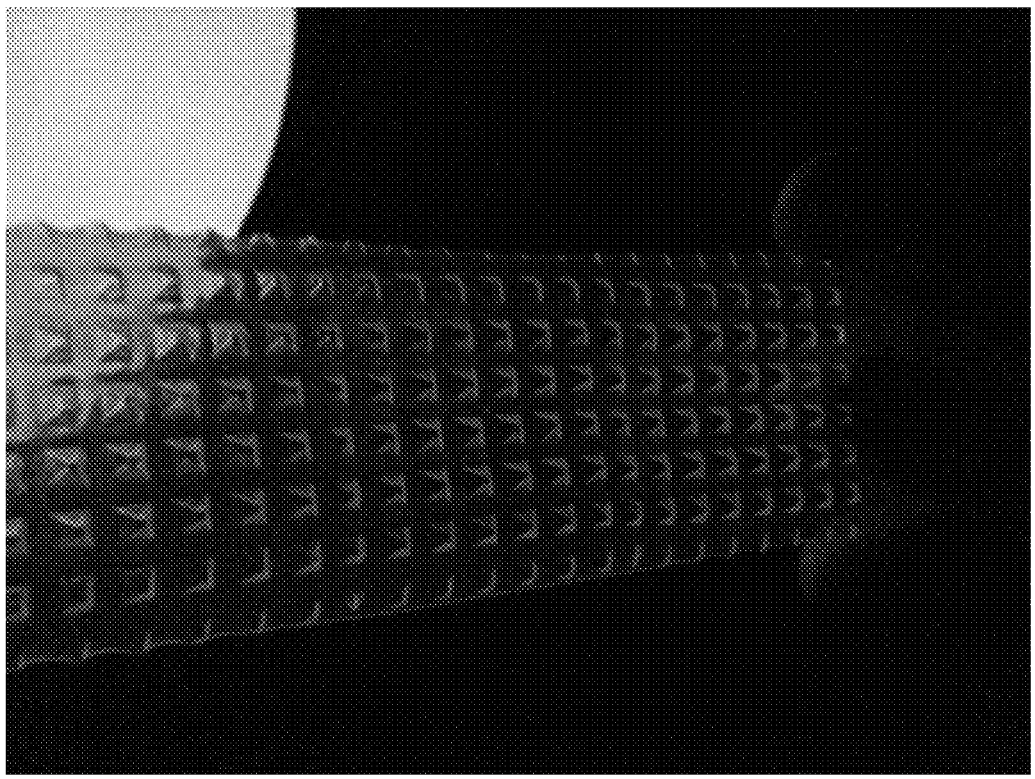
FIG. 25 shows photographs of two sides of a luminescent substrate comprising light extractors of the disclosure under a UV "blacklight". The luminescent light extracted from each light extractor is extremely efficient, but no luminescent light is extracted by the face lacking light extractors.
Figure 25:
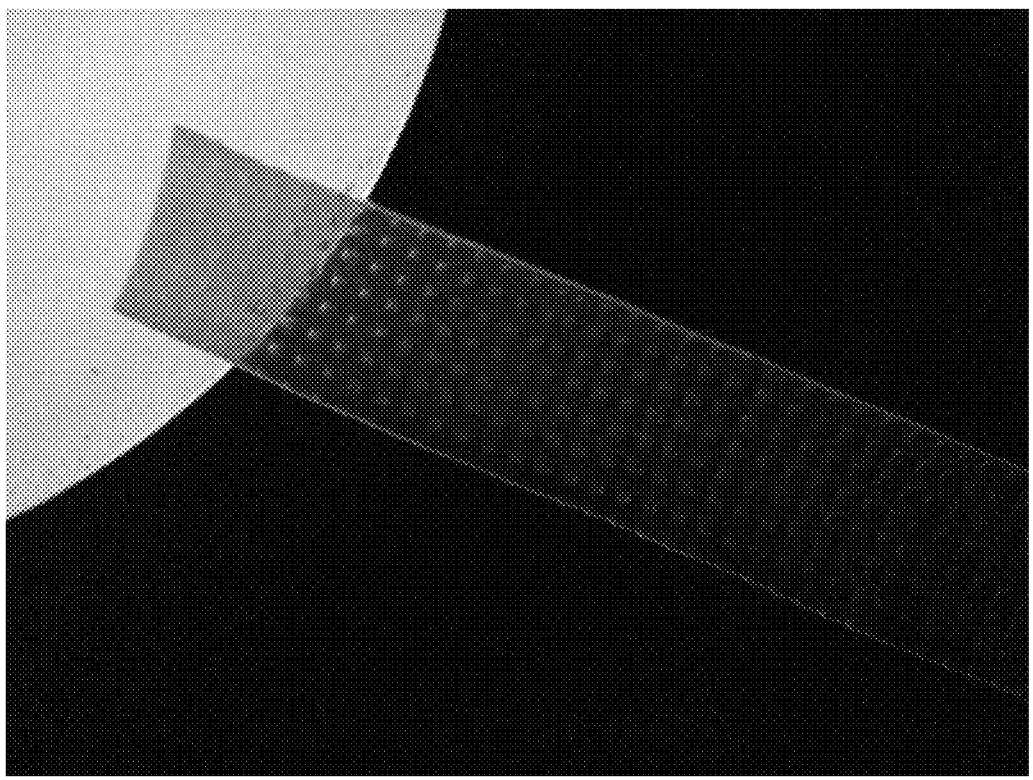
Figure 28:
FIG. 28 are photographs showing light extractors in the form of a cross-shaped indentation. Light is extracted from the positive, raised side of a sample of indented red plastic (left), whereas light is not extracted from the negative, indented side (right). Similar results were achieved with a point indentation (not shown).

FIGS. 24 and 25 show a symmetrical pyramid shaped protrusion with nearly equilateral triangles with all angles near 60 degrees. Light is emitted from the edges of each triangle in the pyramid primarily in the direction which the apexes of the triangles are pointing with the angular range of the trapped light. FIG. 28 shows light extractors in the form of an indentation, either a point indentation or a cross-shaped indentation.

It is important that these light extractors possess the ability to extract light out of one face of the luminescent material or substrate. Directional light extraction can minimise the loss of light to directions that face away from the area to be illuminated.

Figure 26:
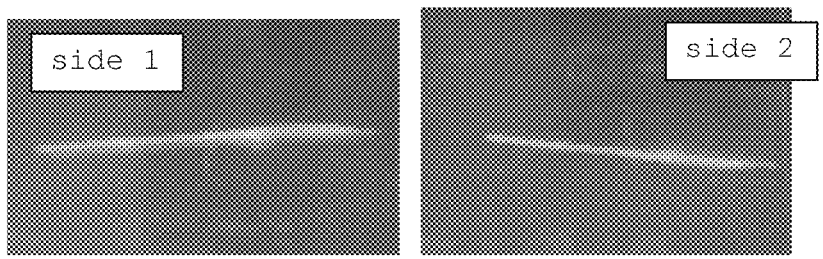
FIG. 26 shows photographs showing a scratch made by a knife on one side of the substrate where both sides of the substrate show nearly identical light extraction.

Other methods such as etching and inclusion of diffusion particles extract light equally from both sides of a material (FIG. 26). For example, etching or scratching the luminescent material or substrate will cause extraction of light from those points, but it will occur on both sides such that 50% of the extracted light would be lost to the outside and only 50% would be directed to the algae below.

Figure 27:
FIG. 27 shows representations depicting equal light extraction from all the vertices in the pyramid (right) and light extraction from one face of the light extractor and in one direction produced by an asymmetrical light extractor that is rounded on one side and possesses a sharp triangular shape on the other (left).

Accordingly, the direction of light extracted from the luminescent material or substrate by the light extractors can be controlled by adjusting the geometry of the light extractors (FIG. 27).

The light extractors on the luminescent material or substrate create a complete escape route for the luminescence such that the light is not guided in the luminescent material or substrate.

As used herein, the term "light guide" or "light conduit" are used interchangeably and refer to any material or construct of multiple materials, solids or liquids, designed to transport light using internal reflection or total internal reflection. This internal reflection is dependant upon the indices of refraction of the materials involved where the materials are transparent or translucent. Fibre optics are the most common example of conduits, but larger systems such as sheets and columns of any unspecified width or length are also included.

A light guide is a material of high or large refractive index (e.g. water, plastic, glass) surrounded by layers of low or small refractive index (e.g. vacuum, gas including air). Light is introduced into the edge (if a sheet) or the end of a tube or strand of high index material (fibre optic cable) at a fairly shallow angle that does not exceed the critical angle for total internal reflection.

The "critical angle" is defined as the maximum angle at which light can be trapped between two specific materials of higher and lower refractive index, e.g. between air and plastic, between plastic and water, or between water and air. Mathematically, the critical angle is defined as $\sin^{-1}(n_{small}/n_{large})$, where n is the refractive index and accordingly $n_{small}$ is the refractive index of the material with the smaller refractive index and $n_{large}$ is the refractive index of the material with the larger refractive index.

For example, plastics and air have refractive indices of approximately 1.5 and 1, respectively. The critical angle is calculated by $\sin^{-1}(1.5/1)$ to give approximately 42 degrees normal (perpendicular) to the surface. Therefore all luminesced light at angles of 42 degrees to 90 degrees will be trapped by total internal reflection. This translates to approximately 53% of the luminesced light being trapped by total internal reflection while the other 47% is lost out of the face of the light guide in what is known as the "escape cone". As used herein, "long" or "length" refers to the predominant dimension in which light is guided or is intended to be guided. "Length" corresponds with the face of a light guide and corresponds with the dimension between two ends or edges of a light guide.

As used herein, "thick" or "thickness" refers to the dimension approximately normal to the "length" of a light guide and thus to the dimension that is approximately normal to the predominant dimension in which light is guided or is intended to be guided. "Thickness" refers to the dimension defined by two opposing interfaces produced by difference in refractive indices, for example, the distance between one plastic/air interface and a second opposing plastic/air interface. Luminescent light guides are often made from rigid transparent polymers such as polymethyl methacrylate or polycarbonate as well as high refractive index liquids such as dimethyl sulfoxide (DMSO) and concentrated aqueous solutions. The luminescent material will luminesce the absorbed light at wavelengths and a conversion efficiency in accordance with the emission spectrum and quantum efficiency, respectively, of the luminescent material.

As used herein, a "luminescent light guide" differs from a "light guide" in that instead of introducing light to the light guide from the edge or end of the light guide, luminescence is produced by a luminescent material of the luminescent light guide and it is the luminescence that becomes trapped and is guided accordingly.

The advantage of the "luminescent light guide" is that light that strikes the non-edge or non-end of the guide, e.g. the length or face of the luminescent light guide, will be absorbed by the luminescent material comprised in the luminescent light guide. When the luminescent material emits light, it is the emitted light that is largely trapped. In a standard light guide, only light introduced into the edge or end of the light guide reflects and is completely trapped inside the light guide until it escapes with very little loss. Light that does not hit the edge or end of the light guide, e.g. hits the length or face of the light guide, will not be guided.

Statistically, luminescence occurs equally in all directions such that the percentage of luminesced light that is trapped by total internal reflection is dictated by the critical angle between the luminescent light guide and the surrounding environment. Although a portion of the luminescence is beyond the critical angle and will escape the luminescent light guide from its face or length, the remainder of the luminescence is trapped and will be guided. Furthermore, the luminescence that escapes from the face or length of the luminescent light guide will nevertheless be of a second wavelength or wavelength range suitable for growing the plant or part thereof, the alga or the cyanobacterium, despite the lack of guidance.

If the light is trapped in the luminescent material or is trapped in a substrate in which the luminescent material is disposed in or coated on, large losses may occur due to re-absorption. If a luminescent material has a 90% fluorescence quantum efficiency, 10% of the light is lost to each re-absorption cycle leading to a ~40% loss over 5 cycles of re-absorption and emission (i.e. $[(1-0.9^5) \times 100]$.

Figure 2:
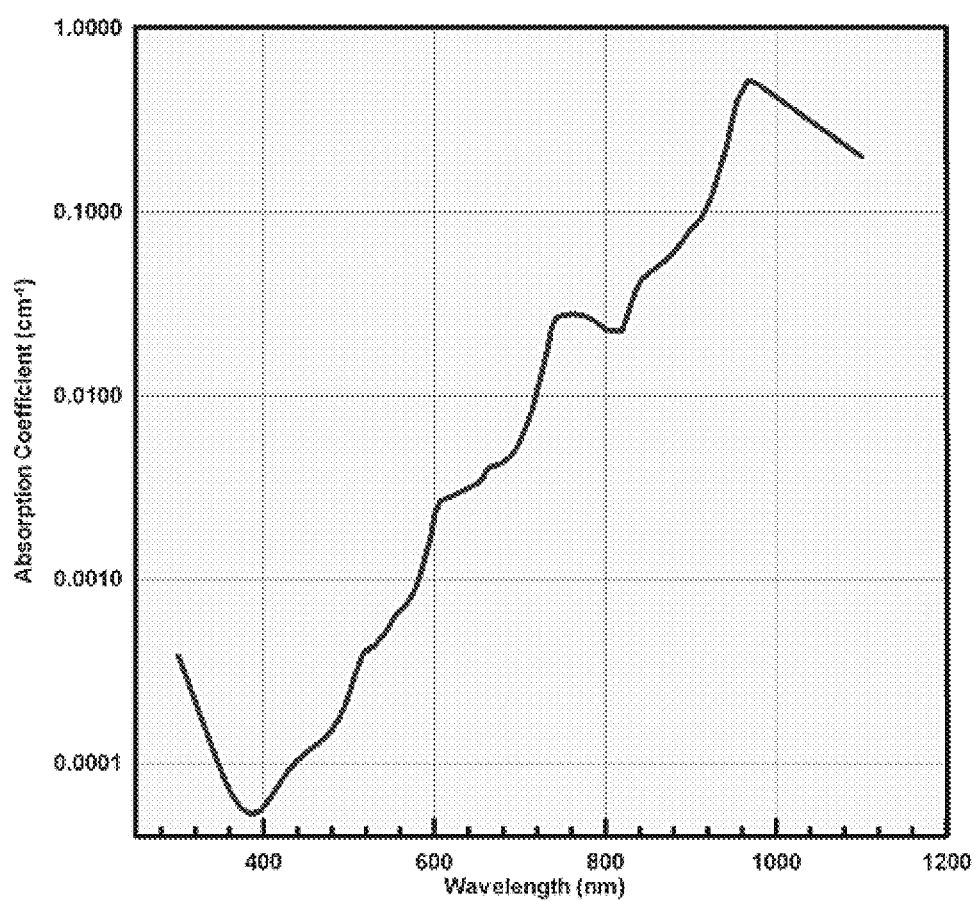
FIG. 2 graphs to optical absorbance of pure water and shows how the absorbance increases by a factor of 10 between 500 nm (about 0.0005 $cm^{-1}$) to 600 nm (nearly 0.005 $cm^{-1}$). This translates to an absorbance of about 1 over a 2 m path length.
Figure 3:
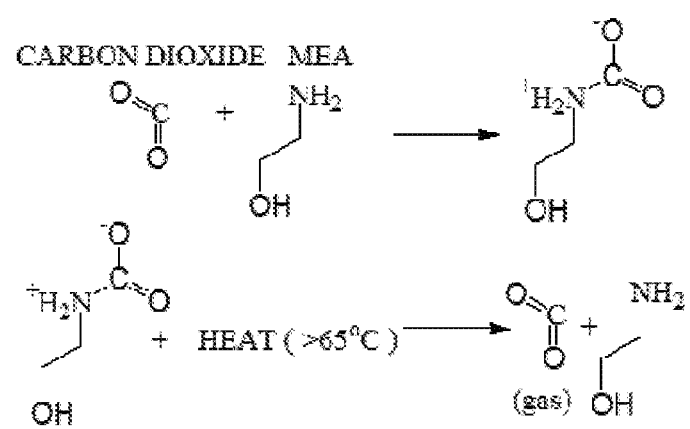
FIG. 3 provides the chemical equations describing the process of carbon dioxide scrubbing by reaction with an amine (monoethanolamine, MEA) and the reversible reaction upon heating for subsequent release of carbon dioxide.

The causes of efficiency losses are: (i) general attenuation of the light by the material itself; materials of high refractive index are known to attenuate light over significant distances, i.e. clear water will absorb nearly 50% of light over a 2 meter path length (with a stronger absorbance of the red portion of the spectrum) (FIG. 2); and (ii) losses due to re-absorption when there is overlap between the absorbance and emission bands of the luminescent material.

Even when the overlap is small, the luminesced light will be largely re-absorbed by the luminescent material in the substrate when the length of the light guide, the pathway of the trapped light, is large compared to the thickness of the light guide. The re-absorption causes losses when the quantum efficiency of the luminescent material is less than 100% such that each absorption/emission cycle causes a loss to non-radiative processes. The re-absorption will be more selective towards light that is close to the overlap region and the resulting spectrum of luminesced light will have a wavelength maximum that is red shifted compared to the spectrum measured over a very short distance.

Figure 17:
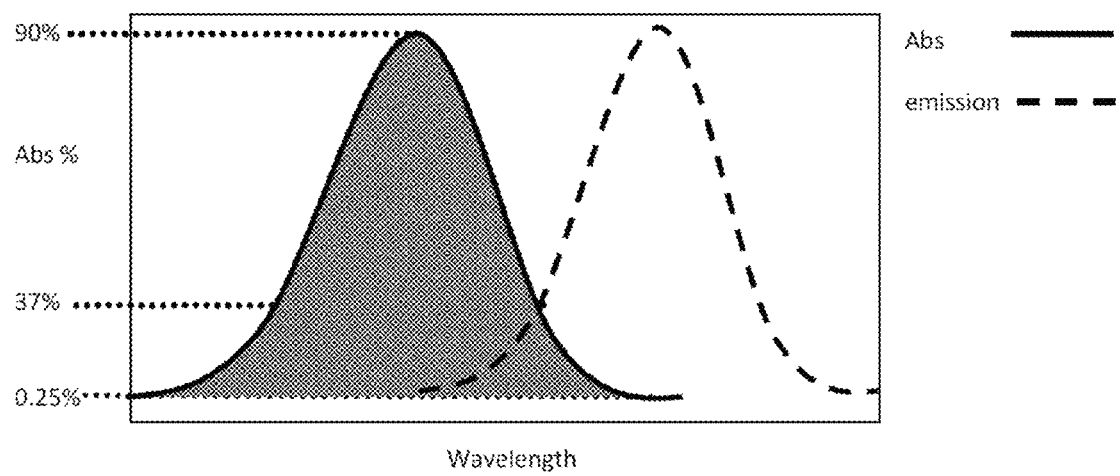
FIG. 17 depicts a hypothetical absorbance and emission band for a luminescent material showing a typical degree of overlap where re-absorption would occur.
Figure 18:
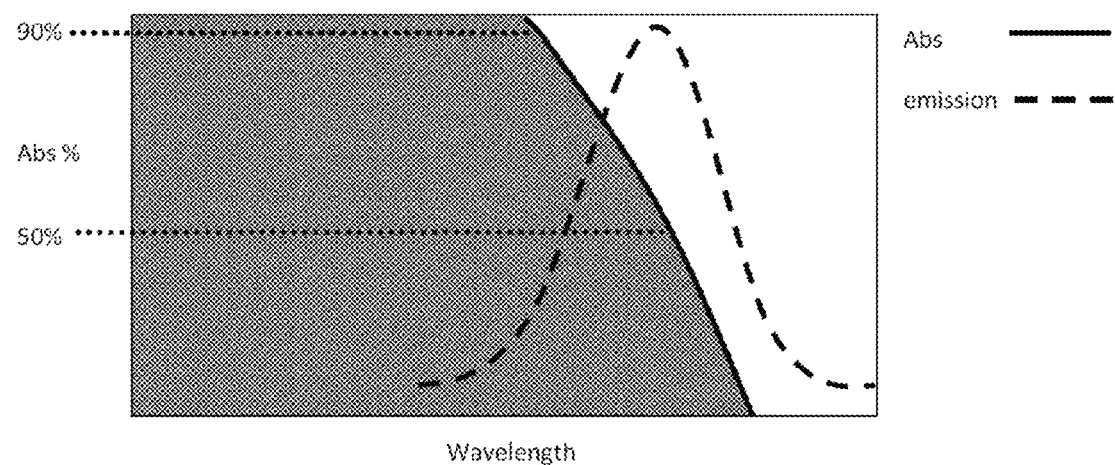
FIG. 18 depicts a hypothetical absorbance spectrum of luminesced light, trapped by total internal reflection in a luminescent light guide, travelling over a distance 200 times its thickness. A large majority the fluoresced light will experience repeated cycles of re-absorption and re-emission over its journey to the edge of the light guide. This effect is reduced as luminescence occurs closer to the edge.
Figure 19:
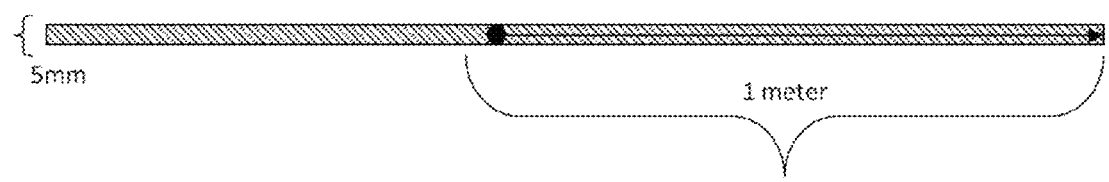
FIG. 19 is a representation of a luminescent light guide comprising a sheet 5 mm thick and 1 m wide from the centre (2 m in total length). A luminesced photon originating from the centre must travel through 1 m of polymer in which the luminescent material is dispersed. The absorbance and emission spectra would then be adjusted to give the spectrum shown in FIG. 18.

Those skilled in the art will appreciate that most luminescent materials display absorbance/emission spectra similar to that depicted in FIG. 17 in terms of the degree of overlap and shape. In this case the hypothetical luminescent material has a 0.25% absorbance value near the wavelength of the emission band peak, which is negligible.

If the light guide is 5 mm in thickness, this is the path length (b) for incident light striking the surface and passing through the luminescent light guide as shown in Eq.2. The light will be absorbed or transmitted as expressed in the spectrum in FIG. 17.

$$0.25\% = \in (5 \text{ mm})c \qquad \text{Eq. 2}$$

If the photon must travel 1000 mm from the centre of the luminescent light guide to reach the edge of the luminescent light guide, the path length is now 200 times longer than the thickness; 1000 mm compared to 5 mm. The equation is then adjusted to show the absorbance of luminesced light that is trapped by total internal reflection as it travels along the length of the luminescent light guide as shown in Eq. 3. This shows that 50% of the luminesced light at the peak of the emission will be reabsorbed along a 1000 mm path length as opposed to the 0.25% negligible absorbance in the 5 mm path length.

$$200(0.25\%) = \in (1000 \text{ mm})c = 50\% \qquad \text{Eq. 3}$$

Luminescent light guides may be used to absorb light over large surface areas and redirect that light as concentrated beams towards their edges at narrow ranges of angles.

The re-absorption effect would be diminished by expanding the thickness of the luminescent light guide to increase the ratio of the thickness to the length. To do this would be expensive and unfeasible for most light guide materials such as polymethyl methacrylate where thicknesses of 100 mm to 500 mm would be required to reduce the re-absorption effects to a large degree. Maintaining optical clarity in very thick layers of polymer plastics is very challenging and handling of such materials is prohibitive.

Multiple layers of luminescent light guide can be used, each with a different luminescent material to capture a different portion so the solar spectrum, to work in concert to absorb and guide very large portions of incident light (solar or artificial) (FIG. 21).

As used herein, "reduce" refers to a decrease, attenuation or minimisation of a given effect. Therefore, to "reduce" reabsorption of luminescent light by the luminescent material is to decrease, attenuate or minimise reabsorption. Reabsorption may be "reduced" by the first substrate by at least about 1% compared to reabsorption in the absence of the adapted first substrate, or reabsorption may be reduced by at least about 2%, 3%, 4%, 5%, 6%, 7%, 8%, 9%, 10%, 12.5%, 15%, 17.5%, 20%, 25%, 30%, 35%, 40%, 45%, 50%, 55%, 60%, 65%, 70%, 75%, 80%, 82.5%, 85%, 87.5%, 90%, 91%, 92%, 93%, 94%, 95%, 96%, 97%, 98%, 99% or 100% compared to reabsorption in the absence of the adapted first substrate.

Luminescent light guides may find application in the field of photovoltaics. A luminescent light guide could be fixed with a narrow strip of photovoltaic material along its edges to capture and convert the concentrated light. The advantage being that the amount of photovoltaic material used is greatly reduced to cover only the edges of luminescent light guide rather than the entire surface area which the luminescent light guide covers. Because luminescent light guide are made from simple polymers or liquids with small quantities of luminescent materials, they are much cheaper, per square meter, than photovoltaic materials.

Luminescent light guides can also be used for other illumination designs where light must be guided, controlled or redirected in an endless range of applications from greenhouses to indoor solar lighting.

One advantage of the luminescent light guide is a more efficient manufacturing process. For a luminescent light guide that is to be constructed, the luminescent material must be dispersed into the polymer layer. If this layer is relatively thick, then this would require more processing of polymer to be dispersed with the luminescent material. The present design allows a smaller quantity of polymer to be processed with luminescent material to create a thin layer and the majority of the luminescent light guide can remain as a clear substrate.

The luminescent light guide comprising two layers, one thin luminescent layer and one thick clear layer, can be supplemented with additional thin polymer layers containing varied luminescent materials that absorb different wavelengths of light, as shown in FIG. 21.

The luminescent light guide can be a large open container filled with a clear medium of high refractive index and layers of thin polymer in which a luminescent material is dispersed. The container may be lined with reflective materials or photovoltaic materials to make the best use of light harvested from the edges. In some cases light is only desired on selected sides or apertures. In such cases a reflective material placed on the luminescent light guide edges would concentrate the luminescence to only the desired extraction or exit points.

The luminescent light guide may be placed in a water tank or under water in any environment. In such an application, the luminescent light guide requires an air interface at which total internal reflection occurs. When the luminescent light guide is placed in water, the air interface is lost when water directly contacts the outside of the luminescent light guide.

In such a design, it is therefore necessary to introduce the air to the luminescent light guide interface by the addition of an air layer above and below the luminescent light guide (FIG. 22). This can be accomplished by adding a double layer of material to the top and bottom of the luminescent light guide where some gas or air is trapped. These thin layers will be effective for effecting total internal reflection. If the luminescent light guide is in contact with air at its top, then only one layer of air must be included on the bottom.

Figure 23:
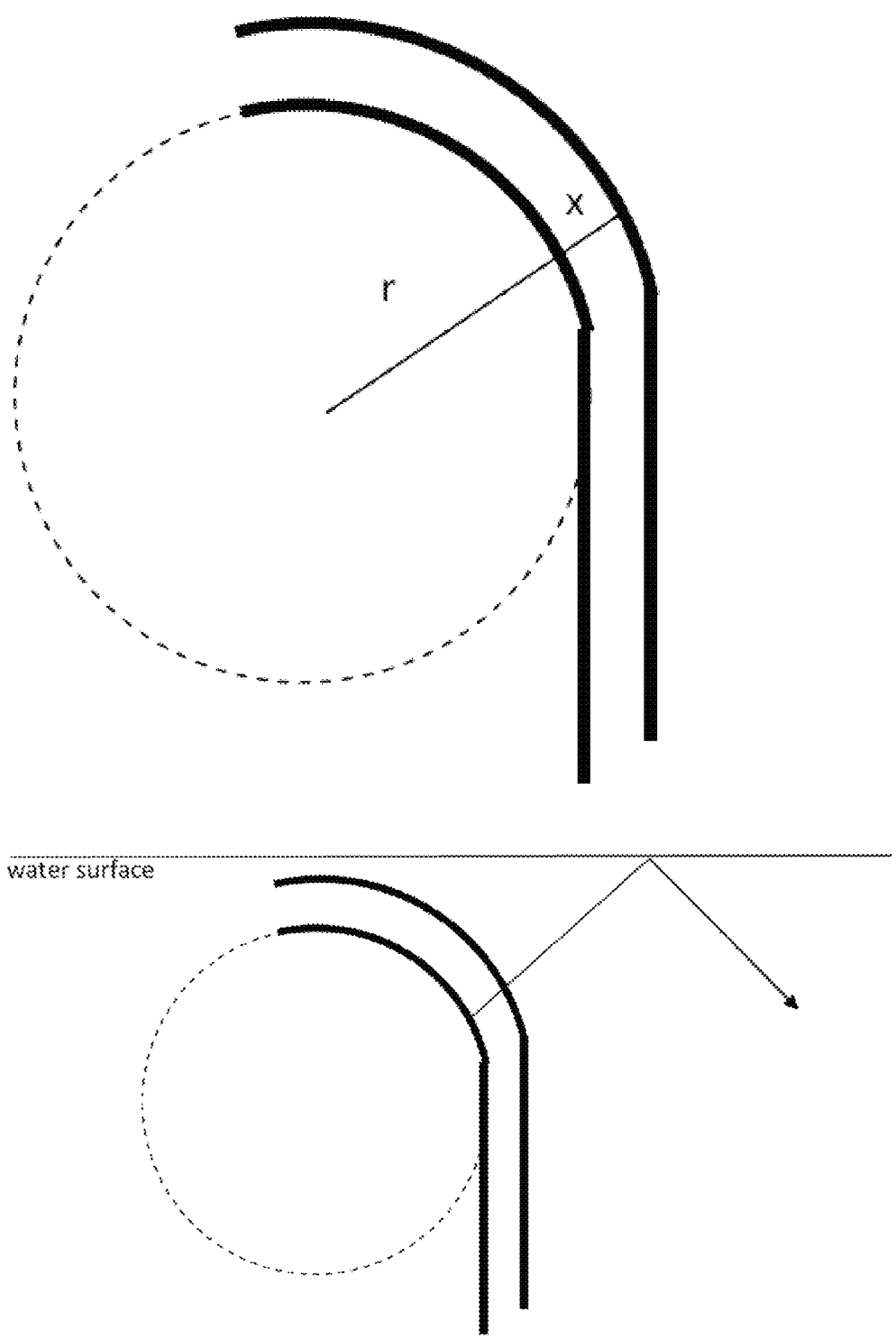
FIG. 23 is a representation of a luminescent light guide of the disclosure showing the maximum curvature attainable by the luminescent light guide (upper). Light that escapes the luminescent light guide may be trapped by the water/air interface such that the light is redirected downwards (lower).

The luminescent light guide placed under water may have a curved shape such that the luminesced light is re-directed, for example downwardly. In such a design, the curvature of the luminescent light guide must not be too severe, otherwise the light may not be guided through the curvature. The maximum curvature of a light guide of thickness x and refractive index $n_2$ is defined as a circle whose radius is r as described in Eq. 4, where $n_1$ is usually equal to 1 for air or vacuum, r is the radius of the inner curvature and x+r is the radius if the outer curvature.

$$x/x+r = n_1/n_2 \qquad \text{Eq. 4}$$

Where the luminescent light guide is a curved geometry placed in water, a portion of the light lost to the escape cone may be recaptured by the water to air interface at the surface of the water, as shown in FIG. 23.

If the clear medium has a lower refractive index than the polymer containing the luminescent material, not all the luminesced light will be extracted into the clear medium.

For example, the clear medium may be water with a refractive index of 1.33 and the luminescent thin polymer layer may have a refractive index of 1.5. In such an example, a portion of the luminesced light will remain trapped inside the thin polymer layer. In some cases this may be acceptable, but in other cases the portion of light trapped in the thin polymer layer can be extracted at intervals along the layer. This extraction can be accomplished by creating light extractors (e.g. formations, impressions, etchings, any number of diffusing geometries, or diffusing particles) that disrupt the guidance of light at particular points along the thin polymer layer. However, etching and diffusion particles are not capable of directional light extraction; instead a light extractor must be formed with suitable geometry to extract light in the desired direction.

The luminescent material, or substrate comprising the luminescent material and comprising light extractors, may be used for a camera filter or other optical device. Unlike other camera or optical filters that simply remove specific wavelengths by absorption, the substrate comprising the luminescent material comprising light extractors can absorb certain colours and enhance others. For example, using a red luminescent material, a substrate lacking light extractors can reduce green and yellow light due to absorption, but a substrate comprising light extractors can reduce green and yellow light due to absorption and increase red light (not shown). Consequently, the luminescent material or substrate comprising the luminescent material comprising light extractors may be used as a filtering and enhancing device, for example in camera equipment, signs and displays.

In one embodiment, the bioreactor will have a smooth, reflective inner surface or lining. The reflective lining may be white and also the lining may be plastic. The reflective lining may maximise the light available for algae growth by reflecting light that hits the inner wall of the bioreactor.

Exposure to light, typically sunlight, of the bank or storage cell during the day in the absence of algae, i.e. external to the bioreactor, will effectively "charge" the bank or storage cell so that it may be added to the bioreactor to provide light for continued photosynthesis to sustain a low level of algae growth during the dark hours. During the dark hours, algae perform respiration which depletes the overall biomass. The use of further luminescent materials during the night can offset some of these losses and may provide a healthy population of algae for the next batch.

Furthermore, the growth medium depth may be much deeper than the depth of sunlight penetration. Thus, a bank or storage cell may be used at depth as well as at night. As the algae-bound substrates near the surface, sunlight will be absorbed by both the algae and luminescent material, provided that the surface of the substrate is not entirely covered by algae. At greater depths, where no sunlight is present, the luminescent material will emit light for photosynthesis and therefore continuously feed light to the algae at the wavelength most necessary for photosynthesis. The substrates may be able to feed light to the algae for a number of hours.

When exposed to air, the growth medium is exposed to air at its surface, and a portion of carbon dioxide from the air is dissolved in the growth medium. Turning or mixing the growth medium increases exposure of the growth medium to air and enhances dissolution of carbon dioxide into the growth medium. Other methods of introducing carbon dioxide into the growth medium can be employed, as will be appreciated by those skilled in the art, including a carbon dioxide bubbler or jet (or multiple bubblers or jets), introducing carbon dioxide gas into the growth medium at one or multiple gas ports in the bioreactor. Carbon dioxide bubblers or jets can also serve as mixing and impelling means. Additionally, another method involves increasing the concentration of carbon dioxide in the air above the bioreactor, such as by forming a sealed enclosure over the bioreactor, and introducing carbon dioxide gas in the area over the surface of the growth medium and within the enclosure.

Algae possess a strong ability to bind surfaces. In one embodiment, the algae will grow upon the surface of the luminescent material. In another embodiment, the algae will grow on the surface of the substrate. An advantage of growing algae on a surface is that the biomass presents itself in a concentrated state as a thick layer on the surfaces.

When more than one substrate is present, the substrates can be easily filtered, and therefore makes harvesting facile. In one embodiment, the filtered substrates covered with algae can be removed, washed with water to remove salts from the medium and the algae can then be removed from the substrate by a number of methods, one of which includes altering the pH of the growth medium to disrupt the binding of the algae to the substrate, or first drying the substrates and removing the algae as a powder. High pressure water jets may also be used to remove algae from the substrate. The substrates, now free of algae, can be returned to the system to support another batch of algae.

Harvesting may be accomplished by mechanical wiping, high pressure water, or allowing the algae to dry on the sheets to be collected as a semi-dry solid, for example. Harvesting may comprise wiping, scraping, washing, rinsing, drying, partially drying, shaking, vibrating, or altering the pH.

In one embodiment, the bioreactor will grow algae on substrates that allow algae to be harvested as a thick mass with limited water content thereby avoiding costly filtration and centrifuge processes. By removing only the amount of water necessary for utilising the algal biomass as a feedstock for direct gasification, for example, energy expenditures used in producing biofuel from the algal biomass will be minimised.

When used as a carbon source, carbon dioxide may be obtained from the ambient atmosphere. Alternatively, carbon dioxide may be derived from a specific source. These include industrial, agricultural and human sources.

Industrial—PCC and IGCC

The present disclosure may be compatible with carbon dioxide capture methods that are currently being developed for clean coal technologies. These technologies mainly include Post Combustion Capture (PCC) using amine solvents and Integrated Gasification Combined Cycle process (IGCC) to produce hydrogen as a major component of "syngas".

These clean coal technologies are crucial in isolating the carbon dioxide component of flue gas emissions, but they do not offer a method of sequestering or processing the captured carbon dioxide per se. Importantly, IGCC offers a method of much higher thermodynamic efficiency in burning fuel, and would make the best use from the energy stored in algal biomass.

Post combustion capture of carbon dioxide is largely accomplished using amine solutions, typically monoethanolamine (MEA), that quantitatively react with all carbon dioxide from a relatively cool gas stream. The reaction is then reversed by heating the amine solution thereby releasing the carbon dioxide as a pure stream, particularly for sequestration. The chemical reaction is provided in FIG. 2.

The capture of carbon dioxide by amines is a convenient way of handling large, concentrated volumes of carbon dioxide at standard pressures in aqueous solutions. Carbon dioxide normally has a relatively low solubility in water, especially in warm water (30° C.). There are many amines that can be used for this process such as triethanolamine (TEA). The amines are largely reusable, biodegradable, and inexpensive. Contemplated herein is use of an amine that is non-toxic to algae in a growth medium to allow high concentrations of carbon dioxide injection into the bioreactor for providing a convenient source of inorganic carbon for the algae. Such a medium would be both a carbon dioxide sequester and an algal biomass generator. The algae may uptake carbon dioxide from the amine solvent.

Thus, the present disclosure will produce an algae biomass that can be used as a feedstock for gasification, thereby replacing a portion of the coal necessary for power production. In addition, the use of algal feedstock in IGCC will allow the large scale production of hydrogen gas, the most environmentally friendly fuel on earth, from a renewable resource.

Industrial—Untreated Flue Gas

Using untreated flue gas emissions as a source of carbon dioxide and hence inorganic carbon for algae growth has been hindered by the large amount of acidic sulfurous and nitrogenous components, solid particulates, and most importantly, the excess heat from flue gas which is commonly found in temperatures close to or greater than 80° C. To date, these temperatures and contaminants have precluded the use of flue gas emission without pre-treatment, though flue gas emissions are one of the very few viable sources of large quantities of concentrated carbon dioxide for mass scale algae production.

Agricultural

It is envisaged that effluent waste, for example dairy effluent wastewater, may be treated in a bio-digester to generate biogas as a fuel. Methane may be produced from the bio-digestion of effluent wastewater by methanogenic bacteria. Furthermore, emissions from combustion of the biogas may be used as source of carbon dioxide for photosynthesis. The resulting algae biomass may be used as a biofuel feedstock or a protein rich feed for livestock.

Subsequently, the treated effluent waters may be used as growth medium comprising trace nutrients for growth. Finally, the water depleted of nutrients via algal growth, can be distributed as irrigation for the farm pastures.

Alternatively, human wastewater or sewage may be used.

EXAMPLES

In one embodiment depicted in FIG. 4, the bioreactor comprises a series of flexible plastic containments 50, such as tubes or triangular shaped bags, with no predetermined length other than that dictated by factors of practical engineering (FIG. 4a). The plastic containments 50 will sit side by side lying horizontally along the floor 51 of an open pond 52 with a uniform depth, deeper than conventional algae ponds with depths of only 30 cm to 50 cm. The containments 50 are filled with algae growth medium. The algae will be grown inside these plastic containments 50 while the inverted triangular spaces 54 between the containments will remain as clear water to allow the passage of light.

Thus, the clear water is a light guide, which is formed by the containment apparatus. In other words, the algae containment apparatus is capable of forming a light guide. The algae containment apparatus may form a light guide in cooperation with a vessel wall, or another algae containment apparatus. The boundaries of this light guide may include the air/liquid interface, the wall of an adjacent algae containment apparatus or the wall of a vessel in which the algae containment apparatus is positioned, or a luminescent light guide, for example as positioned in FIG. 34 (or FIG. 4e or 4f).

As shown in FIG. 4b, the plastics of the containments 50 comprise the luminescent substrates 60 and will luminesce wavelengths of light useful for photosynthesis. Piping 56 with intermittent holes 58 for delivery of $CO_2$ rich gases will lie at the base 51 of the algae containment apparatuss 50 and produce a stream of gas bubbles to both infuse the growth medium with gaseous nutrients for photosynthetic growth as well as creating a scrubbing action, by the bubbles themselves, that will help to reduce bio-fouling on the face of the polymer materials. The gases will also form a convection type motion in the water to help mix the algae bringing them closer to and further away from the substrate surface, and therefore the light source. As is known in the field of algae biology, light and dark reactions in photosynthesis require the algae to spend a large portion of time away from the light source to prevent photo-inhibition.

The system can be designed as an open pond 52 or as a more dynamic raceway type design (see FIG. 4c raceway design) that has proven to be the most effective open design to date. In a raceway design, the containments 50 would lie along the straight sections 67 while the curved sections 68 would be open to air as a place for infrastructure such as paddle wheels (or other devices for water circulation known in the art), harvesting equipment, water exchange, nutrient addition and gas exchange. In such a design, the water in the curved portions 68 may be filled with algae in open type design where it can be harvested. In this configuration the containments 50 are open at the ends to allow the algae to fill these sections. The clear water 54 between the containments 50 will be sealed off to prevent contamination of the clear water by algae. Alternatively, the curved sections 68 may be clear of algae where the clear spaces 54 extend into these open sections. The clear water should often be filtered to allow the best transmittance of light. In addition, the clear water will absorb a majority of the IR portion of the solar spectrum and will become warmer as a result. The clear water may be released and replaced to act as a thermostat for the entire system where excess heat is diverted away from the system. In winter months, the clear water may act as an insulator to keep the temperature of the algae above a set minimum according to the needs of the particular species.

The luminescent substrate 60 is surrounded by a layer of air 62 that creates a degree of total internal reflection to trap a portion of the luminescent light within the algae growth medium by the positioning of a boundary of higher index of refraction, i.e. water having an index of refraction of approximately 1.33, adjacent a boundary of a low index of refraction, i.e. the air with an index of refraction of approximately 1. This enables the algae containment apparatuss 50 to act as large light guides. The air layer 62 is maintained by a clear polymer sheet 64 outside of the luminescent substrate 60. It may also be advantageous to line the containment 50 with a thin, expendable polymer containment 66 to prevent fouling of the valuable substrate by direct contact with the algae biomass and thus increase the useful lifetime of the more expensive luminescent substrate.

Figure 4D:
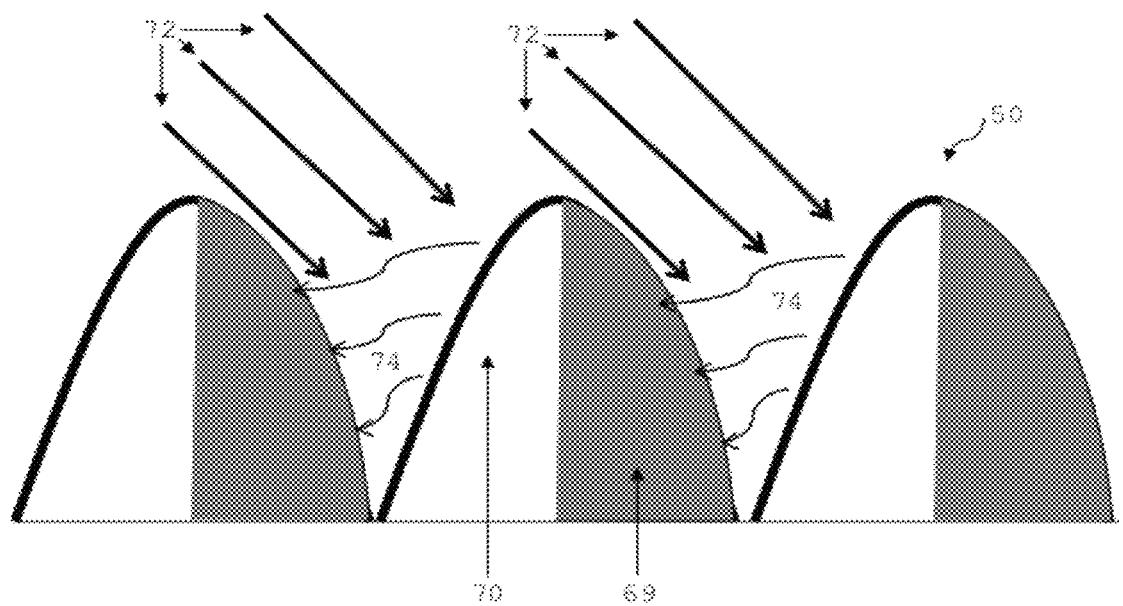
FIG. 4 provides schematic representations of an embodiment of the algae containment apparatus and an embodiment of a bioreactor comprising the algae containment apparatus.
FIG. 4*f* is an elevation view according to FIGS. 4*d* and 4*f* of a plurality of algae containment apparatus each comprising a light guide. Also shown is orange light emitted from the edge of the light guides.
FIG. 4*g* provides longitudinal cross sections of embodiments of the light guide of FIG. 4*e*.
FIG. 4*h* provides a schematic representation of one embodiment of adjacent algae containment apparatuses comprising first and second light guides FIG. 5 provides an orthogonal representation (FIG. 5*a*) and a cross-sectional representation through section 5*b*-5*b* (FIG. 5*b*) of a prismatic light guide.

When sunlight strikes the surface 53 of the pond 52 it will travel down the clear spaces 54 between the algae containment apparatuss 50 and either pass through the luminescent substrate 60 to directly illuminate the algae or first be absorbed by luminescent material disposed in the substrate and then be converted, by luminescence, to a lower wavelength of light useful for photosynthesis before being absorbed by the algal biomass. Whether sunlight is absorbed by the luminescent materials is largely dependent on the particular wavelengths of the light where certain wavelengths pass through the luminescent substrate 60, not lying within the major absorbance wavelengths of the disposed luminescent materials, while others do undergo an absorbance/emission process. The entire system of containments 50 can be oriented, according to cardinal directions, to lie north to south, east to west, or any direction in between. As shown in FIG. 4d, in either orientation, there will be a shadow 69 cast on one side of the containment 50 while the other side is illuminated 70 at times when the sun is not nearly or directly overhead. These periods of low angled sunlight represent the majority of daytime hours for all latitudes on earth. When sunlight 72 strikes the non-shaded side of the containment 50, the resulting luminescence from the luminescent substrate 60 will radiate partially outwards 74 and cause the shaded side 69 of the adjacent containment to be illuminated by useful wavelengths of light. These sides will alternate between shaded and illuminated between morning and evening hours as the sun moves across the sky.

Figure 5A:
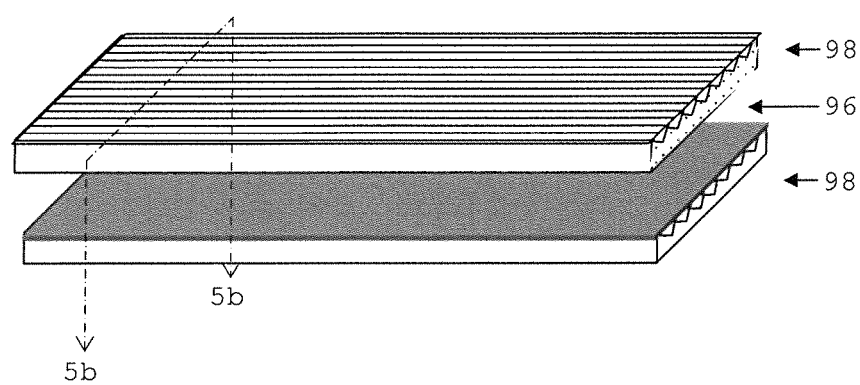
Figure 5B:
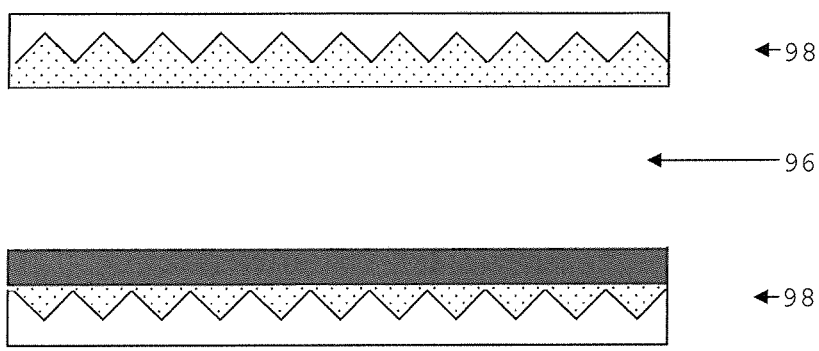

It is of particular importance to produce large amounts of red light between 600 nm and 700 nm as these wavelengths are used very efficiently by photosynthetic organisms. Also, in deeper pond systems, the absorbance by water of incoming red light can be a significant factor (FIG. 5) where a clear channel of water will absorb approximately 90% of red light at 650 nm over a path of 2 meters. Shorter wavelengths of light such as orange, yellow, green and blue (575 nm to 400 nm) pass through water with much less loss and can be down-converted to red light at deeper depths after they have made their passage through the water column.

The shape of the system causes the effective algal surface to be more than doubled when compared to the surface area 53 of the pond 52 in which they are contained. The taller the containments 50 are made, the greater the effective area. This creates dilution of the sunlight striking the surface of the system over a larger area than it would encounter with a standard open pond. Thus, lower light intensities are encountered and therefore lowered occurrences of photo-inhibition are observed. In addition, the substrates that comprise the algae possess the ability to convert natural sunlight into a spectra of wavelengths more optimised for photosynthesis to achieve a higher solar energy conversion efficiency measured by an increase in biomass accumulation per square meter of area. This system may thus achieve higher algae concentrations as well as algae growth at greater depths. At greater concentrations of biomass, growth (e.g. biomass doubling) leads to exponentially greater gains. In addition, the higher biomass concentration allows for less energy to be expended in the harvesting system that begins with biomass concentration followed by dewatering.

Figure 4E:
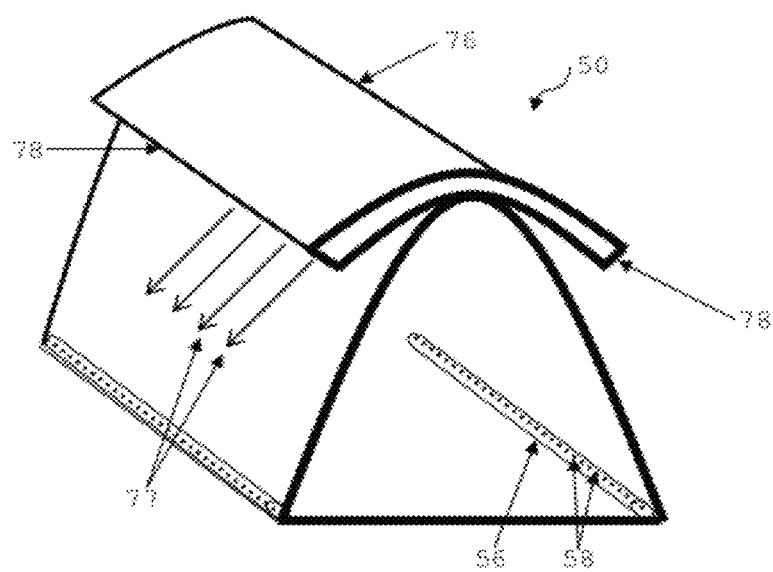
Figure 4F:
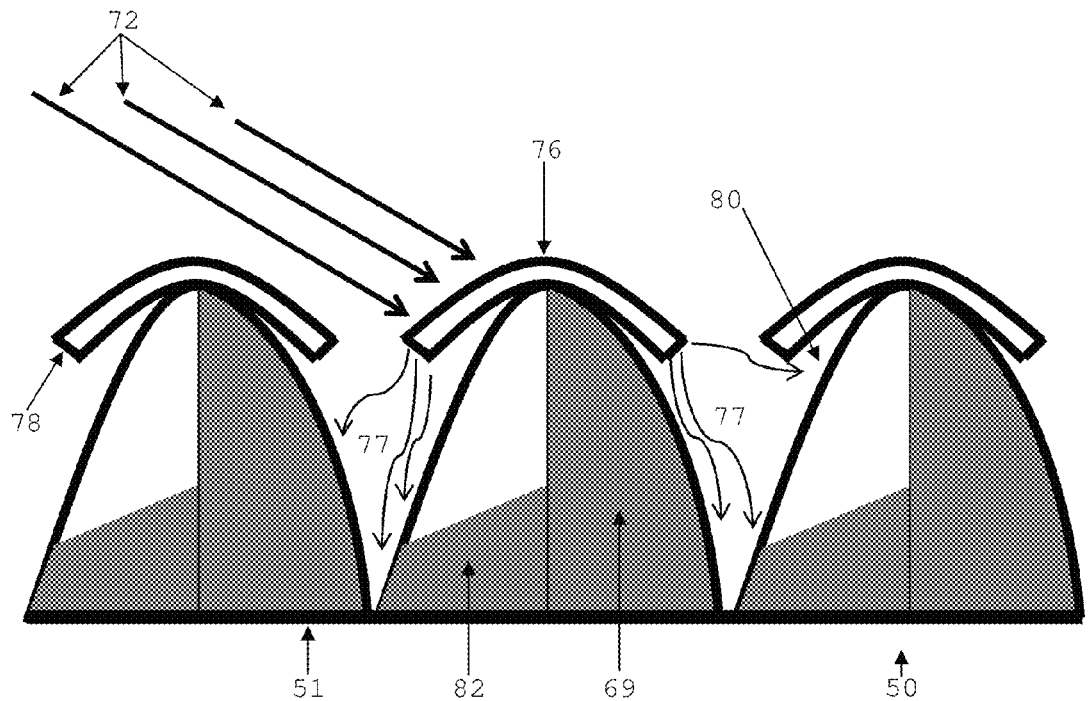

As illustrated in FIG. 4e and FIG. 4f, a fluorescent light concentrator, or fluorescent light guide, 76 may be added to the top of the algae containment apparatus 50. The addition of such a light guide must be weighed against its cost/benefit analysis that may be positive or negative depending on the additional biomass gained and its inherent value. In one embodiment, the additional light guide 76 luminesces orange light 77 between 540 nm and 600 nm by the absorbance of light between 400 nm and 540 nm. Since this orange light 77 of higher energy wavelength is produced near the surface of the water 53, the orange light will pass efficiently through the clear water channel 54, with minimal absorption losses, since its wavelengths are shorter than 600 nm. When the orange light 77 is produced it will be emitted out of the edges 78 of the light guide 76 that are bent slightly downwards to direct the light into the clear water channels 54.

Once the orange light 77 reaches the surface of the algae containment apparatuss 50 it will be largely absorbed by the luminescent materials disposed in the luminescent substrate 60 and further down-converted to a red light to enable efficient photosynthesis. To save on costs, the portion 80 of the containment 50 that lies underneath the light guide 76 may or may not be disposed with luminescent materials as it will receive readily optimised light as the light guide above filters the green wavelengths.

This additional light guide 76 will aid in illuminating the bottom portion 82 of an algae containment apparatus 50 that is deep (greater than 1 meter). In such a system, the bottom portion 82 of the containment 50, even when facing the direction of the sun, may remain shaded 69 at hours of low angled sunlight. The light guide 76 will work in concert with the containments 50 where the light guide converts green light to orange and the containment converts orange to red.

Figure 4G:
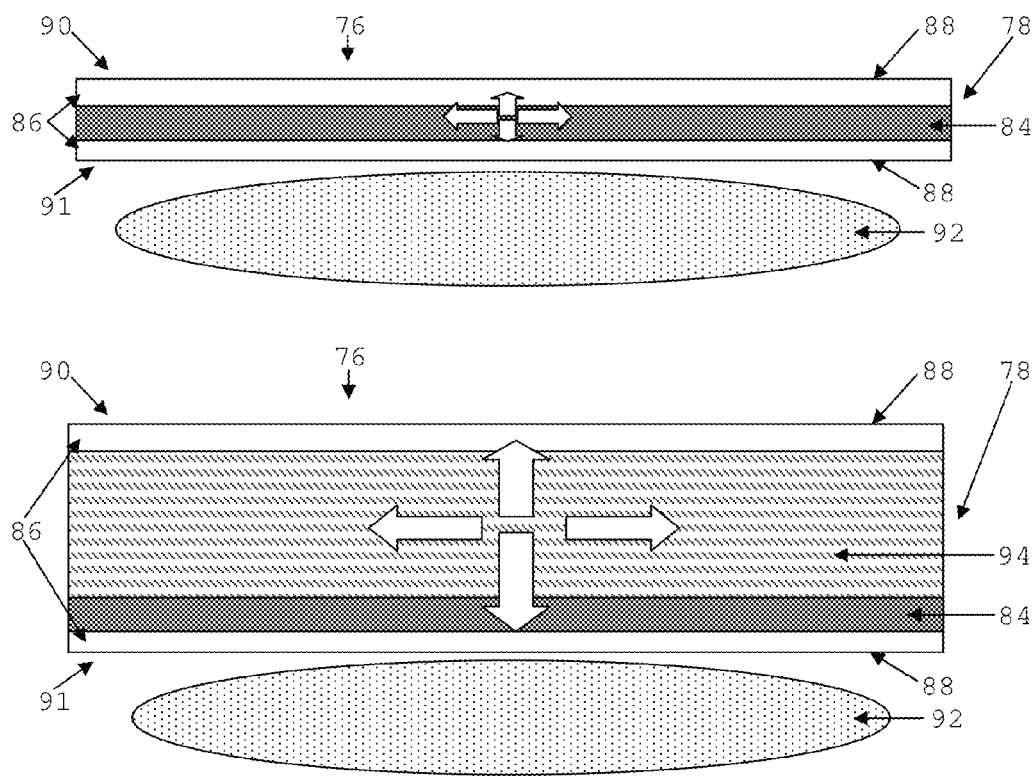

As depicted in FIG. 4g, the light guide 76 comprises a polymer sheet 84 embedded with a fluorescent dye to create a fluorescent solar collector where the luminescence is concentrated towards the edges 78 as is known in the art. Since the light guide 76 will be in contact with water it is therefore pertinent to surround the polymer sheet with a layer of air above and below 86 by the addition of two additional thin clear sheets of polymer 88. The light is trapped within the sheet by total internal reflection and conducted towards the edges 78 for all light that is within the critical angle defined by the refractive indices of the polymer and the surrounding air. For most plastics this angle is about 42 degrees from the vertical where all light that is less than this angle from the vertical is emitted out of the top 90 and bottom 91 faces of the sheet. For most applications the emission out of the faces 90, 91 is considered a loss, whereas it is an advantage of the present system that light emitted from the bottom face 91 of the sheet is transmitted directly into the algae biomass 92.

As with most fluorescent concentrators, there is significant loss due to reabsorption of fluoresced light when the emission wavelengths overlap somewhat with the absorbance due to the limited Stokes shift of most fluorescent dyes. The losses due to reabsorption become significant when the ratio of the thickness of the light guide is very small compared to that of the length that defines the pathway that the light must travel within the sheet to reach the edge. Apart from limiting the total length of the light guide to reduce collection efficiency losses, it also possible to increase the thickness of the light guide to increase the thickness to length ratio using an inexpensive material 94 with a similar index of refraction to the light guide polymer. This material may be a liquid or solid, but the most economic choices are liquids such as aqueous salt solutions (e.g. concentrated $CaCl_2$), or solvents such as DMSO, n-glycol (where n=1, 2, 3, 4 etc.), glycerine and other liquids or mixtures of liquids as is known in the art. Also, the layer containing the luminescent material 84 may also be a liquid such as synthetic liquids, paraffin oil or silicon based oils.

Other forms of light guides may be employed such as prismatic light guides (FIG. 6) that are advantageous in allowing a large gap of air 96 to act as the light conduit where light spends very little time within the polymer materials 98. Such light guides are available commercially from companies such as 3M™.

The substrates that comprise the algae containment apparatuss 50 are composed of a durable flexible polymer in which one or more luminescent materials are disposed. The luminescent material is in the form of a dissolved dye, e.g. an organic dye that absorbs a broad spectrum of light between 350 nm and 600 nm and luminesces between 600 nm and 700 nm. This may also be achieved by a mixture of dyes that able the substrate to evenly collect a broader range of wavelengths. The substrate may also include a fluorescent material that absorbs UV and blue light to emit light between 400 nm and 475 nm to satisfy the blue light requirements for photosynthesis. It is noted however that blue light can penetrate a water column with very little absorption losses such that blue light contained in the natural solar spectrum will reach the substrates even at deeper levels of the system without the addition of a blue emitting material. The ability to produce both red and blue emission from the substrate is useful in helping to illuminate adjacent containments that are shaded as described previously.

When mixing dyes in the same substrate layer there comes an inherent problem of re-absorption where high energy wavelengths of light that are produced from a blue emitting dye are absorbed by other dyes in the substrate rather than being emitted and used efficiently by the algae. To help alleviate this problem, diffusion particles are introduced to extract light out of the substrate giving the substrate a cloudy appearance rather than a translucent one. Such techniques are known in the art as light extraction techniques and are often achieved by the use of such particles as silicates and other small particles. Luminescent (fluorescent or phosphorescent) particles can achieve this diffusion of light while also serving in their original capacity as luminescent materials. Having phosphorescent materials in the substrates, such as a bright green emitting phosphor, will allow a portion of the UV and blue portions of the spectrum to be absorbed and released slowly over a period of many hours. This emission will extend into night-time hours and extend the effective growth hours of the system even after the sun has disappeared. While most phosphorescent materials emit blue and green light, there is a lack of red emitting phosphorescent materials with the same brightness and favourable properties as the more common blue-green counterparts. The more robust and strong emitting green phosphor is useful when disposed in a substrate with a red fluorescent dye. The green light created by the phosphor is then absorbed by the red emitting dye in the substrate creating a red glow in the absence of sunlight to produce the desired red light for algae growth.

Surround for a Flower

As shown in FIG. 6, a surround 100 may be positioned to surround a flower 102 of a plant 104. Depending on the luminescent material and thus the emitted light of the second wavelength or wavelength range, the surround 100 may enhance the colour of the flower 102.

Cover for a Plurality of Flowers

As shown in FIG. 7, a cover 106 may be positioned above a plurality of flowering plants 108. Depending on the luminescent material and thus the emitted light of the second wavelength or wavelength range, the cover 106 may enhance the colour of the flowers of the plants 108 or may enhance the rate of growth of the plants or development of the plants, or part thereof such as the flowers.

Luminescent Light Guide

Figure 8:
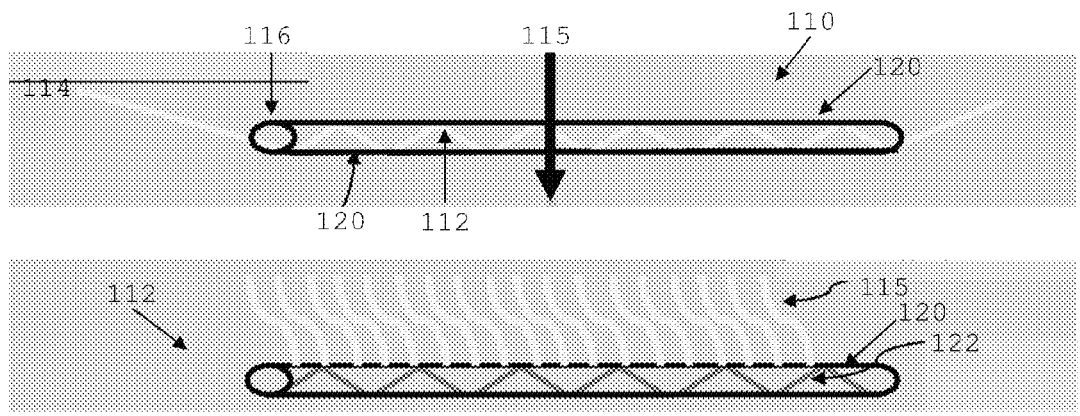
FIG. 8 is a cartoon representation of a light guide (upper) and a luminescent light guide (lower).

As shown in FIG. 8, a light guide 110 and a luminescent light guide 112 are depicted in FIG. 8.

Light 114 enters the light guide 110 at the edge or end 116 of the light guide and then light within the critical angle is guided by total internal reflection 118. However, light 115 that enters the light guide on the length or face 120 of the light guide passes through the light guide and is not guided.

In contrast, light 115 that enters the luminescent light guide 112 on the length or face 120 of the luminescent light guide is absorbed by the luminescent material and then emitted light of the second wavelength or wavelength range that is within the critical angle is guided by total internal reflection 122.

Light Extractors in a Luminescent Material or Substrate Comprising a Luminescent Material As shown in FIG. 9, a light source 124 applied to a luminescent material or substrate comprising a luminescent material lacking light extractors 126 transmits light to the edges 128 of the material or substrate, which can result in substantial losses of light. In contrast, a light source 124 applied to a luminescent material or substrate comprising a luminescent material comprising light extractors 130 does not transmit light to the edges of the material or substrate. The light extractors provide an escape route for the luminescence, thereby reducing losses due to transmission within the luminescent material or substrate.

Method for Manufacturing a Luminescent Light Guide

As shown in FIG. 10, a luminescent light guide 112 may be manufactured by positioning a luminescent material, or substrate comprising a luminescent material (e.g. a formed plastic), comprising light extractors 130 between layers of a material of high refractive index 132 such as air. Emitted light of the second wavelength or wavelength range that is within the critical angle is guided by total internal reflection 122. The air, or other material of high refractive index, may be contained by spaced apart double walls 134, which are required for aquatic use.

Figure 11:
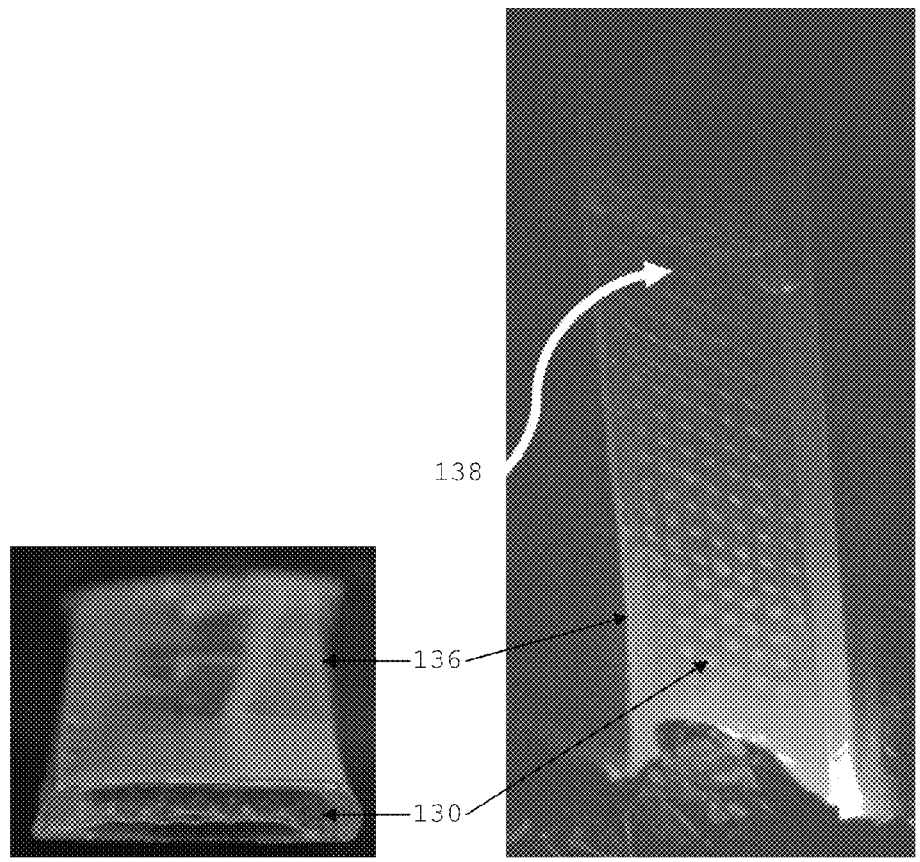
FIG. 11 are photographs of a luminescent light guide of the disclosure comprising light extractors (a formed plastic) inside a plastic sleeve filled with water. The light is guided by the water and guidance stops at the water fill line (right).

If for terrestrial use, the air may be provided by the ambient atmosphere, as shown in FIG. 11. FIG. 11 illustrates a luminescent material, or substrate comprising a luminescent material (e.g. a formed plastic), comprising light extractors 130 inside a plastic sleeve 136 filled with water. The light uses the water inside the sleeve as the conduit and stops at the water fill line 138.

Method for Manufacturing an Algae Containment Apparatus and a Bioreactor

Figure 12:
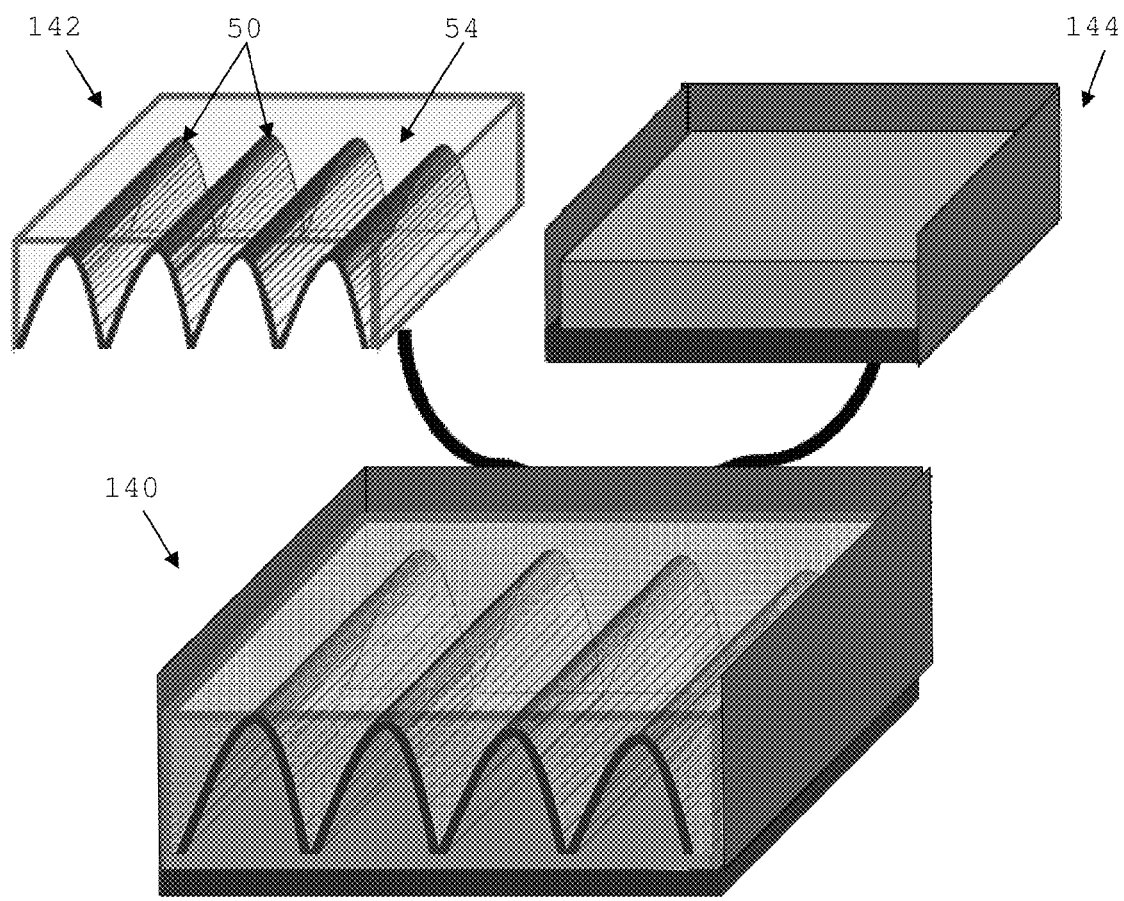
FIG. 12 is an orthogonal representation of a method of manufacturing a bioreactor that comprises a plurality of algae containment apparatuses formed into a sealed insert that is positioned in a vessel. Clear water is located above the algae containment apparatuses.

A bioreactor 140 comprising a plurality of algae containment apparatuses 50 each comprising the luminescent material or substrate comprising the luminescent material, is depicted in FIG. 12. In general, the bioreactor is formed by connecting the plurality of algae containment apparatues to one another. A sealed insert 142 in which clear water 54 is located above the algae containment apparatuses is formed by sealing the connected plurality containment apparatuses. The bioreactor 140 is then formed by positioning the sealed insert 142 in a vessel 144, e.g. a tank or a pond, containing algae.

The sealed insert may be manufactured from a clear plastic.

Figure 13:
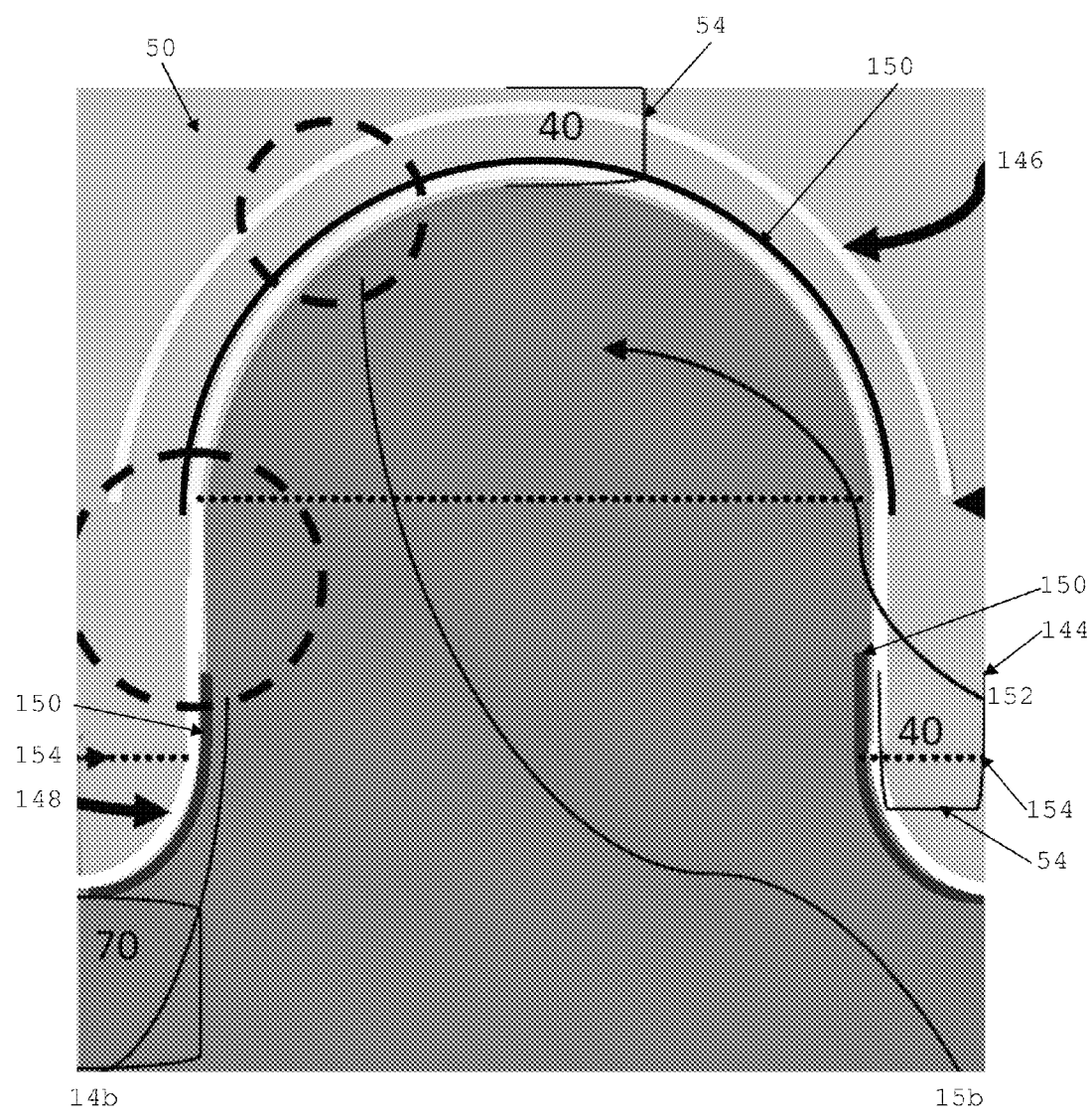
FIG. 13 is a cross-sectional representation of an algae containment apparatus comprising first and second light guides.
Figure 14:
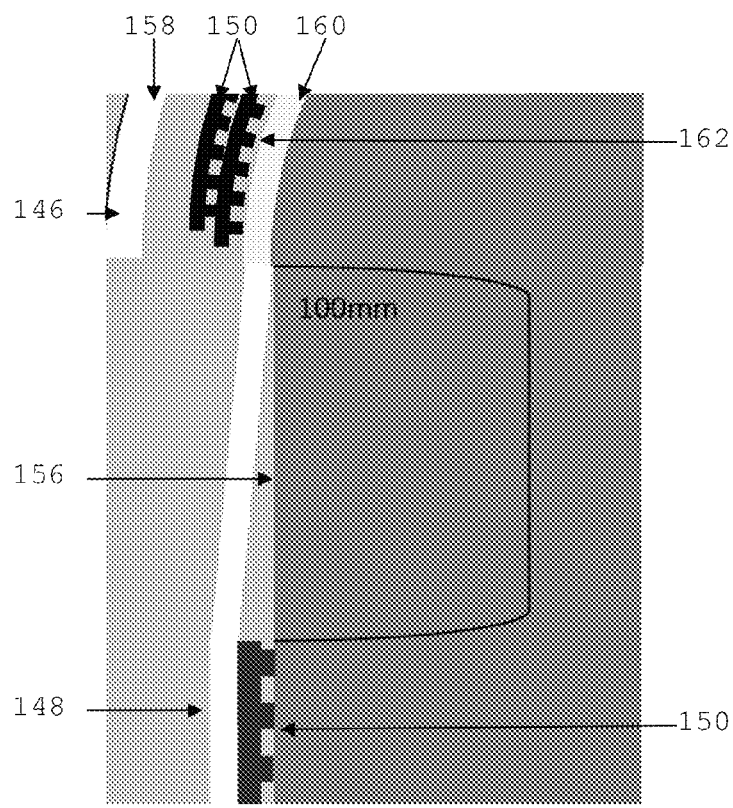
FIG. 14 is a cross-sectional representation of detail 14*b* of FIG. 13.
Figure 15:
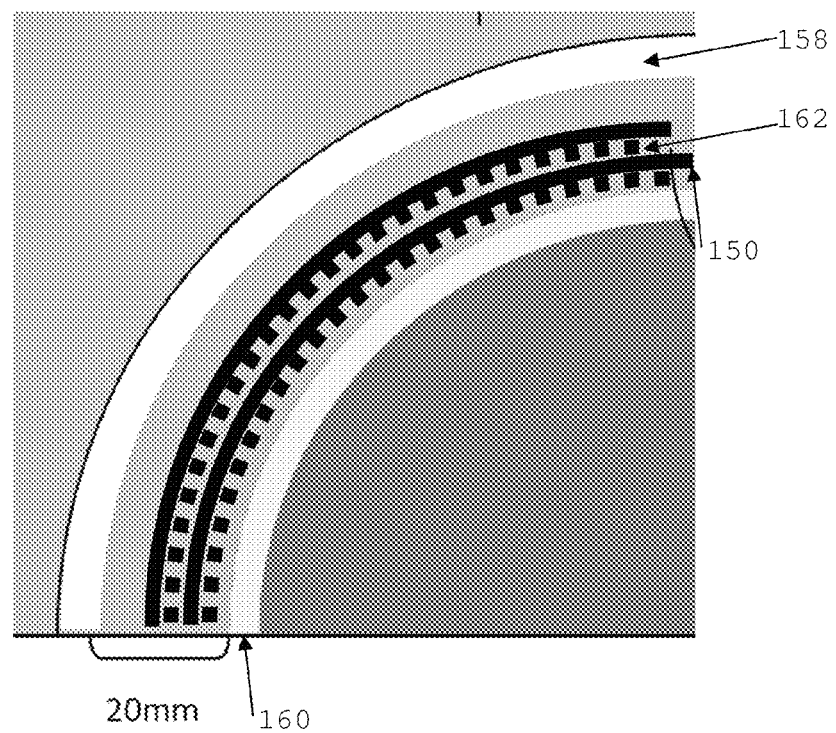
FIG. 15 is a cross-sectional representation of detail 15*b* of FIG. 13.

An algae containment apparatus 50 is shown in FIGS. 13 to 16. Detail 14*b* of FIG. 13 is depicted in FIG. 14 and detail 15*b* of FIG. 13 is depicted in FIG. 15. The algae containment apparatus 50 comprises a first light guide and a second light guide 148. The luminescent material of the first and second light guides is comprised in a plastic substrate 150.

The top portion 152 of the algae containment apparatus 50 is formed with a semi-circular cross-section of a diameter that provides 40 mm of clear water 54 above the containment.

The base portion 154 of the algae containment apparatus 50 is formed with a quarter-circular cross-section of 40 mm diameter and provides at least 40 mm of clear water 54 between the containment and an adjacent containment or a wall of the vessel 144.

The algae containment apparatus is positioned 70 mm above a base of the vessel 144.

As shown in FIG. 14, the top of the second light guide 148 is positioned 100 mm below end of the first light guide 146. The first light guide 146 is coincident with the semi-circular top portion 152 of the algae containment apparatus and does not extend to the upright portion 156 of the algae containment apparatus. The inner air layer 160 of the first light guide 146 extends downwardly to become the outer air layer of the second light guide 148. The luminescent material comprised in a plastic substrate 150 of the second light guide 148 extends above the quarter-circular base portion 154 and is spaced from the first light guide 146.

Figure 4H:
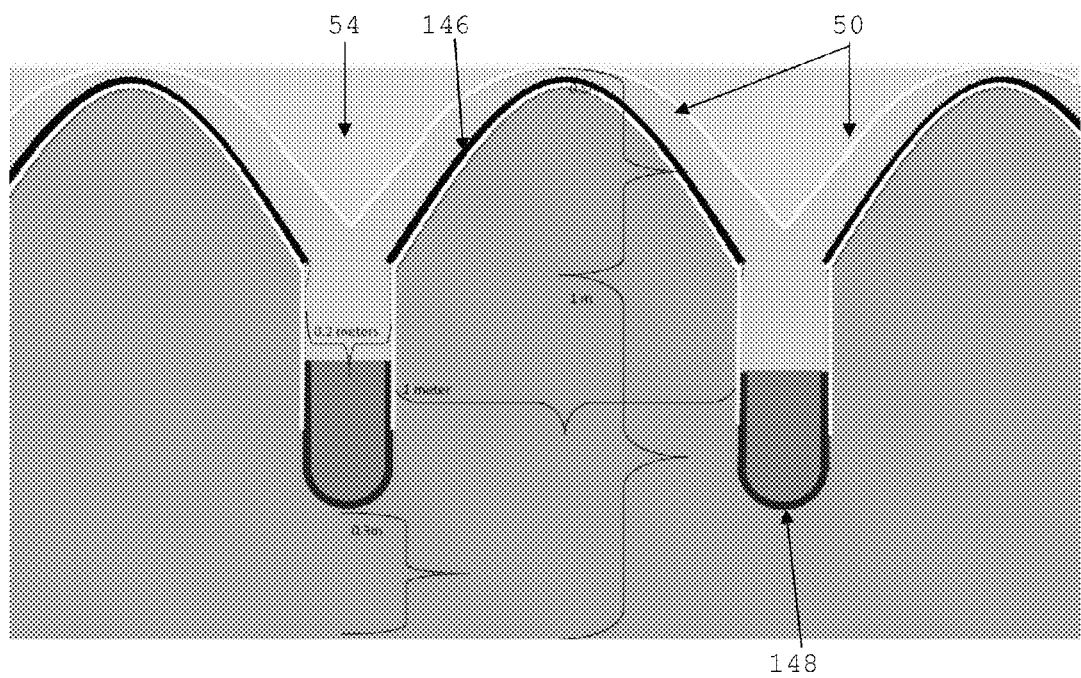

As depicted in FIGS. 14 and 15, the plastic substrate 150 comprising the luminescent material of the first 146 and second 148 light guides comprises light extractors 162 facing towards the algae. The first light guide 146 comprises two plastic substrates 150. The first 146 and second 148 light guides are also depicted in FIG. 4*h*.

The air layers 158, 160 are formed by a sealed, double layer of plastics material. The adhesive used to seal the double layer of plastics will provide sufficient spacing to form the air layer, which may be less than 1 μm. It is important that the air layers 158, 160 are smooth and not wrinkled. Therefore, polycarbonate or other rigid plastic is suitable to form the air layers of the light guides.

In light of the above example of manufacturing an algae containment apparatus, the following steps can be used to manufacture a laboratory scale bioreactor.

1. Acquire a tank of the desired dimensions for algae growth. The depth of the tank is dependent on the light source used. For direct sunlight in outdoor use, the tank may be up to 1500 mm deep. Indoor lighting will not be able to sustain such a depth of algae growth no matter how efficient the light guide system may be.

2. Construct a rigid, sealed insert 142 that is open on top. The width of the insert should allow 10 mm on each side to allow for tubing to fit between the insert and the inner wall of the tank for exchange of gases and media. An upper lip can hold the insert to the top of the vessel 144 so that it does not sink or move when being used.

Figure 16:
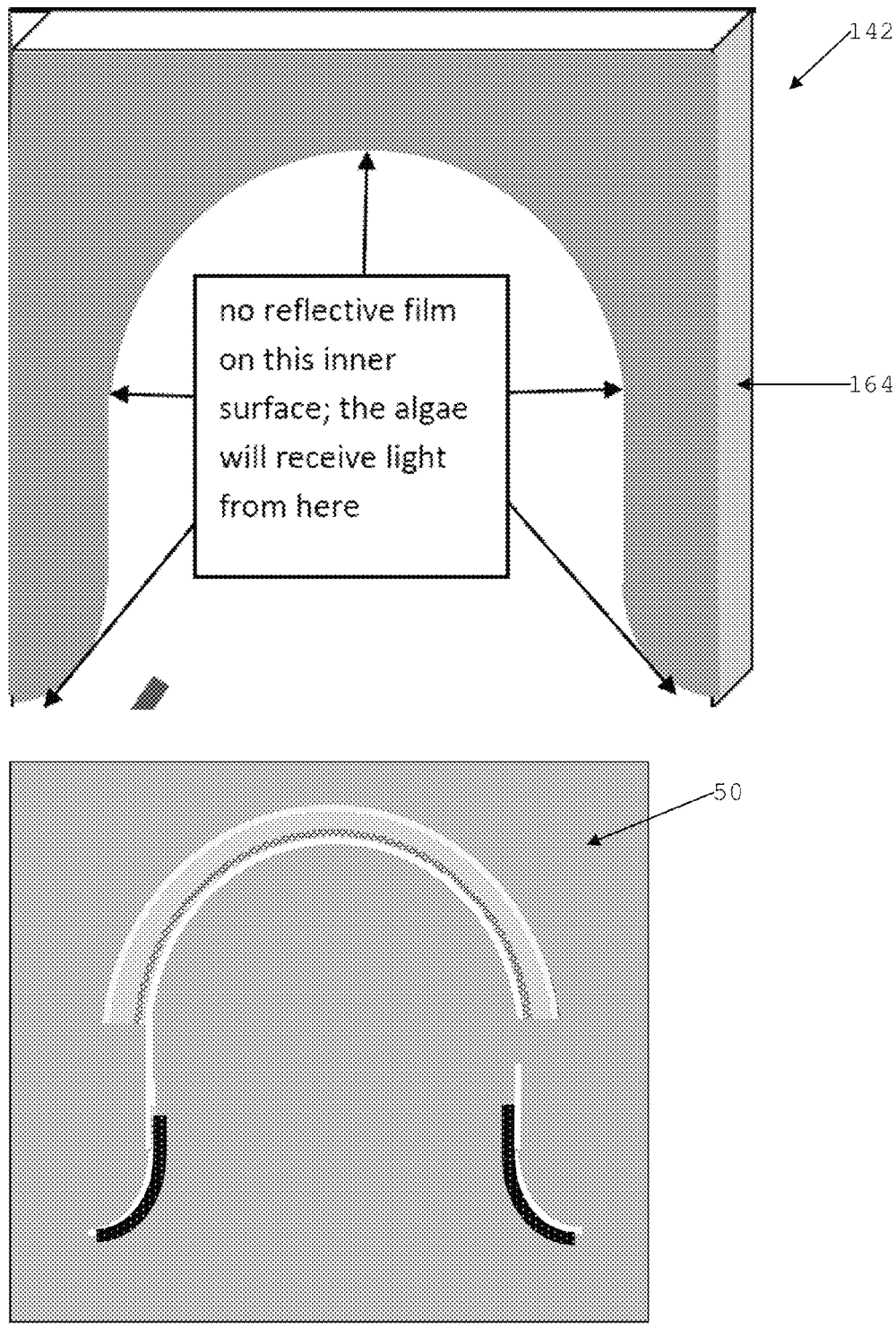
FIG. 16 is a representation of the insert (upper) prior to its sealing to the algae containment apparatus (lower) to form the sealed insert.

3. As shown in FIG. 16, apply reflective film 164 (reflective side down) to the entire surface area of the sealed insert 142, except for the inner surface from which the algae will receive light. This will prevent the guided light from escaping the tank. The tank acts a small cross section of a full scale system and thus requires these measures to contain the light. The full scale system extends lengthwise and does not require reflective film to contain the guided light.

Use a water resistant adhesive such that the reflective film 164 does not come loose and so algae water cannot access between the reflective film and the insert outer walls. This will create a permanent cover on the insert.

4. Create the algae containment apparatus(es) 50 comprising air layers 158, 160 and luminescent plastic substrates 150 as a separate unit that slips inside the sealed insert 142, as shown in FIG. 16.

5. Stabilise the base of the vessel 144 and make a reflective film 164 that can be placed on one face of the vessel and can be removed for viewing.

The finished system will have the rigid, sealed insert 142 will placed inside the tank and the luminescent plastic substrates 150 will be positioned last.

Figure 30:
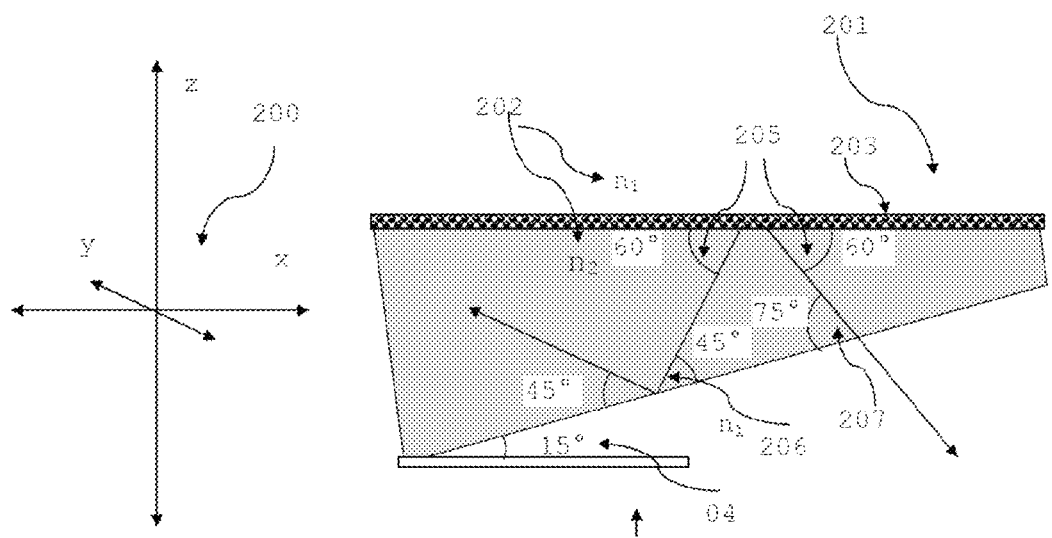
FIG. 30 depicts a set of standard Cartesian x, y, z axes of a light guide and a representation of the light guide which widens in one direction, along the x axis, which favors light guidance in the direction of the widening.

Example of a Light Guide that Expands Along One Axis or Two Axes:

FIG. 30 depicts a standard Cartesian x, y, z axis 200 where a light guide 201 consisting of a layer of substance of high refractive index is surrounded by a layers of material of low refractive index as $n_2$ and $n_1$ respectively 202. The luminescent polymer with formations 203 is facing the downwards z direction into the layer of high refractive index material and emits light into said layer. In this convention, we describe the directions to the left and right to be the x axis and direction perpendicular to the plane of the diagram will be the y axis.

Figure 31:
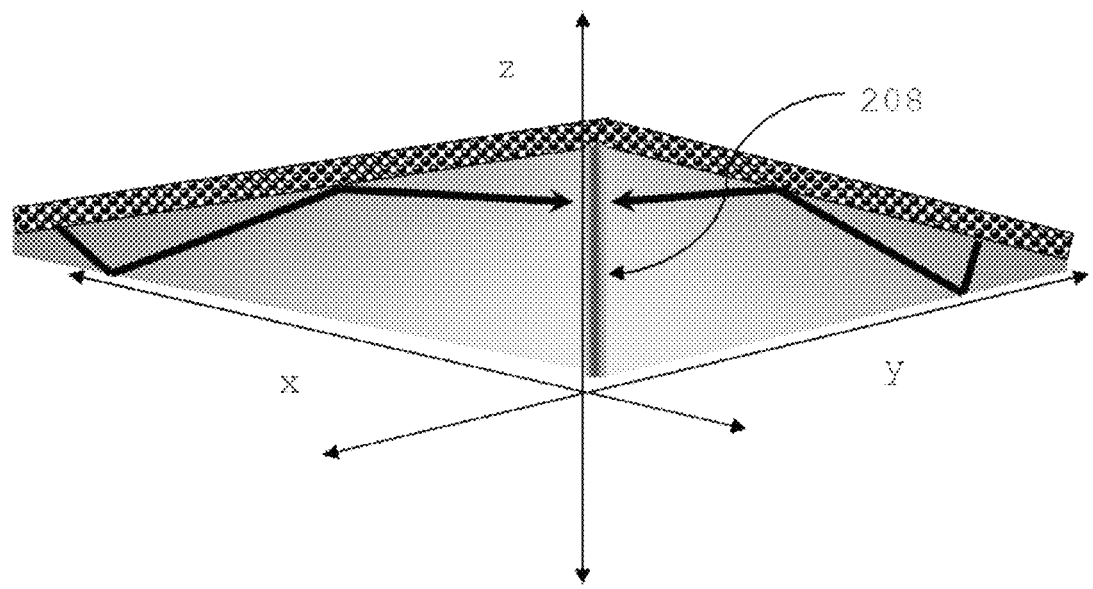
FIG. 31 shows the same concept as FIG. 30, but the light guide widens along both the x and y axes such that light may be guided along a specific xy vector.

In order to add another degree of control over the guidance of luminescence from the polymer layer, the light guide widens in one direction, along the x axis, which favors light guidance in the direction of the widening, in this case to the left. In this example the light guide widens at an angle of 15 degrees 204. Two rays of light are emitted at equal angles of 60 degrees toward the left and right 205. The sloping angle of the light guide edge encourages the ray light travelling to the left to be totally internally reflected by decreasing the angle of incidence on the sloping edge to 45 degrees 206, but the ray emitted towards the right strikes the light guide edge at 75 degrees 207, which is beyond the critical angle between most polymers or liquids and air, and is shown to escape the light guide. This technique does not increase or decrease the amount of light guided by the device overall, but it does allow more light to be emitted towards the left, or wider side, than the more narrow side. This technique is an important feature of the invention by allowing us to not only selectively extract light in the downwards direction by use of formations in the luminescent polymer, but we can then selectively guide that light to the left or to the right. FIG. 31 shows the same concept where the light guide widens along both the x and y axis such that light may be guided along a specific xy vector 208.

Figure 32:
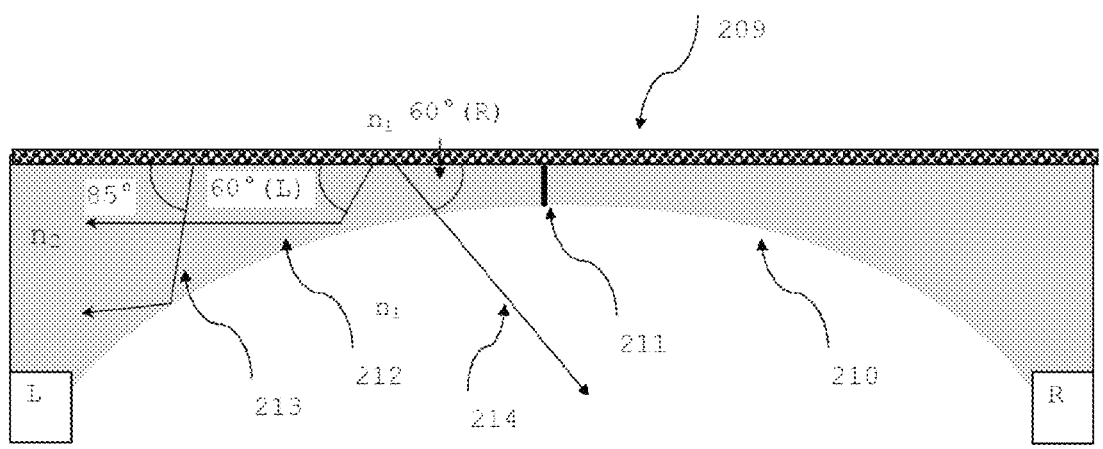
FIG. 32 is a representation of a light guide of similar composition to that of FIG. 30 with a variation such that widening of the light guide is achieved using a curved edge, where the slope of the lower edge of the light guide is exponentially increasing as it continues outward away from the centre of the light guide.

In FIG. 32, another example light guide of the same composition of FIG. 30 is shown 209. The variation here is that the aspect of widening the light guide is shown using a curved edge 210 where the slope of the lower edge of the light guide is exponentially increasing as it continues outward away from the centre of the device 211. In this design, the light guide will increasingly favour light guidance away from the centre of the device more so as we move further to the left and right.

In this example a light ray is emitted at 60 degrees towards the left, close to the centre, and is totally internally reflected 212. Another light ray is emitted, further from the centre, at 85 degrees 213 and would surely escape a linear light guide without a sloping design. In this design however, such a steep angle of emission can be totally internally reflected because the slope of the lower edge of the light guide has become almost vertical at this point 213. A third light ray is emitted to the right at 60 degrees 214, and escapes the light guide since the angle of incidence on the curved edge of the light guide is beyond the critical angle.

Figure 33:
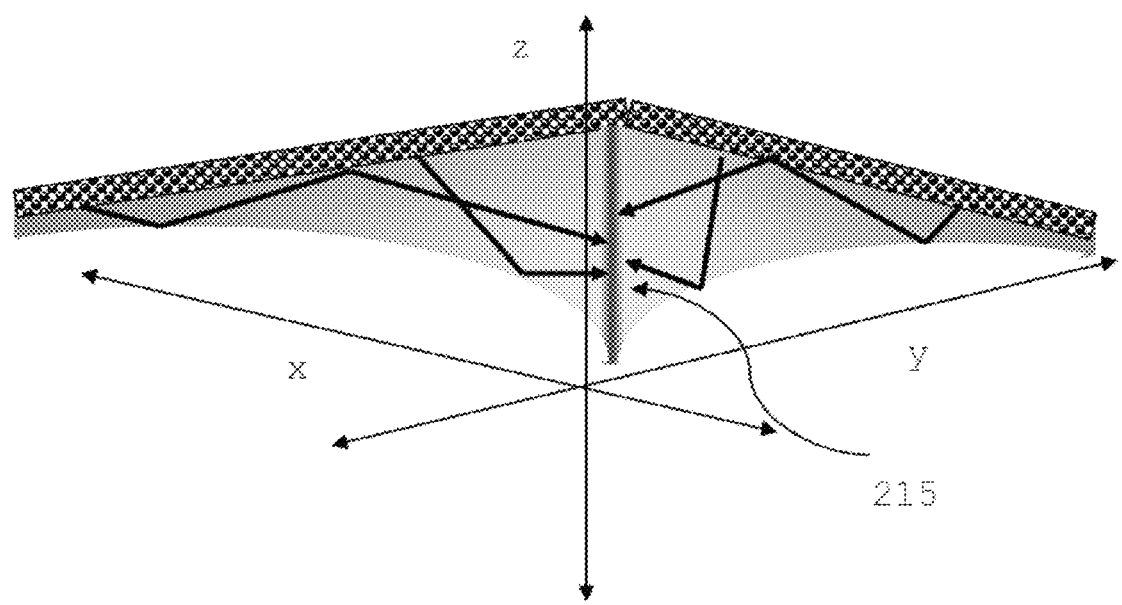
FIG. 33 depicts a light guide similar to that of FIG. 32 in which the curved widening occurs in both the x and y directions to favour total internal reflection down a specific xy vector.

As with the non-curved widening light guide in FIG. 31, the curved widening light guide in FIG. 32 may widen in both the x and y directions as shown in FIG. 33 to favour total internal reflection down a specific xy vector 215.

Figure 34:
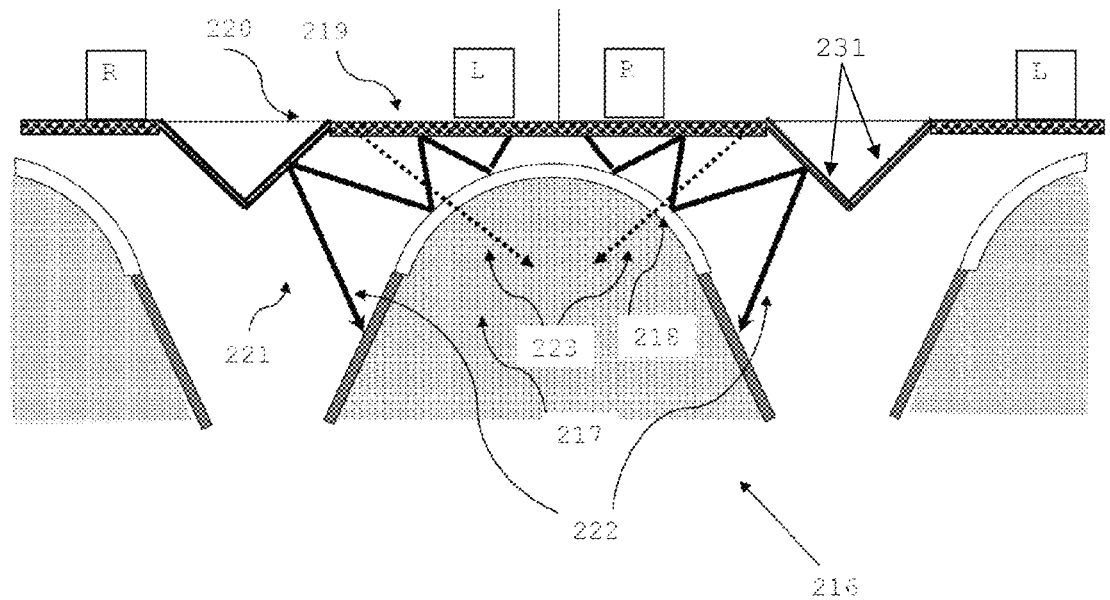
FIG. 34 depicts an algae bioreactor comprising a light guide with a curved widening lower edge.

For the application of growing phototropic biomass, i.e. algae, seaweed and plants, the advantage of guiding light outwards away from the centre of the light guide prevents light rays from taking a overly long path length from where it is first emitted from the luminescent polymer to when it reaches the lower regions of the system by total internal reflection. In FIG. 34, a light guide with a curved widening lower edge is part of an algae bioreactor 216. The algae containment 217, has a double layer of plastic 218 on its upper half where a layer of air is trapped between the layers and thus forms a layer of lower refractive index to act as the lower edge of the light guide. The luminescent polymer 219 with light extraction formations facing downwards is positioned near the surface of a clear media (water) and uses the above existing air/water interface as the upper boundary of the light guide 220. This feature saves costs by reducing the amount of material that would normally be required to form this boundary under water. The polymer is separated from the algae containment by a layer of clear media that acts as the light guiding media 221. At the left and right edges of the polymer layer are two flaps of double layered plastic that act as layers of air creating boundaries of a low refractive index. These boundaries are angled downwards as shown to guide light travelling in a horizontal direction to be turned downwards where it can be utilised by the algae growth.

Light rays produced on the left are guided to the left 222 and visa versa 222. Light rays that are emitted from the left side, but travelling towards the right escape the light guide downwards directly into the upper region of growth where it can be utilised by the upper regions of algae growth 223 and vice versa 223.

Without the widening aspect the light rays produced on the left but travelling towards the right would need to travel up past the centre of the device and then down the right side to reach the target and vice versa. This long path length must be avoided so that the light ray is less likely to be subjected to optical losses such as re-absorption and light attenuation. The objective that is achieved by this widening aspect is that we minimise the amount of time the light spends within the light guide before it is utilised.

Example Prototypes and Algae Growth Results

Figure 35:
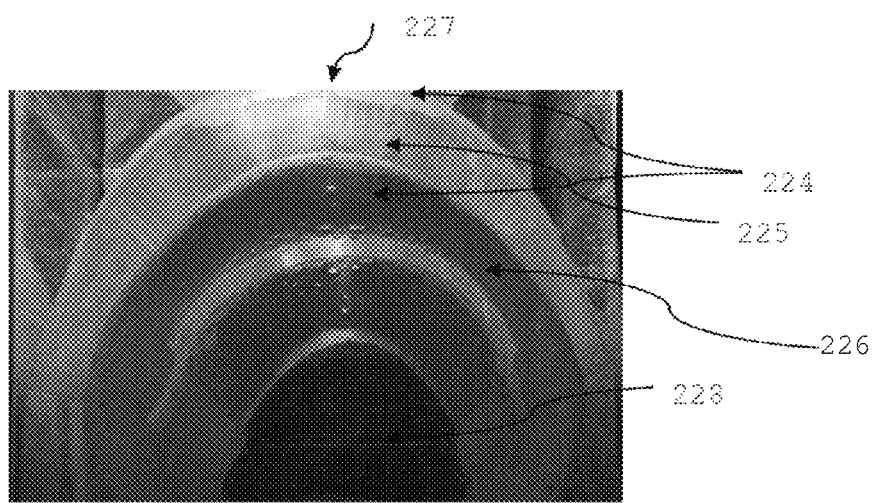
FIG. 35 depicts a light guide without widening that displays excellent light guiding ability in water.

FIG. 35 depicts a prototype light guide without a widening aspect that displays excellent light guiding ability in water. The algae containment is not included for simplicity. The upper and lower layers are comprised of double layers of plastic 224 that contain a layer of air to create boundaries of low refractive index. The upper layer is also comprised of a luminescent polymer sheet with formations 225 that extract light in a downwards direction. The dark underside 226 of the plastic is due to the layer of air trapped between the plastic layers preventing light shining from above 227 from penetrating and instead guides the light to the sides and towards the lower region of the device 228.

Figure 36:
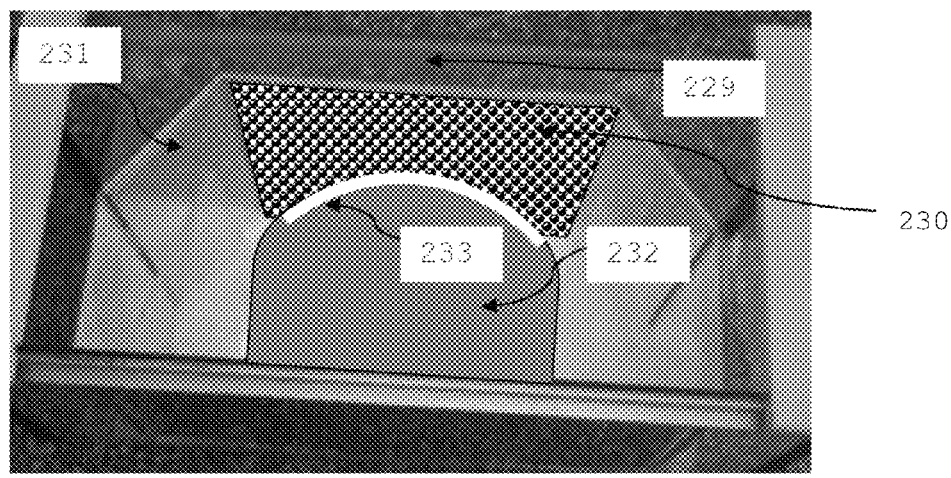
FIG. 36 is a photograph of a light guide and bioreactor with the features of FIG. 34 complete with the straight upper boundary where the luminescent polymer with light extractors and side flaps of double layer plastics that maintain the air boundary for guiding light downwards.

The picture below this prototype in FIG. 36 shows a prototype with the features described in FIG. 34 complete with the straight upper boundary 229 where the luminescent polymer with extraction formations are placed 230 and side flaps of double layer plastics 231 that maintain the air boundary for guiding light downwards. The algae containment 232 is placed as shown complete with a double plastic layer for maintaining the air boundary of the light guide 233. The round shape of the algae containment provides the curved widening slope of the light guide.

Figure 37:
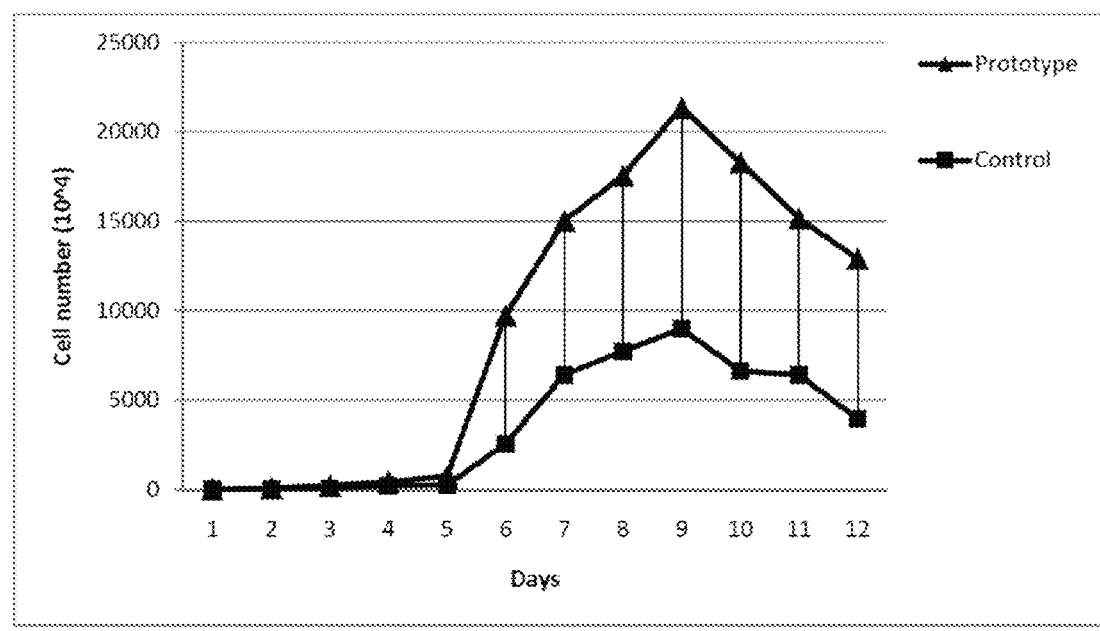
FIG. 37 plots the increased growth rates and densities achieved using the light guide of FIG. 36.

The graph below 233 in FIG. 37 shows the increased growth rates and densities achieved by using this prototype model in FIG. 36. The algae biomass achieves a density that 230% greater than a control apparatus that lacks any luminescent polymers, air layers or other light guiding features.

Plant Trial of the Luminescent Growing Apparatus

Figure 29:
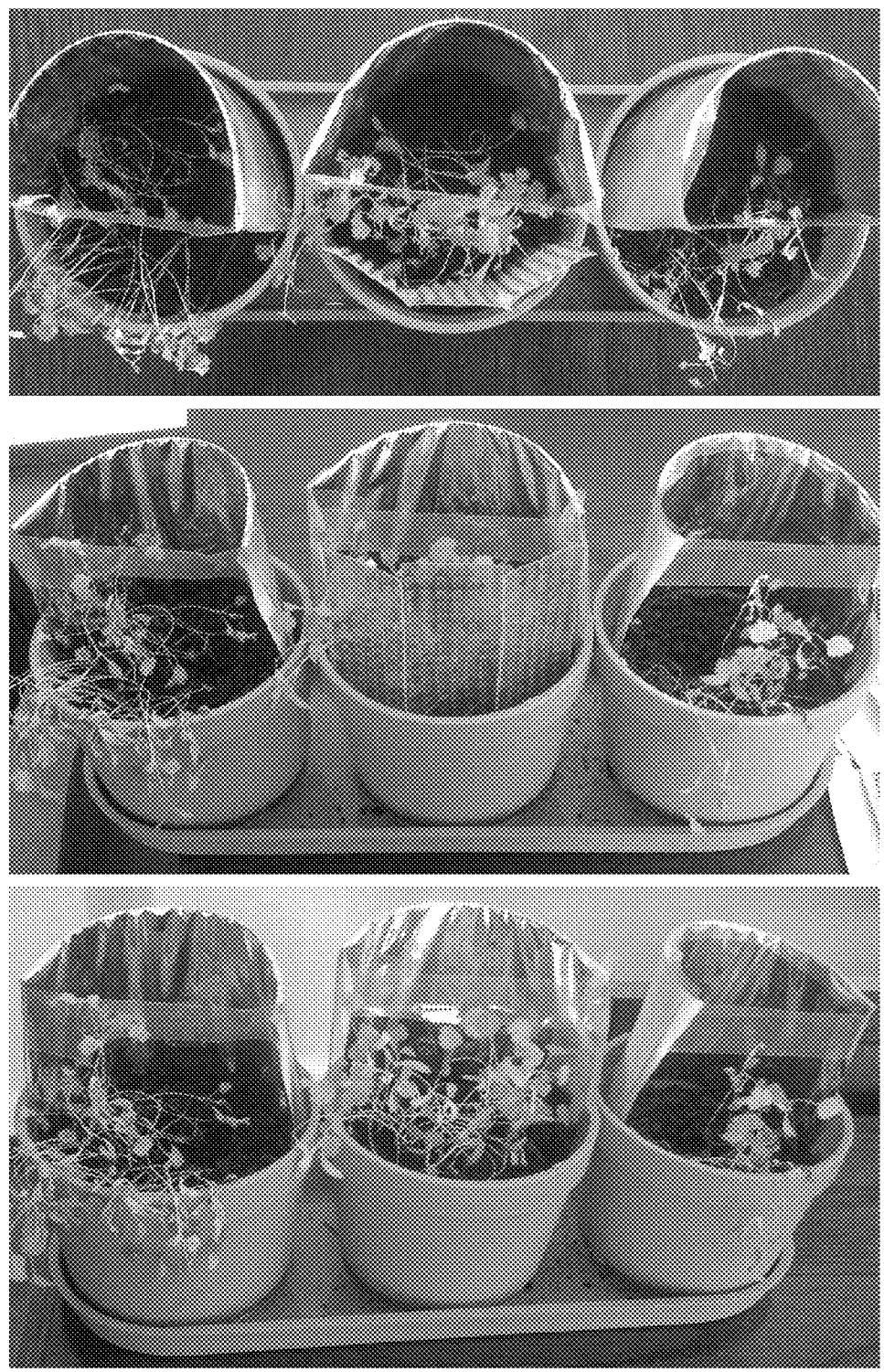
FIG. 29 shows photographs of three identical plant pots filled with potting soil and planted with Coriander seeds. The centre pot comprised a luminescent growing apparatus of the disclosure, which resulted in better growth than the flanking pots. The luminescent growing apparatus can be seen in the centre pot in the upper two photographs, but is not seen in the centre pot of the lowermost photograph, because it was removed to give a clear view of the plant.

Three identical plant pots were filled with potting soil and each planted with a handful of Coriander seeds that were store bought (FIG. 29). In each pot was inserted a reflective backing to limit light for plant growth to one direction. The centre pot was also fixed with a light extractor of the disclosure that absorbs strongly in the green portion of the spectrum (absorbance maximum at 545 nm) and fluoresces at a maximum of 575 nm to 620 nm, orange/red. The light extractors were directed towards the plant growth.

The pots were placed on a window sill indoors and were exposed to mostly diffuse sunlight during the winter months. The sprouting plants received only 2.5 hours of direct sunlight daily on clear weather in the late afternoon, while only receiving diffuse light for the remainder of the day over a 2 month period. Coriander normally requires full, strong sunlight to thrive and the amount of sunlight in this experiment was purposefully chosen to be of insufficient, limited amounts. The purpose was to observe if the luminescent growing apparatus made better use of the sunlight available in a light-limited scenario.

Overall, it is clear that the plants growth suffered for all three pots due to lack of sunlight. Over a 2 month period, the plant growth should have been much more significant. It is very clear however, that the middle pot suffered much less than the other two. The plant growth is upright and even across the soil.

The other two pots show an almost desperate reaching for sunlight where the plants are drooping over the edge trying to find more light for growth. The stalks are stringy with fewer leaves and are generally in much worse condition than the middle pot.

While all plant growth was sub-optimal due to limited sunlight, the pot that was aided by the light extractors grew much better than those without. The light extractors can improve growth by optimising the spectrum of available light, turning green to orange/red by fluorescence. The light extractors were critical in providing exit points for the fluorescence to reach the plants.

Flowering Tree (Frangipani) Trial of the Luminescent Growing Apparatus

Figure 38:
FIG. 38 depicts a 10×5 cm light guide with light extractors in the upper portion of one of four branches on a potted Frangipani tree at the start of the growth season just before leaves or flowers have begun to grow.

FIG. 38 depicts a small 10×5 cm sample of the luminescent polymer with extraction formation placed on the upper portion of one of four branches on a potted Frangipani tree at the start of the growth season just before leaves or flowers have begun to grow. The tree receives direct sunlight, but not enough to induce flowering and has not flowered in three years. The tree did have flowers on all branches when it was purchased. The conditions where it sits allow for ample leaf development but not flowers.

In FIG. 38A, B and C the luminescent polymer is shown to absorb sunlight at the backside of the formations and emit the luminescence towards the plant on the other side. All four branches of the tree began to grow their first leaves of the season, but in picture C, the beginning of a flower bud emerges where the luminescent polymers have been placed, but not on any other branches that all receive equal amounts of sunlight exposure and are of the same quality and health.

In FIGS. 38D and E the luminescent polymer is removed for viewing of the more developed flower bud but is then replaced for further growth. FIG. 38F shows the entire tree with flowers growing from the one branch that the luminescent polymer was placed. FIG. 38G shows a close up of the developed flowers. Once the flowers began to blossom, the luminescent polymers were removed and the flowers persisted until the end of the season. No flowers grew from any other branches, though they all developed healthy amounts of green leaves.

The luminescent polymers delivered the correct wavelengths and intensities of light that are required for flowering in this plant. This displays the application of this invention for the enhanced growth of terrestrial plants.

It will be understood to persons skilled in the art of the invention that many modifications may be made without departing from the spirit and scope of the invention.

The invention claimed is:

1. A bioreactor comprising a plurality of containment apparatuses, each containment apparatus comprising a first light guide, wherein:
   the first light guide is a luminescent light guide comprising a first luminescent material; and
   the first light guide guides light to a second luminescent material underneath the first light guide; and
   the first light guide luminescent material emits visible light between 540 nm and 600 nm suitable for absorption by the second luminescent material; and
   a second light guide is formed between adjacent containment apparatuses.

2. The bioreactor of claim 1, wherein each containment apparatus underneath the first light guide comprises the second luminescent material that absorbs visible light emitted by the first luminescent material.

3. The bioreactor of claim 2, wherein the second luminescent material emits red light.

4. The bioreactor of claim 1, wherein the second light guide is a liquid-filled light guide.

5. The bioreactor of claim 4, wherein the liquid-filled light guide is filled with clear water.

6. The bioreactor of claim 1, wherein the first light guide or the second light guide widens in one axis.

7. The bioreactor of claim 1, wherein the first light guide or the second light guide widens in two axes.

8. The bioreactor of claim 1, wherein the first light guide or the second light guide comprises a non-curving surface for internal reflection.

9. The bioreactor of claim 1, wherein the first light guide or the second light guide comprises a curving surface for internal reflection.

10. The bioreactor of claim 1, wherein the second light guide further comprises a double wall that maintains a boundary for guiding light.

11. The bioreactor of claim 1, wherein the first light guide comprises a light extractor that extracts light from the first luminescent material at angles that would otherwise be trapped by total internal reflection according to the refractive index of the first luminescent material.

12. The bioreactor of claim 11, wherein light is extracted in one direction.

13. The bioreactor of claim 11, wherein light is extracted in more than one direction.

14. The bioreactor of claim 1, wherein the first light guide is adapted to reduce reabsorption of luminescence by the first luminescent material.

15. The bioreactor of claim 14, wherein the first light guide is adapted to reduce reabsorption by means of a substrate lacking a luminescent material and of sufficient refractive index that luminescence is guided by the substrate.

16. The bioreactor of claim 1, wherein each containment apparatus is triangular, with a base positioned away from a light source and a vertex positioned towards the light source.

17. The bioreactor of claim 1, wherein each containment apparatus is tubular and triangular, with a base positioned away from a light source and a vertex positioned towards the light source.

18. The bioreactor of claim 1, further comprising a bio-digester.

19. A method for growing an aquatic plant, an alga or a cyanobacterium comprising growing the aquatic plant, alga or cyanobacterium in the of bioreactor of claim 1.

* * * * *